(12) United States Patent
Mitchell et al.

(10) Patent No.: US 6,623,576 B2
(45) Date of Patent: Sep. 23, 2003

(54) CONTINUOUS MANUFACTURE OF SUPERABSORBENT/ION EXCHANGE SHEET MATERIAL

(75) Inventors: Michael A. Mitchell, Lake Zurich, IL (US); Mark Anderson, Wheaton, IL (US); Thomas W. Beihoffer, Arlington Heights, IL (US)

(73) Assignee: BASF Aktiengesellschaft, Ludwigshafen (DE)

( * ) Notice: Subject to any disclaimer, the term of this patent is extended or adjusted under 35 U.S.C. 154(b) by 266 days.

(21) Appl. No.: 09/875,593

(22) Filed: Jun. 6, 2001

(65) Prior Publication Data

US 2002/0007166 A1 Jan. 17, 2002

Related U.S. Application Data

(60) Continuation-in-part of application No. 09/746,177, filed on Dec. 22, 2000, which is a continuation-in-part of application No. 09/179,554, filed on Oct. 28, 1998, now Pat. No. 6,194,631, and a continuation-in-part of application No. 09/551,963, filed on Apr. 19, 2000, now Pat. No. 6,392,116, which is a division of application No. 09/179,553, filed on Oct. 28, 1998, now Pat. No. 6,222,091.

(51) Int. Cl.[7] .......................... B32B 31/00; B29B 13/00
(52) U.S. Cl. .................... 156/62.2; 264/122; 264/126; 156/276
(58) Field of Search ............................. 156/62.2, 276; 264/122, 126

(56) References Cited

U.S. PATENT DOCUMENTS

| | | |
|---|---|---|
| 3,041,292 A | 6/1962 | Hatch .......................... 260/2.1 |
| 3,332,890 A | 7/1967 | Hatch .......................... 260/2.1 |
| 3,645,922 A | 2/1972 | Weiss et al. ............. 260/2.1 R |
| 3,716,481 A | 2/1973 | Battaerd ....................... 210/32 |
| 3,901,236 A | 8/1975 | Assarsson et al. .......... 128/284 |
| 3,957,698 A | 5/1976 | Hatch ...................... 260/2.1 R |
| 4,018,826 A | 4/1977 | Gless, Jr. et al. ........ 260/583 P |

(List continued on next page.)

FOREIGN PATENT DOCUMENTS

| | | | |
|---|---|---|---|
| CA | 2066010 | 10/1992 | ............ B01J/20/26 |

(List continued on next page.)

OTHER PUBLICATIONS

Bolto et al., *J. Polymer. Sci.*, Symposium No. 55, 87–94 (1976).

(List continued on next page.)

*Primary Examiner*—Stephen J. Lechert, Jr.
(74) *Attorney, Agent, or Firm*—Marshall, Gerstein & Borun

(57) ABSTRACT

A continuous sheet having a combination of acidic and basic water-absorbing resin particles that are essentially not neutralized and can be continuously manufactured on conventional papermaking apparatus, using a wet, dry, or wet-dry process to manufacture a water-absorbent sheet-like substrate containing 50%–100% by weight of the combination of acidic and basic water-absorbent particles. The acidic and basic essentially unneutralized resins can be contained in the sheet material articles of the present invention as separate acidic and basic resin particles, or as multicomponent particles containing both the acidic and basic resins. The sheet materials can be manufactured having new and unexpected structural integrity, with little or no shakeout or loss of superabsorbent particles during or after manufacture while exhibiting exceptional water absorption and retention properties.

50 Claims, 26 Drawing Sheets

U.S. PATENT DOCUMENTS

| | | | |
|---|---|---|---|
| 4,139,499 A | 2/1979 | Wade et al. | 521/32 |
| 4,206,051 A | 6/1980 | Bolto et al. | 210/26 |
| 4,229,545 A | 10/1980 | Eppinger et al. | 521/38 |
| 4,378,439 A | 3/1983 | Pilkington | 521/26 |
| 4,578,068 A | 3/1986 | Kramer et al. | 604/368 |
| 4,685,909 A | 8/1987 | Berg et al. | 604/360 |
| 4,798,871 A | 1/1989 | Lai et al. | 525/328.2 |
| 4,804,793 A | 2/1989 | Lai et al. | 574/445 |
| 4,818,598 A | 4/1989 | Wong | 428/284 |
| 4,843,118 A | 6/1989 | Lai et al. | 524/555 |
| 4,846,932 A | 7/1989 | Karita et al. | 162/127 |
| 4,964,463 A | 10/1990 | Shu | 166/270 |
| 5,026,800 A | 6/1991 | Kimura et al. | 526/200 |
| 5,075,399 A | 12/1991 | Ahmed et al. | 526/287 |
| 5,079,080 A | 1/1992 | Schwarz | 428/288 |
| 5,085,787 A | 2/1992 | Pinschmidt, Jr. et al. | 252/8.551 |
| 5,126,395 A | 6/1992 | End et al. | 524/801 |
| 5,274,018 A | 12/1993 | Tanaka et al. | 524/166 |
| 5,340,865 A | 8/1994 | Neff et al. | 524/922 |
| 5,360,420 A | 11/1994 | Cook et al. | 604/378 |
| 5,384,343 A | 1/1995 | Farrar et al. | 524/556 |
| 5,409,771 A | 4/1995 | Dahmen et al. | 428/327 |
| 5,447,727 A | 9/1995 | Graham | 424/487 |
| 5,464,908 A | 11/1995 | Sato et al. | 525/380 |
| 5,491,199 A | 2/1996 | Ford et al. | 525/362 |
| 5,547,745 A | 8/1996 | Hansen et al. | 428/283 |
| 5,562,646 A | 10/1996 | Goldman et al. | 604/368 |
| 5,599,335 A | 2/1997 | Goldman et al. | 604/368 |
| 5,607,550 A | 3/1997 | Akers | 162/102 |
| 5,612,384 A | 3/1997 | Ross et al. | 521/64 |
| 5,662,781 A | 9/1997 | Denzinger et al. | 204/158.21 |
| 5,669,894 A | 9/1997 | Goldman et al. | 604/368 |
| 5,716,707 A | 2/1998 | Makaida et al. | 428/402 |
| 5,762,641 A | 6/1998 | Bewick-Sonntag et al. | 604/378 |
| 5,763,523 A | 6/1998 | Chen et al. | 524/922 |
| 5,797,893 A | 8/1998 | Wada et al. | 604/372 |
| 5,804,605 A | 9/1998 | Palumbo | 521/28 |
| 5,843,575 A | 12/1998 | Wang et al. | 428/407 |
| 5,847,013 A | 12/1998 | Ross et al. | 528/363 |
| 5,849,405 A | 12/1998 | Wang et al. | 428/304.4 |
| 5,849,862 A | 12/1998 | Davies et al. | 528/502 E |
| 5,851,672 A | 12/1998 | Wang et al. | 428/407 |
| 5,985,432 A | 11/1999 | Wang et al. | 428/304.4 |
| 5,997,690 A | 12/1999 | Woodrum | 162/100 |
| 6,222,091 B1 | 4/2001 | Beihoffer et al. | |
| 2001/0006267 A1 * | 7/2001 | Harada et al. | 264/140 |

FOREIGN PATENT DOCUMENTS

| | | | | |
|---|---|---|---|---|
| DE | 40 07 310 A | 9/1991 | | C08F/26/02 |
| DE | 42 32 241 A | 4/1993 | | C08F/26/02 |
| DE | 43 23 234 A | 1/1995 | | C08F/26/02 |
| DE | 43 33 056 | 3/1995 | | C08F/8/00 |
| EP | 0 359 615 | 3/1990 | | A61L/15/60 |
| EP | 0 437 816 | 7/1991 | | D21H/21/22 |
| EP | 0 478 150 | 4/1992 | | |
| EP | 0 700 672 | 3/1996 | | A61F/13/15 |
| EP | 0 702 031 | 3/1996 | | |
| EP | 0 882 502 | 12/1998 | | |
| JP | 61 051007 | 3/1986 | | C08F/8/12 |
| WO | WO 95/22358 | 8/1995 | | A61L/15/60 |
| WO | WO 95/26209 | 10/1995 | | A61L/15/42 |
| WO | WO 96/15162 | 5/1996 | | C08F/20/06 |
| WO | WO 96/15163 | 5/1996 | | C08F/20/56 |
| WO | WO 96/15180 | 5/1996 | | C08J/5/02 |
| WO | WO 96/17682 | 6/1996 | | B01J/20/00 |
| WO | WO 98/24832 | 6/1998 | | C08J/3/075 |
| WO | WO 98/37149 | 8/1998 | | C08L/101/14 |
| WO | WO 99/25745 | 5/1999 | | |
| WO | WO 00/56959 | 9/2000 | | |
| WO | WO 00/61642 | 10/2000 | | |

OTHER PUBLICATIONS

Zhang et al., *Narure*, 360, 142–144 (1992).

Salamone et al., *Polym. Mater. Sci. Eng.*, 55, 269–273 (1986).

McCormick et al., *Macromolecules*, 21, 694–699 (1988).

Bolto, *Polymeric Amines and Ammonium Salts*, Goethals, Ed., Paragon Press, New York, p. 365 (1979).

Bolto et al., *J. Polymer Sci.: Symposium Ser.*, 95–104 (1976).

Badesso et al., *Hydrophilic Polymers; Performance with Environmental Acceptability*, Glass, Ed., American Chemical Society (1996).

St. Pierre et al., *Polym. Amines Ammonium Salts, Invited Lect. Contrib. Pap. Int. Symp.*, Goethals, Ed., p. 245 (1980), meeting date 1979.

Chang et al., *Macromolecules*, 20(3), 621–625 (1987).

Robeson, *J. App. Poly. Sci.*, 61, 1561–1569 (1996).

* cited by examiner

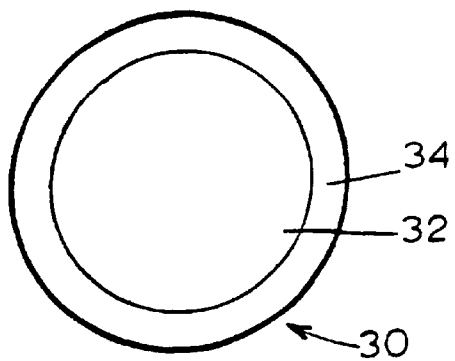
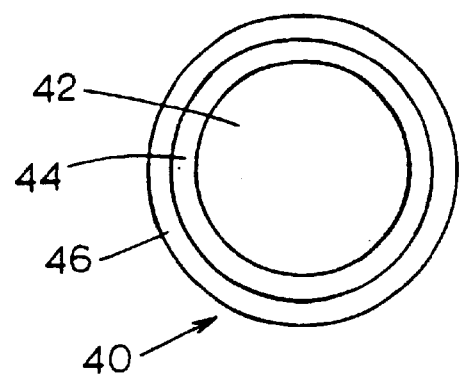
Fig. 3A  Fig. 3B
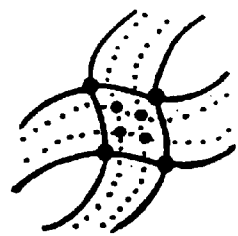
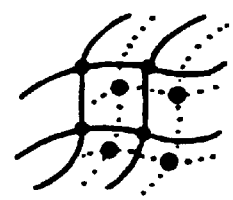
Fig. 5A  Fig. 5B

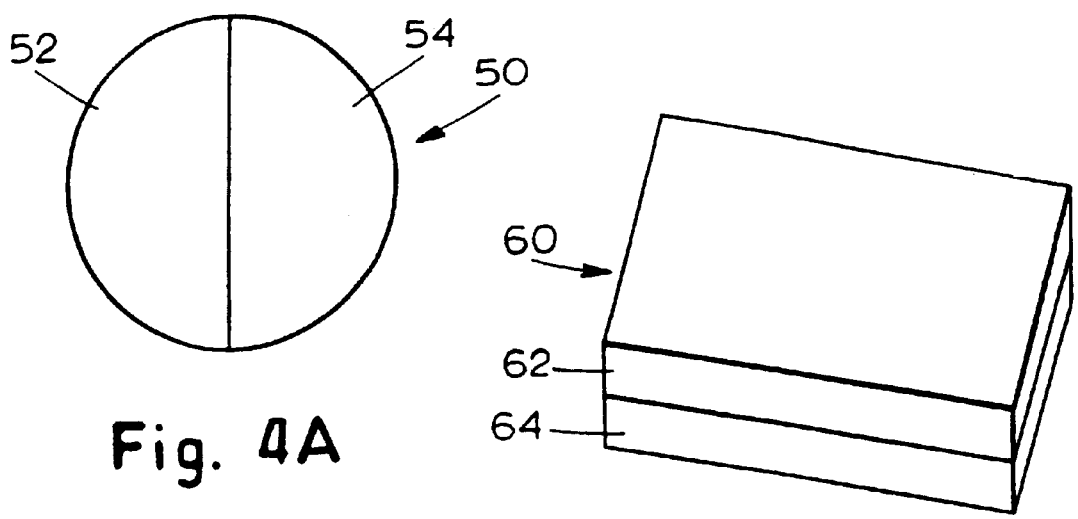
Fig. 4A
Fig. 4B
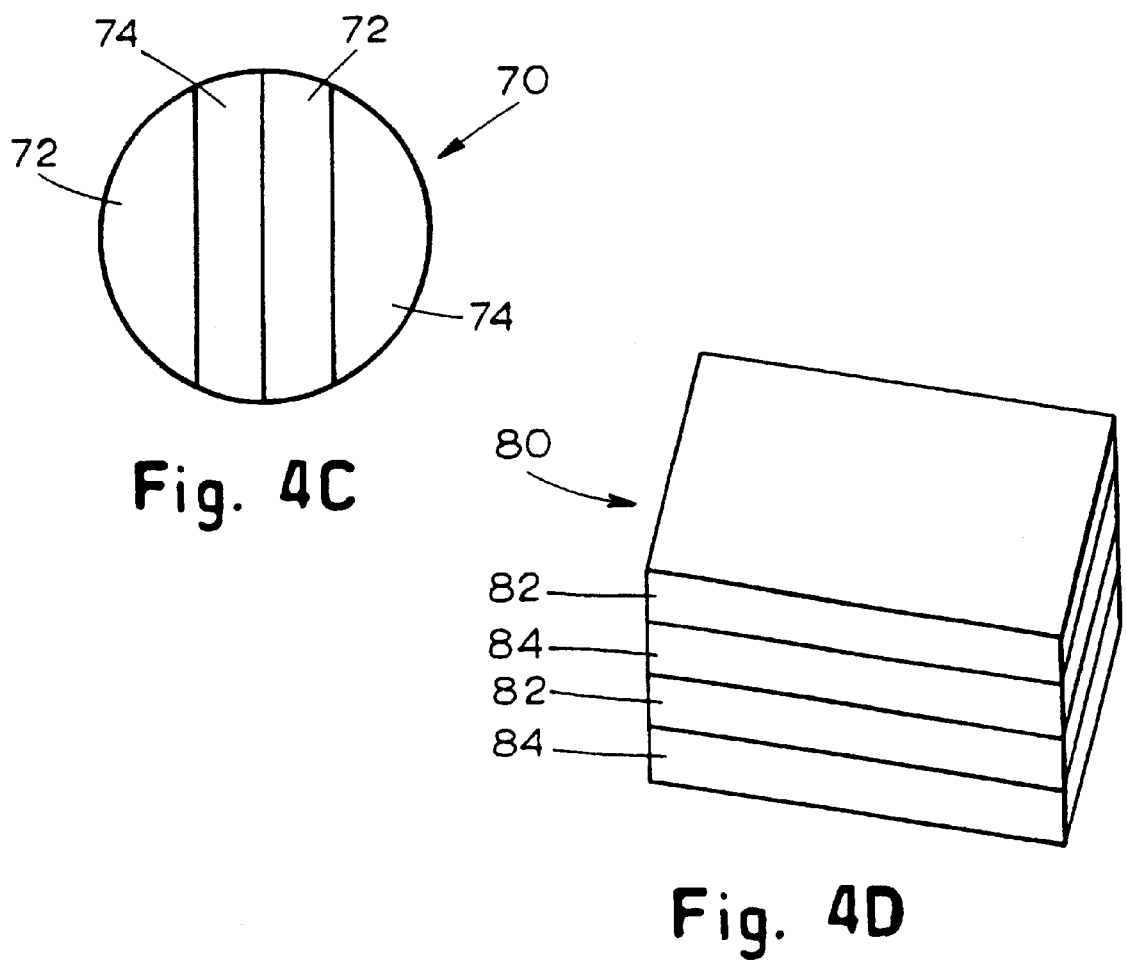
Fig. 4C
Fig. 4D

ABSORBENT/ION EXCHANGE
CONTINUOUS MANUFACTURE OF SUPERABSORBENT/ION EXCHANGE SHEET MATERIAL

CROSS-REFERENCE TO RELATED APPLICATIONS

This is a continuation-in-part of U.S. application Ser. No. 09/746,177, filed Dec. 22, 2000, which is a continuation-in-part of U.S. application Ser. No. 09/179,554, filed Oct. 28, 1998, now U.S. Pat. No. 6,194,631; and is a continuation-in-part of U.S. application Ser. No. 09/551,963, filed Apr. 19, 2000, now U.S. Pat. No. 6,392,116 which is a divisional of U.S. application Ser. No. 09/179,553, filed Oct. 28, 1998, now U.S. Pat. No. 6,222,091.

FIELD OF THE INVENTION

The present invention is directed to a method of manufacturing a paper-like sheet material that includes about 40% to about 100%, by weight, of one or more superabsorbent polymers, and the resulting article of manufacture, that is capable of rapid water uptake; excellent absorption under load (AUL); use as an ion-exchange sheet material layer for removal of unwanted dissolved ions in an aqueous liquid; use as a disposable, water-absorbent towel; has an excellent, smooth feel in a relatively thin absorbent sheet material with unexpectedly high loadings (up to 100% by weight) of superabsorbent polymers; and can be manufactured without fiber or binder while providing excellent structural integrity with little to no shakeout or loss of superabsorbent particles from the sheet material.

BACKGROUND OF THE INVENTION AND PRIOR ART

Water-absorbing resins are widely used in sanitary goods, hygienic goods, wiping cloths, water-retaining agents, dehydrating agents, sludge coagulants, disposable towels and bath mats, disposable door mats, thickening agents, disposable litter mats for pets, condensation-preventing agents, and release control agents for various chemicals. Water-absorbing resins are available in a variety of chemical forms, including substituted and unsubstituted natural and synthetic polymers, such as hydrolysis products of starch acrylonitrile graft polymers, carboxymethylcellulose, crosslinked polyacrylates, sulfonated polystyrenes, hydrolyzed polyacrylamides, polyvinyl alcohols, polyethylene oxides, polyvinylpyrrolidones, and polyacrylonitriles.

Such water-absorbing resins are termed "superabsorbent polymers," or SAPs, and typically are lightly crosslinked hydrophilic polymers. SAPs are generally discussed in Goldman et al. U.S. Pat. Nos. 5,669,894 and 5,559,335, the disclosures of which are incorporated herein by reference. SAPs can differ in their chemical identity, but all SAPs are capable of absorbing and retaining amounts of aqueous fluids equivalent to many times their own weight, even under moderate pressure. For example, SAPs can absorb one hundred times their own weight, or more, of distilled water. The ability to absorb aqueous fluids under a confining pressure is an important requirement for an SAP used in a hygienic article, such as a diaper.

As used here and hereafter, the term "SAP particles" refers to superabsorbent polymer particles in the dry state, i.e., particles containing from no water up to an amount of water less than the weight of the particles. The terms "SAP gel" or "SAP hydrogel" refer to a superabsorbent polymer in the hydrated state, i.e., particles that have absorbed at least their weight in water, and typically several times their weight in water.

The dramatic swelling and absorbent properties of SAPs are attributed to (a) electrostatic repulsion between the charges along the polymer chains, and (b) osmotic pressure of the counter ions. It is known, however, that these absorption properties are drastically reduced in solutions containing electrolytes, such as saline, urine, and blood. The polymers function much less effectively in the presence of such physiologic fluids.

The decreased absorbency of electrolyte-containing liquids is illustrated by the absorption properties of a typical, commercially available SAP, i.e., sodium polyacrylate, in deionized water and in 0.9% by weight sodium chloride (NaCl) solution. The sodium polyacrylate can absorb 146.2 grams (g) of deionized water per gram of SAP (g/g) at 0 psi, 103.8 g of deionized water per gram of polymer at 0.28 psi, and 34.3 g of deionized water per gram of polymer of 0.7 psi. In contrast, the same sodium polyacrylate is capable of absorbing only 43.5 g, 29.7 g, and 24.8 g of 0.9% aqueous NaCl at 0 psi, 0.28 psi, and 0.7 psi, respectively. The absorption capacity of SAPs for body fluids, such as urine or menses, therefore, is dramatically lower than for deionized water because such fluids contain electrolytes. This dramatic decrease in absorption is termed "salt poisoning."

The salt poisoning effect has been explained as follows. Water-absorption and water-retention characteristics of SAPs are attributed to the presence of ionizable functional groups in the polymer structure. The ionizable groups typically are carboxyl groups, a high proportion of which are in the salt form when the polymer is dry, and which undergo dissociation and salvation upon contact with water. In the dissociated state, the polymer chain contains a plurality of functional groups having the same electric charge and, thus, repel one another. This electronic repulsion leads to expansion of the polymer structure, which, in turn, permits further absorption of water molecules. Polymer expansion, however, is limited by the crosslinks in the polymer structure, which are present in a sufficient number to prevent solubilization of the polymer.

It is theorized that the presence of a significant concentration of electrolytes interferes with dissociation of the ionizable functional groups, and leads to the "salt poisoning" effect. Dissolved ions, such as sodium and chloride ions, therefore, have two effects on SAP gels. The ions screen the polymer charges and the ions eliminate the osmotic imbalance due to the presence of counter ions inside and outside of the gel. The dissolved ions, therefore, effectively convert an ionic gel into a nonionic gel, and swelling properties are lost.

The most commonly used SAP for absorbing electrolyte-containing liquids, such as urine, is neutralized polyacrylic acid, i.e., containing at least 50%, and up to 100%, neutralized carboxyl groups. Neutralized polyacrylic acid, however, is susceptible to salt poisoning. Therefore, to provide an SAP that is less susceptible to salt poisoning, either an SAP different from neutralized polyacrylic acid must be developed, or the neutralized polyacrylic acid must be modified or treated to at least partially overcome the salt poisoning effect.

The removal of ions from electrolyte-containing solutions is often accomplished using ion exchange resins. In this process, deionization is performed by contacting an electrolyte-containing solution with two different types of ion exchange resins, i.e., an anion exchange resin and a cation exchange resin. The most common deionization procedure uses an acid resin (i.e., cation exchange) and a base resin (i.e., anion exchange). The two-step reaction for deionization is illustrated with respect to the desalinization of water as follows:

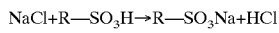

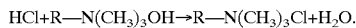

The acid resin (R—SO$_3$H) removes the sodium ion; and the base resin (R—N(CH$_3$)$_3$OH) removes the chloride ions. This ion exchange reaction, therefore, produces water as sodium chloride is adsorbed onto the resins. The resins used in ion exchange do not absorb significant amounts of water.

The most efficient ion exchange occurs when strong acid and strong base resins are employed. However, weak acid and weak base resins also can be used to deionize saline solutions. The efficiency of various combinations of acid and base exchange resins are as follows:

Strong acid—strong base (most efficient)

Weak acid—strong base

Strong acid—weak base

Weak acid—weak base (least efficient).

The weak acid/weak base resin combination requires that a "mixed bed" configuration be used to obtain deionization. The strong acid/strong base resin combination does not necessarily require a mixed bed configuration to deionize water. Deionization also can be achieved by sequentially passing the electrolyte-containing solution through a strong acid resin and strong base resin.

A "mixed bed" configuration of the prior art is a physical mixture of an acid ion exchange resin and a base ion exchange resin in an ion exchange column, as disclosed in Battaerd U.S. Pat. No. 3,716,481. Other patents directed to ion exchange resins having one ion exchange resin embedded in a second ion exchange resin are Hatch U.S. Pat. No. 3,957,698, Wade et al. U.S. Pat. No. 4,139,499, Eppinger et al. U.S. Pat. No. 4,229,545, and Pilkington U.S. Pat. No. 4,378,439. Composite ion exchange resins also are disclosed in Hatch U.S. Pat. Nos. 3,041,092 and 3,332,890, and Weiss U.S. Pat. No. 3,645,922.

The above patents are directed to nonswelling resins that can be used to remove ions from aqueous fluids, and thereby provide purified water. Ion exchange resins used for water purification must not absorb significant amounts of water because resin swelling resulting from absorption can lead to bursting of the ion exchange containment column.

Ion exchange resins or fibers also have been disclosed for use in absorbent personal care devices (e.g., diapers) to control the pH of fluids that reach the skin, as set forth in Berg et al. U.S. Pat. No. 4,685,909. The ion exchange resin is used in this application to reduce diaper rash, but the ion exchange resin is not significantly water absorbent and, therefore, does not improve the absorption and retention properties of the diaper.

Ion exchange resins having a composite particle containing acid and base ion exchange particles embedded together in a matrix resin, or having acid and base ion exchange particles adjacent to one another in a particle that is free of a matrix resin are disclosed in B. A. Bolto et al., *J. Polymer Sci.: Symposium No. 55*, John Wiley and Sons, Inc. (1976), pages 87–94. The Bolto et al. publication is directed to improving the reaction rates of ion exchange resins for water purification and does not utilize resins that absorb substantial amounts of water.

Other investigators have attempted to counteract the salt poisoning effect and thereby improve the performance of SAPs with respect to absorbing electrolyte-containing liquids, such as menses and urine. For example, Tanaka et al. U.S. Pat. No. 5,274,018 discloses an SAP composition comprising a swellable hydrophilic polymer, such as polyacrylic acid, and an amount of an ionizable surfactant sufficient to form at least a monolayer of surfactant on the polymer. In another embodiment, a cationic gel, such as a gel containing quaternized ammonium groups and in the hydroxide (i.e., OH) form, is admixed with an anionic gel (i.e., a polyacrylic acid) to remove electrolytes from the solution by ion exchange. Quaternized ammonium groups in the hydroxide form are very difficult and time-consuming to manufacture, thereby limiting the practical use of such cationic gels.

Wong U.S. Pat. No. 4,818,598 discloses the addition of a fibrous anion exchange material, such as DEAE (diethylaminoethyl) cellulose, to a hydrogel, such as a polyacrylate, to improve absorption properties. The ion exchange resin "pretreats" the saline solution (e.g., urine) as the solution flows through an absorbent structure (e.g., a diaper). This pretreatment removes a portion of the salt from the saline. The conventional SAP present in the absorbent structure then absorbs the treated saline more efficiently than untreated saline. The ion exchange resin, per se, does not absorb the saline solution, but merely helps overcome the "salt poisoning" effect.

WO 96/17681 discloses admixing discrete anionic SAP particles, such as polyacrylic acid, with discrete polysaccharide-based cationic SAP particles to overcome the salt poisoning effect. Similarly, WO 96/15163 discloses combining a cationic SAP having at least 20% of the functional groups in a basic (i.e., OH) form with a cationic exchange resin, i.e., a nonswelling ion exchange resin, having at least 50% of the functional groups in the acid form. WO 96/15180 discloses an absorbent material comprising an anionic SAP, e.g., a polyacrylic acid and an anion exchange resin, i.e., a nonswelling ion exchange resin.

Water-absorbing resins, particularly superabsorbent polymers, have been in use in disposable, absorbent fibrous articles, such as diapers and bandages for many years. These superabsorbent polymers have been used together with a batt of absorbent fibers, such as cellulose fibers, used to absorb and hold the liquid within the product, and for faster liquid uptake during the slower absorption of the liquid by an adjacent superabsorbent polymer. The most common absorbent batt used in the diaper art is manufactured from fluffed wood pulp fibers, as disclosed in U.S. Pat. No. 2,788,003, hereby incorporated by reference. A densified paper-like surface layer also has been used in conjunction with an absorbent batt to improve "wicking" of the liquid to the absorbent batt, as disclosed in U.S. Pat. Nos. 3,612,055 and 3,938,522. The absorbent structure of the present invention is useful with or without absorbent fibers and/or wicking layers disclosed in the above-identified patents.

Others have attempted to manufacture a continuous roll of woven or non-woven fibrous material that contains a high percentage, e.g., 50–80% by weight, of a particulate superabsorbent polymer, such as sodium polyacrylate. Examples of fibrous substrates impregnated with superabsorbent polymer are found in U.S. Pat. Nos. 5,614,269; 5,980,996; and 5,756,159 wherein a fibrous substrate is impregnated with the superabsorbent polymer by impregnation with the monomer and subsequent polymerization by contact with UV light for polymerization in situ while in contact with the fibrous substrate.

Other patents, including U.S. Pat. Nos. 5,607,550 and 5,997,690 teach the continuous manufacture of a fibrous substrate containing more than about 50% superabsorbent particles (50–60%) by the wet, papermaking process. In accordance with the wet process. The raw material, including fibers and superabsorbent particles, are mixed with copious quantities of water, or other liquid medium capable of swelling the superabsorbent particles, and deposited onto a water-pervious support member, generally a Fourdinier wire, where much of the water is removed leaving a wet mass of fiber and superabsorbent polymer particles. The wet mat is transferred from the pervious support member and consolidated under heat and pressure to form the fibrous substrate having the superabsorbent particles distributed throughout. As disclosed in U.S. Pat. No. 5,997,690, sufficient absorbency performance requires at least about 50% by weight superabsorbent particles based on the total weight of the absorbent article. The most difficult problem encountered in attempting to continuously manufacture the sheet material containing a relatively high percentage of superabsorbent particles is in achieving structural integrity of the article both during and after manufacture without significant loss (shakeout) of superabsorbent particles.

Another principal process for continuously making a consolidated sheet of material is a "dry" process. In a dry process, filler material, such as cellulosic fibers, is coated with a resin binder in a gaseous stream, or by mechanical means. For example, the fibers supplied from a fiberizing apparatus (e.g., a pressurized refiner) may be coated with a thermosetting synthetic resin, such as a phenol-formaldehyde resin, in a blowline blending procedure, wherein the resin is blended with the fiber with the aid of air turbulence. Thereafter, the resin-coated fibers from the blowline are subjected to pre-press drying, for example, in a tube-like dryer, and then are randomly formed into a mat by air conveying the fibers onto a support member (e.g., a forming wire). The formed mat, preferably having a moisture content of less than about 10 wt. %, is then pressed under heat and pressure in a press between a pair of heated platens to cure the thermosetting resin and to compress the mat into an integral consolidated structure. The consolidated structure may be embossed on an outer surface by texturing one of the press platens to achieve a desired embossed design in the outer surface of the product during consolidation.

Another process for continuously manufacturing a consolidated sheet of material is a wet-dry process, wherein resin-blended fiber from the blow-line is mixed with water as the conveying medium and is formed into a mat as a wet slurry on a water-pervious support member where water is removed by mechanical means to a moisture content of about 60% or less. The formed mat then is mechanically conveyed through a multi-deck air dryer in which the moisture content is further reduced to about 10% or less. The mat is then pressed under heat and pressure similar to the above-described "dry" process.

In accordance with the principles of the present invention, it has been found, unexpectedly, that a continuous sheet having a combination of acidic and basic water-absorbing resin particles that are essentially unneutralized (0% to about 25% neutralized) can be continuously manufactured on conventional papermaking apparatus, using any of the above-described wet, dry, or wet-dry processes to manufacture a water-absorbent sheet-like substrate containing 50%–100% by weight of the combination of acidic and basic water-absorbent particles, added to form the sheet material articles of the present invention as separate acidic and basic resin particles, or as multicomponent particles containing both the acidic and basic resins. The sheet materials can be manufactured having new and unexpected structural integrity with little or no shakeout or loss of superabsorbent particles during or after manufacture.

The sheet materials of the present invention exhibit exceptional water absorption and retention properties, especially with respect to electrolyte-containing liquids, and thereby overcome the salt poisoning effect. In addition, the sheet materials have an ability to absorb liquids quickly, demonstrate good fluid permeability and conductivity into and through the SAP particles, and have a high gel strength such that the hydrogel formed from the SAP particles, upon hydration, resists deformation under an applied stress or pressure, when used alone or in a mixture with other water-absorbing resins.

SUMMARY OF THE INVENTION

In brief, the present invention is directed to the manufacture of a continuous sheet having a combination of acidic and basic water-absorbing resin particles that are essentially not neutralized (0% to about 25% neutralized), can be continuously manufactured on conventional papermaking apparatus, using a wet, dry, or wet-dry process to manufacture a water-absorbent sheet-like substrate containing 50%–100% by weight of the combination of acidic and basic water-absorbent particles. The acidic and basic essentially unneutralized resins can be contained in the sheet material articles of the present invention as separate acidic and basic resin particles, or as multicomponent particles containing both the acidic and basic resins. The sheet materials can be manufactured having new and unexpected structural integrity; with little or no shakeout or loss of superabsorbent particles during or after manufacture; and exhibit exceptional water absorption and retention properties, especially with respect to electrolyte-containing liquids, and thereby overcome the salt poisoning effect. The sheet materials have an ability to absorb liquids quickly, demonstrate good fluid permeability and conductivity into and through the resin particles, and have a high gel strength such that the hydrogel formed from the SAP particles, upon hydration, resists deformation under an applied stress or pressure, when used alone or in a mixture with other water-absorbing resins.

BRIEF DESCRIPTION OF THE DRAWINGS

FIGS. 3A and 3B are schematic diagrams of a water-absorbing particle having a core microdomain of a first resin surrounded by a layer of a second resin;

FIGS. 4A–D are schematic diagrams of water-absorbing particles having a microdomain of a first resin in contact with a microdomain of a second resin;

FIGS. 5A and 5B are schematic diagrams of a water-absorbing particle having an interpenetrating network of a first resin and a second resin;

DETAILED DESCRIPTION OF THE PREFERRED EMBODIMENTS

Figure 1:
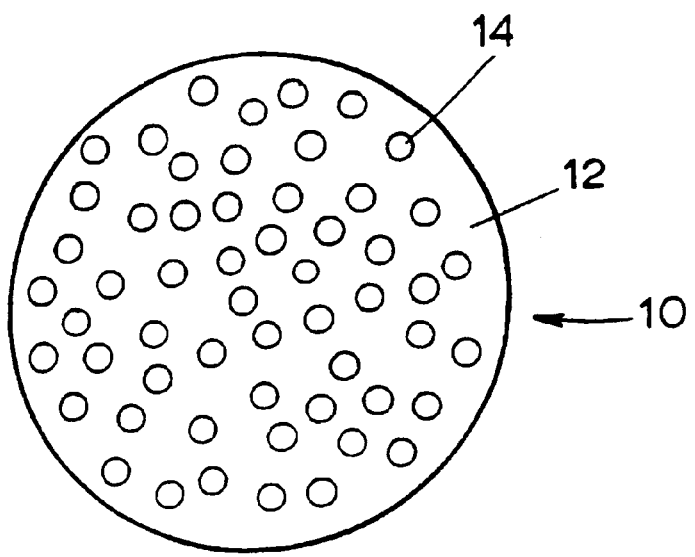
FIG. 1 is a schematic diagram of a water-absorbing particle containing microdomains of a first resin dispersed in a continuous phase of a second resin.

In accordance with the present invention, a sheet of material is continuously manufactured containing a combination of an essentially unneutralized acidic water-absorbing resin and an essentially unneutralized basic water-absorbing resin (bicomponent SAP materials) which may be incorporated into the sheet material as separate components; or as multicomponent SAP particles, wherein each particle contains at least one microdomain of the acidic water-absorbing resin and at least one microdomain of the basic water-absorbing resin. Surprisingly, it has been found that using typical papermaking machinery for manufacture of the superabsorbent polymer sheet materials of the present invention, using the wet process, dry process, or wet-dry process apparatus for manufacture of the sheet materials, new and unexpected structural integrity is achieved in the articles containing 40%–100%, preferably 50%–100%, by weight superabsorbent particles, and 0%–60%, preferably 0%–50% by weight of other fibers, adhesives, or fillers, such as cellulosic or wood fluff fibers, thermoplastic fibers, adhesives, fillers, and other additives. The superabsorbent polymer sheet materials are useful as diaper cores and in other catamenial devices; aqueous ion-exchange materials for separation or removal of unwanted dissolved ions; and other hygienic devices, absorptive pads, and wipes.

The two types of superabsorbent particles incorporated into the superabsorbent sheet material articles of the present invention may be incorporated separately; or as multicomponent SAP particles, each containing at least one microdomain of an acidic water-absorbing resin and at least one microdomain of a basic water-absorbing resin. Both the acidic and basic water-absorbing resins, whether added as single component particles or as multicomponent particles, are uncharged, slightly cross-linked polymers that are unneutralized, or neutralized to a low degree, such that the acidic and basic resins, when wetted, achieve ion exchange between the two resins for particle neutralization of each other. Both the acidic and basic water-absorbing resins are capable of swelling and absorbing aqueous media.

When contacted with an aqueous fluid, like urine, the two uncharged polymers are at least partially neutralized, up to the extent that they are not already neutralized, to form a superabsorbent material. Neither polymer in its uncharged form behaves as an SAP by itself when contacted with water. The bicomponent superabsorbent material embodiment of the present invention, therefore, comprises a sheet material that includes two distinctly different resin particles, one acidic and one basic, which are capable of acting as an absorbent material when both are included in the sheet material in their polyelectrolyte form. The multicomponent superabsorbent material embodiment of the present invention provides both the acidic and basic resins in a single particle, each in separate microdomains in contact with each other, or in close enough proximity for ion exchange with ions contained in the aqueous material contacted, when wetted.

The preferred water-absorbent acidic and basic resin particles used as, or incorporated into, the sheet materials of the present invention are formed as multicomponent SAP particles wherein the particles include both the acidic resin and the basic resin in the particles. However, as discussed previously, the components of the multicomponent SAP particles, described in more detail hereinafter, can be added to the sheet material separately so long as the acidic and basic particles are in contact, or sufficiently close in proximity, within the sheet material, to interact via ion-exchange to at least partially neutralize each other, when contacted with water.

The multicomponent SAP particles contain at least one discrete microdomain of at least one acidic water-absorbing resin in contact with, or in close proximity to, at least one microdomain of at least one basic water-absorbing resin. The multicomponent SAP particles can contain a plurality of microdomains of the acidic water-absorbing resin and/or the basic water-absorbing resin dispersed throughout the particle. The acidic resin can be a strong or a weak acidic resin. Similarly, the basic resin can be a strong or a weak basic resin. A preferred SAP contains one or more microdomains of at least one weak acidic resin and one or more microdomains of at least one weak basic resin. The properties demonstrated by such preferred multicomponent SAP particles are unexpected because, in ion exchange applications, the combination of a weak acid and a weak base is the least effective of any combination of a strong or weak acid ion exchange resin with a strong or weak basic ion exchange resin.

The multicomponent SAP particles have a high absorption rate, have good permeability and gel strength, overcome the above-described salt poisoning effect, and demonstrate an improved ability to absorb and retain electrolyte-containing liquids, such as saline, blood, urine, and menses even when manufactured continuously containing 0–50% fiber, with or without a synthetic binder or thermal bonding thermoplastic fibers, resulting in unexpected structural integrity. The multicomponent SAP particles contain discrete microdomains of acidic and basic resin, and during hydration, the particles resist coalescence but remain fluid permeable.

The multicomponent SAP particles are produced by any method that positions a microdomain of an acidic water-absorbing resin in contact with, or in close proximity to, a microdomain of a basic water-absorbing resin to provide a discrete particle. In one embodiment, the multicomponent SAP particles are produced by coextruding an acidic water-absorbing hydrogel and a basic water-absorbing hydrogel to provide multicomponent SAP particles having a plurality of discrete microdomains of an acidic resin and a basic resin dispersed throughout the particle. Such multicomponent SAP particles demonstrate improved absorption and retention properties, and permeability through and between particles compared to typical SAP acrylates, and are far superior in providing structural integrity of the continuously manufactured sheets of material, with far less shakeout of SAP particles during manufacture and handling.

In another embodiment, the multicomponent SAP particles can be prepared by admixing dry particles of a basic resin with a hydrogel of an acidic resin, then extruding the resulting mixture to form multicomponent SAP particles having microdomains of a basic resin dispersed throughout a continuous phase of an acidic resin. Alternatively, dry acidic resin particles can be admixed with a basic resin hydrogel, followed by extruding the resulting mixture to form multicomponent SAP particles having microdomains of an acidic resin dispersed in a continuous phase of a basic resin.

In addition, a multicomponent SAP particle containing microdomains of an acidic resin and a basic resin dispersed in a continuous phase of a matrix resin can be prepared by adding dry particles of the acidic resin and dry particles of the basic resin to a hydrogel of the matrix hydrogel, then extruding. Other forms of the present multicomponent SAP particles, such as agglomerated particles, interpenetrating polymer network forms, laminar forms, and concentric sphere forms, also demonstrate improved fluid absorption and retention properties.

The acidic and basic resins are lightly crosslinked, such as with a suitable polyfunctional vinyl polymer. In preferred embodiments, the acidic resin, the basic resin, and/or the entire multicomponent SAP particle are surface treated, e.g., surface crosslinked, interfacially cured, or annealed to further improve water absorption and retention properties, especially under a load.

An example of a weak acid resin is polyacrylic acid having 0% to 25% neutralized carboxylic acid groups (i.e., DN=0 to DN=25). Examples of weak basic water-absorbing resins are a poly(vinylamine), a polyethylenimine, and a poly(dialkylaminoalkyl (meth)acrylamide) prepared from a monomer either having the general structure formula (I)

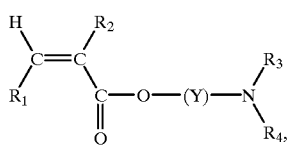

or the ester analog of (I) having the general structure formula (II)

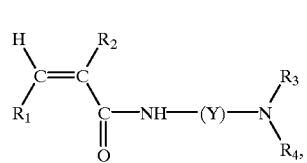

wherein $R_1$ and $R_2$, independently, are selected from the group consisting of hydrogen and methyl, Y is a divalent straight chain or branched organic radical having 1 to 8 carbon atoms, and $R_3$ and $R_4$, independently, are alkyl radicals having 1 to 4 carbon atoms. Examples of a strong basic water-absorbing resin are poly(vinylguanidine) and poly(allylguanidine).

In accordance with another aspect of the present invention, the multicomponent SAP particles can be combined with particles of a another, single component water-absorbing resin selected from the group consisting of an acidic water-absorbing resin, a basic water-absorbing resin, and a mixture thereof. The combination contains about 10% to about 90%, by weight, multicomponent SAP particles and about 10% to about 90%, by weight, particles of the single component water-absorbing resin.

Each multicomponent SAP particle included within the sheet material of the present invention contains at least one acidic water-absorbing resin and at least one basic water-absorbing resin. In one embodiment, the multicomponent SAP particles consist essentially of acidic resins and basic resins, and contain microdomains of the acidic and/or basic resins. In another embodiment, microdomains of the acidic and basic resins, or the separate acidic resin particles and basis resin particles, are dispersed in an absorbent matrix resin.

The multicomponent SAP particles included in the sheet materials of the present invention are not limited to a particular structure or shape. However, it is important that the multicomponent SAP particles contain at least one microdomain of an acidic water-absorbing resin and at least one microdomain of a basic water-absorbing resin in close proximity to one another. Improved water absorption and retention, and improved fluid permeability through and between multicomponent SAP particles, are observed as long as the acidic resin microdomain and the basic resin microdomain are in close proximity within the particle. In a preferred embodiment, the microdomains of acidic and basic resin are in contact.

In some embodiments, an idealized multicomponent SAP particle of the present invention is analogous to a liquid emulsion wherein small droplets of a first liquid, i.e., the dispersed phase, are dispersed in a second liquid, i.e., the continuous phase. The first and second liquids are immiscible, and the first liquid, therefore, is homogeneously dispersed in the second liquid. The first liquid can be water or oil based, and conversely, the second liquid is oil or water based, respectively.

Therefore, in one embodiment, the multicomponent SAP particles can be envisioned as one or more microdomains of an acidic resin dispersed in a continuous phase of a basic resin, or as one or more microdomains of a basic resin dispersed in a continuous acid resin. These idealized multicomponent SAP particles are illustrated in FIG. 1 showing an SAP particle 10 having discrete microdomains 14 of a dispersed resin in a continuous phase of a second resin 12. If microdomains 14 comprise an acidic resin, then continuous phase 12 comprises a basic resin. Conversely, if microdomains 14 comprise a basic resin, then continuous phase 12 is an acidic resin.

Figure 2:
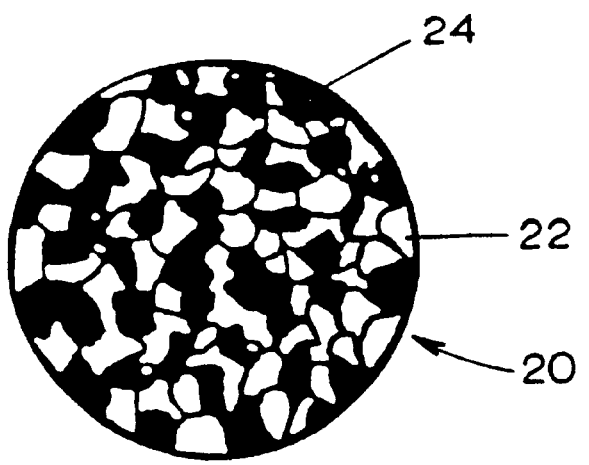
FIG. 2 is a schematic diagram of a water-absorbing particle containing microdomains of a first resin and microdomains of a second resin dispersed throughout the particle.

In another embodiment, the multicomponent SAP particles are envisioned as microdomains of an acidic resin and microdomains of a basic resin dispersed throughout each particle, without a continuous phase. This embodiment is illustrated in FIG. 2, showing an idealized multicomponent SAP particle having a plurality of microdomains of an acidic resin 22 and a plurality of microdomains of a basic resin 24 dispersed throughout particle 20.

In yet another embodiment, microdomains of the acidic and basic resins are dispersed throughout a continuous phase comprising a matrix resin. This embodiment also is illustrated in FIG. 1 wherein multicomponent SAP particle 10 contains one or more microdomains 14, each an acidic resin or a basic resin, dispersed in a continuous phase 12 of a matrix resin.

It should be understood that the microdomains within each particle can be of regular or irregular shape, and that the microdomains can be dispersed homogeneously or nonhomogeneously throughout each particle. Accordingly, another embodiment of the SAP particles is illustrated in FIG. 3A, showing an idealized multicomponent particle 30 having a core 32 of an acidic water-absorbing resin surrounded by a shell 34 of a basic water-absorbing resin. Conversely, core 32 can comprise a basic resin, and shell 34 can comprise an acidic resin.

FIG. 3B illustrates a similar embodiment having a core and concentric shells that alternate between shells of acidic resin and basic resin. In one embodiment, core 42 and shell 46 comprise an acidic water-absorbing resin, and shell 44 comprises a basic water-absorbing resin. Other embodiments include: core 42 and shell 46 comprising a basic resin and shell 44 comprising an acidic resin, or core 42 comprising a matrix resin and shells 44 and 46 comprising an acidic resin and a basic resin in alternating shells. Other configurations are apparent to persons skilled in the art, such as increasing the number of shells around the core.

FIGS. 4A and 4B illustrate embodiments of the multicomponent SAP particles wherein one microdomain of an acidic water-absorbing resin (i.e., 52 or 62) is in contact with one microdomain of a basic water-absorbing resin (i.e., 54 or 64) to provide a multicomponent SAP particle (i.e., 50 or 60). In these embodiments, the microdomains are dispersed nonhomogeneously throughout the particle. The embodiments illustrated in FIG. 4 extend to SAP particles having more than one microdomain of each of the acidic resin and the basic resin, as illustrated in FIGS. 4C and 4D, wherein multicomponent SAP particles 70 and 80 contain alternating zones of acidic water-absorbing resin (e.g., 72 or 82) and basic water-absorbing resin (e.g., 74 or 84). Particles 70 and 80 also can contain one or more layers 72, 74, 82, or 84 comprising a matrix resin.

In another embodiment, the multicomponent SAP particle comprises an interpenetrating polymer network (IPN), as illustrated in FIG. 5. An IPN is a material containing two polymers, each in network form. In an IPN, two polymers are synthesized and/or crosslinked in the presence of one another, and polymerization can be sequential or simultaneous. Preparation of a sequential IPN begins with the synthesis of a first crosslinked polymer. Then, monomers comprising a second polymer, a crosslinker, and initiator are swollen into the first polymer, and polymerized and crosslinked in situ. For example, a crosslinked poly(acrylic acid) network can be infused with solution containing a poly(vinylamine) and a crosslinker.

Simultaneous IPNs are prepared using a solution containing monomers of both polymers and their respective crosslinkers, which then are polymerized simultaneously by noninterfering modes, such as stepwise or chain polymerizations. A third method of synthesizing IPNs utilizes two lattices of linear polymers, mixing and coagulating the lattices, and crosslinking the two components simultaneously. Persons skilled in the art are aware of other ways that an IPN can be prepared, each yielding a particular topology.

In most IPNs, the polymer phases separate to form distinct zones of the first polymer and distinct zones of the second polymer. In the remaining IPNs, the first and second polymers remain "soluble" in one another. Both forms of IPN have microdomains, and are multicomponent SAPs of the present invention.

FIGS. 5A and 5B illustrate IPN systems. FIG. 5A illustrates an IPN made by sequentially synthesizing the first and second polymers. FIG. 5B illustrates an IPN made by simultaneously polymerizing the first and second polymers. In FIGS. 5A and 5B, the solid lines represent the first polymer (e.g., the acidic polymer) and the lightly dotted lines represent the second polymer (e.g., the basic polymer). The heavy dots represent crosslinking sites.

In another embodiment, the multicomponent SAP particles are agglomerated particles prepared from fine particles of an acidic water-absorbing resin and fine particles of a basic water-absorbing resin. Typically, a fine resin particle has a diameter of less than about 200 microns ($\mu$), such as about 0.01 to about 180$\mu$. The agglomerated multicomponent SAP particles are similar in structure to the particle depicted in FIG. 2. With respect to the agglomerated SAP particles, it is important that the particles have sufficient dry agglomeration (i.e., in the dry state) and wet agglomeration (i.e., in the hydrogel state) to retain single particle properties, i.e., the particles do not disintegrate into their constituent fine particles of acidic resin and basic resin.

In particular, the agglomerated particles have sufficient dry agglomeration to withstand fracturing. The dry agglomerated particles typically have an elastic character and, therefore, are not friable. The agglomerated particles also have sufficient wet strength to exhibit a property termed "wet agglomeration." Wet agglomeration is defined as the ability of an agglomerated multicomponent SAP particle to retain its single particle nature upon hydration, i.e., a lack of deagglomeration upon hydration. Wet agglomeration is determined by positioning fifty agglomerated SAP particles on a watch glass and hydrating the particles with 20 times their weight of a 1% (by weight) sodium chloride solution (i.e., 1% saline). The particles are spaced sufficiently apart such that they do not contact one another after absorbing the saline and swelling. The multicomponent SAP particles are allowed to absorb the saline solution for one hour, then the number of SAP particles is recounted under a microscope. The multicomponent SAP particles pass the wet agglomeration test if no more than about 53 hydrated particles are counted.

The multicomponent SAP particles therefore comprise an acidic resin and a basic resin in a weight ratio of about 90:10 to about 10:90, and preferably about 20:80 to about 80:20. To achieve the full advantage of the present invention, the weight ratio of acidic resin to basic resin in a multicomponent SAP particle is about 30:70 to about 70:30. The acidic and basic resins can be distributed homogeneously or nonhomogeneously throughout the SAP particle.

The multicomponent SAP particles contain at least about 50%, and preferably at least about 70%, by weight of acidic resin plus basic resin. To achieve the full advantage of the present invention, a multicomponent SAP particle contains about 80% to 100% by weight of the acidic resin plus basic resin. Components of the present SAP particles, other than the acidic and basic resin, typically, are matrix resins or other minor optional ingredients.

The multicomponent SAP particles can be in any form, either regular or irregular, such as granules, fibers, beads, powders, flakes, or foams, or any other desired shape, such as a sheet of the multicomponent SAP. In embodiments wherein the multicomponent SAP is prepared using an extrusion step, the shape of the SAP is determined by the shape of the extrusion die. The shape of the multicomponent SAP particles also can be determined by other physical operations, such as milling or by the method of preparing the particles, such as agglomeration.

In one preferred embodiment, the multicomponent SAP particles are in the form of a granule or a bead, having a particle size of about 10 to about 10,000 microns ($\mu$m), and preferably about 100 to about 1,000 $\mu$m. To achieve the full advantage of the present invention, the multicomponent SAP particles have a particle size of about 150 to about 800 $\mu$m.

A microdomain is defined as a volume of an acidic resin or a basic resin that is present in a multicomponent SAP particle. Because each multicomponent SAP particle contains at least one microdomain of an acidic resin, and at least one microdomain of a basic resin, a microdomain has a volume that is less than the volume of the multicomponent SAP particle. A microdomain, therefore, can be as large as about 90% of the volume of multicomponent SAP particles.

Typically, a microdomain has a diameter of about 750 $\mu$m or less, and preferably about 100 $\mu$m or less. To achieve the full advantage of the present invention, a microdomain has a diameter of about 20 $\mu$m or less. The multicomponent SAP particles also contain microdomains that have submicron diameters, e.g., microdomain diameters of less than 1 $\mu$m, preferably less than 0.1 $\mu$m, to about 0.01 $\mu$m.

In another preferred embodiment, the multicomponent SAP particles are in the shape of a fiber, i.e., an elongated, acicular SAP particle. The fiber can be in the shape of a cylinder, for example, having a minor dimension (i.e., diameter) and a major dimension (i.e., length). The fiber also can be in the form of a long filament that can be woven. Such filament-like fibers have a weight of below about 80 decitex, and preferably below about 70 decitex, per filament, for example, about 2 to about 60 decitex per filament. Tex is the weight in grams per one kilometer of fiber. One tex equals 10 decitex. For comparison, poly(acrylic acid) is about 1 decitex, and poly(vinylamine) is about 6 decitex.

Cylindrical multicomponent SAP fibers have a minor dimension (i.e., diameter of the fiber) less than about 1 mm, usually less than about 500 $\mu$m, and preferably less than 250 $\mu$m, down to about 50 $\mu$m. The cylindrical SAP fibers can have a relatively short major dimension, for example, about 1 mm, e.g., in a fibrid, lamella, or flake-shaped article, but generally the fiber has a length of about 3 to about 100 mm. The filament-like fibers have a ratio of major dimension to minor dimension of at least 500 to 1, and preferably at least 1000 to 1, for example, up to and greater than 10,000 to 1.

Each multicomponent SAP particle contains one or more microdomains of an acidic water-absorbing resin and one or more microdomains of a basic water-absorbing resin, either in contact or in close proximity to one another. As illustrated hereafter, the microdomain structure of the multicomponent SAP particles provides improved fluid absorption (both in amount of fluid absorbed and retained, and rate of absorption) compared to an SAP comprising a simple mixture of discrete acidic SAP resin particles and discrete basic SAP resin particles. In accordance with another important feature of the present invention, the multicomponent SAP particles also demonstrated improved permeability, both through an individual particle and between particles. The present SAP particles, therefore, have an improved ability to rapidly absorb a fluid, even in "gush" situations, for example, when used in diapers to absorb urine, and even totally without wicking fibers, such as cellulosic fibers.

The features of good permeability, absorption and retention properties, especially of electrolyte-containing liquids, demonstrated by the multicomponent SAP particles, are important when the particles are adhered together, with or without cellulosic or thermoplastic fibers, and with or without an adhesive, thermoplastic binder to achieve rapid water uptake and good absorption capacity. These improved properties are attributed, in part, to the fact that electrolyte removal from the liquid is facilitated by contacting a single particle (which, in effect, performs an essentially simultaneous deionization of the liquid), as opposed to the liquid having to contact individual acidic and basic particles (which, in effect, performs a sequential two-step deionization). However, as described, the individual components (acidic and basic water-absorbing resins) of the multicomponent SAP particles can be added separately to the sheet material, as a substitute for, or in addition to, the multicomponent particles, with excellent absorption results and sheet material integrity.

If the blend of acidic resin particles and basic resin particles is used, the particles preferably have a relatively small particle size, e.g., 10 to 500 $\mu$m. A small particle size is preferred to obtain desirable desalination kinetics, because the electrolyte is removed in a stepwise manner, with the acidic resin removing the cation and the basic resin removing the anion. The electrolyte-containing fluid, therefore, must contact two particles for desalination, and this process is facilitated by small particle sized SAPs. Small particles, however, have the effect of reducing flow of the fluid through and between SAP particles, i.e., permeability is reduced and a longer time is required to absorb the fluid.

A single multicomponent SAP particle simultaneously desalinates an electrolyte-containing liquid. Desalination is essentially independent of particle size. Accordingly, the present multicomponent SAP particles can be of a larger size. These features allow for improved liquid permeability through and between the SAP particles, and results in a more rapid absorption of the electrolyte-containing liquid in the sheet material.

The following schematic reactions illustrate the reactions which occur to deionize, e.g., desalinate, an aqueous saline solution, and that are performed essentially simultaneously in a single microcomposite SAP particle, and are performed step-wise in a simple mixture of acidic and basic resins:

$$R\text{—}CO_2H + NaCl \rightarrow R\text{—}CO_2^- Na^+ + HCl$$

(acidic resin)

$$R\text{—}NH_2 + HCl \rightarrow R\text{—}NH_3^+ Cl^-$$

(basic resin).

The multicomponent SAP particle can be in a form wherein a microdomain of an acidic water-absorbing resin is in contact with a microdomain of a basic water-absorbing resin. In another embodiment, the SAP particles can be in a form wherein at least one microdomain of an acidic water-absorbing resin is dispersed in a continuous phase of a basic water-absorbing resin. Alternatively, the multicomponent SAP can be in a form wherein at least one microdomain of a basic resin is dispersed in a continuous phase of an acidic resin. In another embodiment, at least one microdomain of one or more acidic resin and at least one microdomain of one or more basic resin comprise the entire SAP particle, and neither type of resin is considered the dispersed or the continuous phase. In yet another embodiment, at least one microdomain of an acidic resin and at least one microdomain of a basic resin are dispersed in a matrix resin.

An acidic water-absorbing resin present in a multicomponent SAP particle can be either a strong or a weak acidic water-absorbing resin. The acidic water-absorbing resin can be a single resin, or a mixture of resins. The acidic resin can be a homopolymer or a copolymer. The identity of the acidic water-absorbing resin is not limited as long as the resin is capable of swelling and absorbing at least ten times its weight in water, when in a neutralized form. The acidic resin is present in its acidic form, i.e., about 75% to 100% of the acidic moieties are present in the free acid form. As illustrated hereafter, although the free acid form of an acidic water-absorbing resin is generally a poor water absorbent, the combination of an acidic resin and a basic resin in a present multicomponent SAP particle provides excellent water absorption and retention properties.

The acidic water-absorbing resin typically is a lightly crosslinked acrylic-type resin, such as lightly crosslinked polyacrylic acid. The lightly crosslinked acidic resin typically is prepared by polymerizing an acidic monomer containing an acyl moiety, e.g., acrylic acid, or a moiety capable of providing an acid group, i.e., acrylonitrile, in the presence of a crosslinker, i.e., a polyfunctional organic compound. The acidic resin can contain other copolymerizable units, i.e., other monoethylenically unsaturated comonomers, well known in the art, as long as the polymer is substantially, i.e., at least 10%, and preferably at least 25%, acidic monomer units. To achieve the full advantage of the present invention, the acidic resin contains at least 50%, and more preferably, at least 75%, and up to 100%, acidic monomer units. The other copolymerizable units can, for example, help improve the hydrophilicity of the polymer.

Ethylenically unsaturated carboxylic acid and carboxylic acid anhydride monomers useful in the acidic water-absorbing resin include acrylic acid, methacrylic acid, ethacrylic acid, α-chloroacrylic acid, α-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-stearylacrylic acid, itaconic acid, citraconic acid, mesaconic acid, glutaconic acid, aconitic acid, maleic acid, furmaric acid, tricarboxyethylene, and maleic anhydride.

Ethylenically unsaturated sulfonic acid monomers include aliphatic or aromatic vinyl sulfonic acids, such as vinylsulfonic acid, allyl sulfonic acid, vinyl toluene sulfonic acid, styrene sulfonic acid, acrylic and methacrylic sulfonic acids, such as sulfoethyl acrylate, sulfoethyl methacrylate, sulfopropyl acrylate, sulfopropyl methacrylate, 2-hydroxy-3-methacryloxypropyl sulfonic acid, and 2-acrylamide-2-methylpropane sulfonic acid.

Polymerization of acidic monomers, and copolymerizable monomers, if present, most commonly is performed by free radical processes in the presence of a polyfunctional organic compound. The acidic resins are crosslinked to a sufficient extent such that the polymer is water insoluble. Crosslinking renders the acidic resins substantially water insoluble, and, in part, serves to determine the absorption capacity of the resins. For use in absorption applications, an acidic resin is lightly crosslinked, i.e., has a crosslinking density of less than about 20%, preferably less than about 10%, and most preferably about 0.01% to about 7%.

A crosslinking agent most preferably is used in an amount of less than about 7 wt %, and typically about 0.1 wt % to about 5 wt %, based on the total weight of monomers. Examples of crosslinking polyvinyl monomers include, but are not limited to, polyacrylic (or polymethacrylic) acid esters represented by the following formula (III); and bisacrylamides, represented by the following formula (IV).

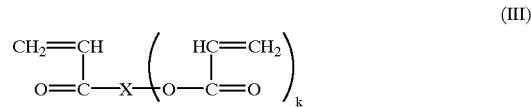

wherein X is ethylene, propylene, trimethylene, cyclohexyl, hexamethylene, 2-hydroxypropylene, —(CH$_2$CH$_2$O)$_n$CH$_2$CH$_2$—, or

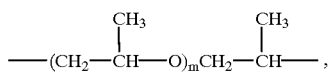

n and m are each an integer 5 to 40, and k is 1 or 2;

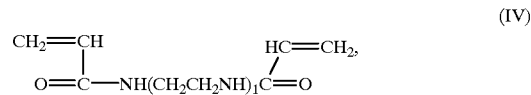

wherein l is 2 or 3.

The compounds of formula (III) are prepared by reacting polyols, such as ethylene glycol, propylene glycol, trimethylolpropane, 1,6-hexanediol, glycerin, pentaerythritol, polyethylene glycol, or polypropylene glycol, with acrylic acid or methacrylic acid. The compounds of formula (IV) are obtained by reacting polyalkylene polyamines, such as diethylenetriamine and triethylenetetramine, with acrylic acid.

Specific crosslinking monomers include, but are not limited to, 1,4-butanediol diacrylate, 1,4-butanediol dimethacrylate, 1,3-butylene glycol diacrylate, 1,3-butylene glycol dimethacrylate, diethylene glycol diacrylate, diethylene glycol dimethacrylate, ethoxylated bisphenol A diacrylate, ethoxylated bisphenol A dimethacrylate, ethylene glycol dimethacrylate, 1,6-hexanediol diacrylate, 1,6-hexanediol dimethacrylate, neopentyl glycol dimethacrylate, polyethylene glycol diacrylate, polyethylene glycol dimethacrylate, triethylene glycol diacrylate, triethylene glycol dimethacrylate, tripropylene glycol diacrylate, tetraethylene glycol diacrylate, tetraethylene glycol dimethacrylate, dipentaerythritol pentaacrylate, pentaerythritol tetraacrylate, pentaerythritol triacrylate, trimethylolpropane triacrylate, trimethylolpropane trimethacrylate, tris(2-hydroxyethyl)isocyanurate triacrylate, tris(2-hydroxyethyl)isocyanurate trimethacrylate, divinyl esters of a polycarboxylic acid, diallyl esters of a polycarboxylic acid, triallyl terephthalate, diallyl maleate, diallyl fumarate, hexamethylenebismaleimide, trivinyl trimellitate, divinyl adipate, diallyl succinate, a divinyl ether of ethylene glycol, cyclopentadiene diacrylate, tetraallyl ammonium halides, or mixtures thereof. Compounds such as divinylbenzene and divinyl ether also can be used. Especially preferred crosslinking agents are N,N'-methylenebisacrylamide, N,N'-methylene-bismethacrylamide, ethylene glycol dimethacrylate, and trimethylolpropane triacrylate.

The acidic resin, either strongly acidic or weakly acidic, can be any resin that acts as an SAP in its neutralized form. The acidic resins typically contain a plurality of carboxylic acid, sulfonic acid, phosphonic acid, phosphoric acid, and/or sulfuric acid moieties. Examples of acidic resins include, but are not limited to, polyacrylic acid, hydrolyzed starch-acrylonitrile graft copolymers, starch-acrylic acid graft copolymers, saponified vinyl acetate-acrylic ester copolymers, hydrolyzed acrylonitrile copolymers, hydrolyzed acrylamide copolymers, ethylene-maleic anhydride copolymers, isobutylene-maleic anhydride copolymers, poly(vinylsulfonic acid), poly(vinylphosphonic acid), poly(vinylphosphoric acid), poly(vinylsulfuric acid), sulfonated polystyrene, poly(aspartic acid), poly(lactic acid), and mixtures thereof. The preferred acidic resins are the polyacrylic acids.

The multicomponent SAPs can contain individual microdomains that: (a) contain a single acidic resin or (b) contain more than one, i.e., a mixture, of acidic resins. The multicomponent SAPs also can contain microdomains wherein, for the acidic component, a portion of the acidic microdomains comprise a first acidic resin or acidic resin mixture, and the remaining portion comprises a second acidic resin or acidic resin mixture.

Analogous to the acidic resin, the basic water-absorbing resin in the present SAP particles can be a strong or weak basic water-absorbing resins. The basic water-absorbing resin can be a single resin or a mixture of resins. The basic resin can be a homopolymer or a copolymer. The identity of the basic resin is not limited as long as the basic resin is capable of swelling and absorbing at least 10 times its weight in water, when in a charged form. The weak basic resin typically is present in its free base, or neutral, form, i.e., about 75% to about 100% of the basic moieties, e.g., amino groups, are present in a neutral, uncharged form. The strong basic resins typically are present in the hydroxide (OH) or bicarbonate ($HCO_3$) form.

The basic water-absorbing resin typically is a lightly crosslinked acrylic type resin, such as a poly(vinylamine) or a poly(dialkylaminoalkyl (meth)acrylamide). The basic resin also can be a polymer such as a lightly crosslinked polyethylenimine, a poly(allylamine), a poly(allylguanidine), a poly(dimethyldi-allylammonium hydroxide), a guanidine-modified polystyrene, such as

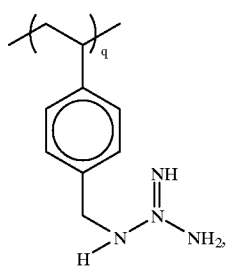

a poly(vinylguanidine), i.e., poly(VG), a strong basic water-absorbing resin having the following general structural formula

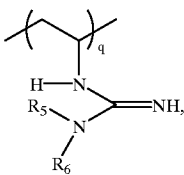

wherein q is a number from 10 to about 100,000, and $R_5$ and $R_6$, independently, are selected from the group consisting of hydrogen, $C_1$–$C_4$ alkyl, $C_3$–$C_6$ cycloalkyl, benzyl, phenyl, alkyl-substituted phenyl, naphthyl, and similar aliphatic and aromatic groups. The lightly crosslinked basic water-absorbing resin can contain other copolymerizable units and is crosslinked using a polyfunctional organic compound, as set forth above with respect to the acidic water-absorbing resin.

A basic water-absorbing resin used in the multicomponent SAP particles typically contains an amino or a guanidino group. Accordingly, a water-soluble basic resin also can be crosslinked in solution by suspending or dissolving an uncross-linked basic resin in an aqueous or alcoholic medium, then adding a di- or polyfunctional compound capable of crosslinking the basic resin by reaction with the amino groups of the basic resin. Such crosslinking agents include, for example, multifunctional aldehydes (e.g., glutaraldehyde), multifunctional acrylates (e.g., butanediol diacrylate, TMPTA), halohydrins (e.g., epichlorohydrin), di-halides (e.g., dibromopropane), disulfonate esters (e.g., $ZA(O_2)O$—$(CH_2)_n$—$OS(O)_2Z$, wherein n is 1 to 10, and Z is methyl or tosyl), multifunctional epoxies (e.g., ethylene glycol diglycidyl ether), multifunctional esters (e.g., dimethyl adipate), multifunctional acid halides (e.g., oxalyl chloride), multifunctional carboxylic acids (e.g., succinic acid), carboxylic acid anhydrides (e.g., succinic anhydride), organic titanates (e.g., TYZOR AA from DuPont), melamine resins (e.g., CYMEL 301, CYMEL 303, CYMEL 370, and CYMEL 373 from Cytec Industries, Wayne, N.J.), hydroxymethyl ureas (e.g., N,N'-dihydroxymethyl-4,5-dihydroxyethyleneurea), and multifunctional isocyanates (e.g., toluene diisocyanate or methylene diisocyanate). Crosslinking agents also are disclosed in Pinschmidt, Jr. et al. U.S. Pat. No. 5,085,787, incorporated herein by reference, and in EP 450 923.

Conventionally, the crosslinking agent is water- or alcohol-soluble, and possesses sufficient reactivity with the basic resin such that crosslinking occurs in a controlled fashion, preferably at a temperature of about 25° C. to about 150° C. Preferred crosslinking agents are ethylene glycol diglycidyl ether (EGDGE), a water-soluble diglycidyl ether, and a dibromoalkane, an alcohol-soluble compound.

The basic resin, either strongly or weakly basic, therefore, can be any resin that acts as an SAP in its charged form. The basic resin typically contains amino or guanidino moieties. Examples of basic resins include a poly(vinylamine), a polyethylenimine, a poly(vinylguanidine), a poly(allylamine), a poly(allylguanidine), or a poly(dialkylaminoalkyl (meth)acrylamide) prepared by polymerizing and lightly crosslinking a monomer having the structure

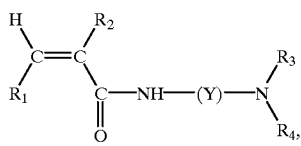

or its ester analog

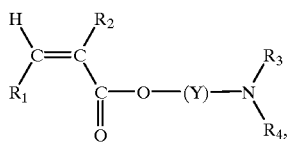

wherein $R_1$ and $R_2$, independently, are selected from the group consisting of hydrogen and methyl, Y is a divalent straight chain or branched organic radical having 1 to 8 carbon atoms, and $R_3$ and $R_4$, independently, are alkyl radicals having 1 to 4 carbon atoms. Preferred basic resins include a poly(vinylamine), polyethylenimine, poly(vinylguanadine), poly(dimethylaminoethyl acrylamide) (poly(DAEA)), and poly(dimethylaminopropyl methacrylamide) (poly(DMAPMA)). Analogous to microdomains of an acidic resin, the present multicomponent SAPs can contain microdomains of a single basic resin, microdomains containing a mixture of basic resins, or microdomains of different basic resins.

As indicated above, the above-described acidic and basic water-absorbing resins, when added separately in the formation of a sheet material (as opposed to being contained together in the same particle) provide essentially the same advantages described for the multicomponent SAP particles of initial water absorption rate, AUL, sheet material structural integrity, little to no loss of superabsorbent particles during manufacture and product handling, smooth feel, and up to 100% superabsorbent polymer.

The multicomponent SAPs can be prepared by various methods. It should be understood that the exact method of preparing a multicomponent SAP is not limited by the following embodiments. Any method that provides a particle having at least one microdomain of an acidic resin in contact with or in close proximity to at least one microdomain of a basic resin is suitable.

In one method, dry particles of a basic resin, optionally surface crosslinked and/or annealed, are admixed into a rubbery gel of an acidic resin. The resulting mixture is extruded, then dried, and optionally surface crosslinked and/or annealed, to provide multicomponent SAP particles having microdomains of a basic resin dispersed in a continuous phase of an acidic resin. Alternatively, particles of an acidic resin, optionally surface crosslinked and/or annealed, can be admixed into a rubbery gel of a basic resin, and the resulting mixture is extruded and dried, and optionally surface crosslinked and/or annealed, to provide multicomponent SAP particles having microdomains of an acidic resin dispersed in a continuous phase of a basic resin.

In another method, dry particles of an acidic resin can be admixed with dry particles of a basic resin, and the resulting mixture is formed into a hydrogel, then extruded, to form multicomponent SAP particles.

In yet another method, a rubbery gel of an acidic resin and a rubbery gel of a basic resin, each optionally surface crosslinked and/or annealed, are coextruded, and the coextruded product is dried, and optionally surface crosslinked and/or annealed, to form multicomponent SAP particles containing microdomains of the acidic resin and the basic resin dispersed throughout the particle.

The method of preparing the multicomponent SAP particles, therefore, is not limited, and does not require an extrusion step. Persons skilled in the art are aware of other methods of preparation wherein the multicomponent SAP contains at least one microdomain of an acidic resin and at least one microdomain of a basic resin in contact or in close proximity with each other. One example is agglomeration of fine particles of at least one acidic resin and at least one basic resin with each other, and optionally a matrix resin, to provide a multicomponent SAP particle containing microdomains of an acidic and/or basic resin. The multicomponent SAP particles can be ground to a desired particle size, or can be prepared by techniques that yield the desired particle size. Other nonlimiting methods of preparing an SAP particle of the present invention are set forth in the examples.

In embodiments wherein an acidic resin and a basic resin are present, as separate resins (bicomponent), as multicomponent resin particles, or as microdomains within a matrix of a matrix resin, particles of an acidic resin and a basic resin (as multicomponent particles or as separate acidic and basic resin particles) are admixed with a rubbery gel of a matrix resin, and the resulting mixture is extruded, then dried, to form SAP particles (separate acidic and basic resins or multicomponent acidic and basic resins) having the acidic resin and the basic resin (as one particle or two) dispersed in a continuous phase of a matrix resin. Alternatively, rubbery gels of an acidic resin, basic resin, and matrix resin can be coextruded to provide a multicomponent SAP containing microdomains of an acidic resin, a basic resin, and a matrix resin dispersed throughout the particle. In this embodiment, the acidic resin, basic resin, and resulting multicomponent SAP, each can be optionally surface crosslinked and/or annealed.

The matrix resin is any resin that allows fluid transport such that a liquid medium can contact the acidic and basic resin. The matrix resin typically is a hydrophilic resin capable of absorbing water. Nonlimiting examples of matrix resins include poly(vinyl alcohol), poly(N-vinylformamide), polyethylene oxide, poly(meth)acrylamide, poly(hydroxyethyl acrylate), hydroxyethylcellulose, methylcellulose, and mixtures thereof. The matrix resin also can be a conventional water-absorbing resin, for example, a polyacrylic acid neutralized greater than 25 mole %, and typically greater than 50 mole In preferred embodiments, the acidic resin, the basic resin, and/or the multicomponent SAP particles are surface treated and/or annealed. Surface treatment and/or annealing results in surface crosslinking of the particle. In especially preferred embodiments, the acidic and/or basic resins comprising the multicomponent SAP particles are surface treated and/or annealed, and the entire multicomponent SAP particle is surface treated and/or annealed. It has been found that surface treating and/or annealing of an acidic resin, a basic resin, and/or a multicomponent SAP particle of the present invention enhances the ability of the resin or multicomponent SAP particle to absorb and retain aqueous media under a load.

Surface crosslinking is achieved by contacting an acidic resin, a basic resin, and/or a multicomponent SAP particle with a solution of a surface crosslinking agent to wet predominantly only the outer surfaces of the resin or SAP particle. Surface crosslinking and drying of the resin or multicomponent SAP particle then is performed, preferably by heating at least the wetted surfaces of the resin or multicomponent SAP particles.

Typically, the acidic resin particles, the basic resin particles, and/or multicomponent SAP particles (multicomponent, acidic resin particles, and/or basic resin particles) are surface treated with a solution of a surface crosslinking agent. The solution contains about 0.01% to about 4%, by weight, surface crosslinking agent, and preferably about 0.4% to about 2%, by weight, surface crosslinking agent in a suitable solvent, for example, water or an alcohol. The solution can be applied as a fine spray onto the surface of freely tumbling resin particles or multicomponent SAP particles at a ratio of about 1:0.01 to about 1:0.5 parts by weight resin or SAP particles to solution of surface crosslinking agent. The surface crosslinker is present in an amount of 0% to about 5%, by weight of the resin or SAP particle, and preferably 0% to about 0.5% by weight. To achieve the full advantage of the present invention, the surface crosslinker is present in an amount of about 0.001% to about 0.1% by weight.

The crosslinking reaction and drying of the surface-treated resins or multicomponent SAP particles are achieved by heating the surface-treated polymer at a suitable temperature, e.g., about 25° C. to about 150° C., and preferably about 105° C. to about 120° C. However, any other method of reacting the crosslinking agent to achieve surface crosslinking of the resin or multicomponent SAP particles, and any other method of drying the resin or multicomponent SAP particles, such as microwave energy, or the such as, can be used.

With respect to the basic resin or particles thereof, or multicomponent SAP particles having a basic resin present on the exterior surface of the particles, suitable surface crosslinking agents include di- or polyfunctional molecules capable of reacting with amino groups and crosslinking a basic resin. Preferably, the surface crosslinking agent is alcohol or water soluble and possesses sufficient reactivity with a basic resin such that crosslinking occurs in a controlled fashion at a temperature of about 25° C. to about 150° C.

Nonlimiting examples of suitable surface crosslinking agents for basic resins include:

(a) dihalides and disulfonate esters, for example, compounds of the formula

wherein p is a number from 2 to 12, and Y, independently, is halo (preferably bromo), tosylate, mesylate, or other alkyl or aryl sulfonate esters;

(b) multifunctional aziridines;

(c) multifunctional aldehydes, for example, glutaraldehyde, trioxane, paraformaldehyde, terephthaldehyde, malonaldehyde, and glyoxal, and acetals and bisulfites thereof;

(d) halohydrins, such as epichlorohydrin;

(e) multifunctional epoxy compounds, for example, ethylene glycol diglycidyl ether, bisphenol A diglycidyl ether, and bisphenol F diglycidyl ether, (f) multifunctional carboxylic acids and esters, acid chlorides, and anhydrides derived therefrom, for example, di- and polycarboxylic acids containing 2 to 12 carbon atoms, and the methyl and ethyl esters, acid chlorides, and anhydrides derived therefrom, such as oxalic acid, adipic acid, succinic acid, dodecanoic acid, malonic acid, and glutaric acid, and esters, anhydrides, and acid chlorides derived therefrom;

(g) organic titanates, such as TYZOR AA, available from E.I. DuPont de Nemours, Wilmington, Del.;

(h) melamine resins, such as the CYMEL resins available from Cytec Industries, Wayne, N.J.;

(i) hydroxymethyl ureas, such as N,N'-dihydroxymethyl-4,5-dihydroxyethylene urea;

(j) multifunctional isocyanates, such as toluene diisocyanate, isophorone diisocyanate, methylene diisocyanate, xylene diisocyanate, and hexamethylene diisocyanate; and (k) other crosslinking agents for basic water-absorbing resins known to persons skilled in the art.

A preferred surface crosslinking agent is a dihaloalkane, ethylene glycol diglycidyl ether (EGDGE), or a mixture thereof, which crosslink a basic resin at a temperature of about 25° C. to about 150° C. Especially preferred surface crosslinking agents are dibromoalkanes containing 3 to 10 carbon atoms and EGDGE.

With respect to the acidic water-absorbing resins or particles thereof, or multicomponent SAP particles having an acidic resin on the exterior surface of the particles, suitable surface crosslinking agents are capable of reacting with acid moieties and crosslinking the acidic resin. Preferably, the surface crosslinking agent is alcohol soluble or water soluble, and possesses sufficient reactivity with an acidic resin such that crosslinking occurs in a controlled fashion, preferably at a temperature of about 25° C. to about 150° C.

Nonlimiting examples of suitable surface crosslinking agents for acidic resins include:

(a) polyhydroxy compounds, such as glycols and glycerol;

(b) metal salts;

(c) quaternary ammonium compounds;

(d) a multifunctional epoxy compound;

(e) an alkylene carbonate, such as ethylene carbonate or propylene carbonate;

(f) a polyaziridine, such as 2,2-bishydroxymethyl butanol tris[3-(1-aziridine propionate]);

(g) a haloepoxy, such as epichlorhydrin;

(h) a polyamine, such as ethylenediamine;

(i) a polyisocyanate, such as 2,4-toluene diisocyanate; and (j) other crosslinking agents for acidic water-absorbing resins known to persons skilled in the art.

Figure 6:
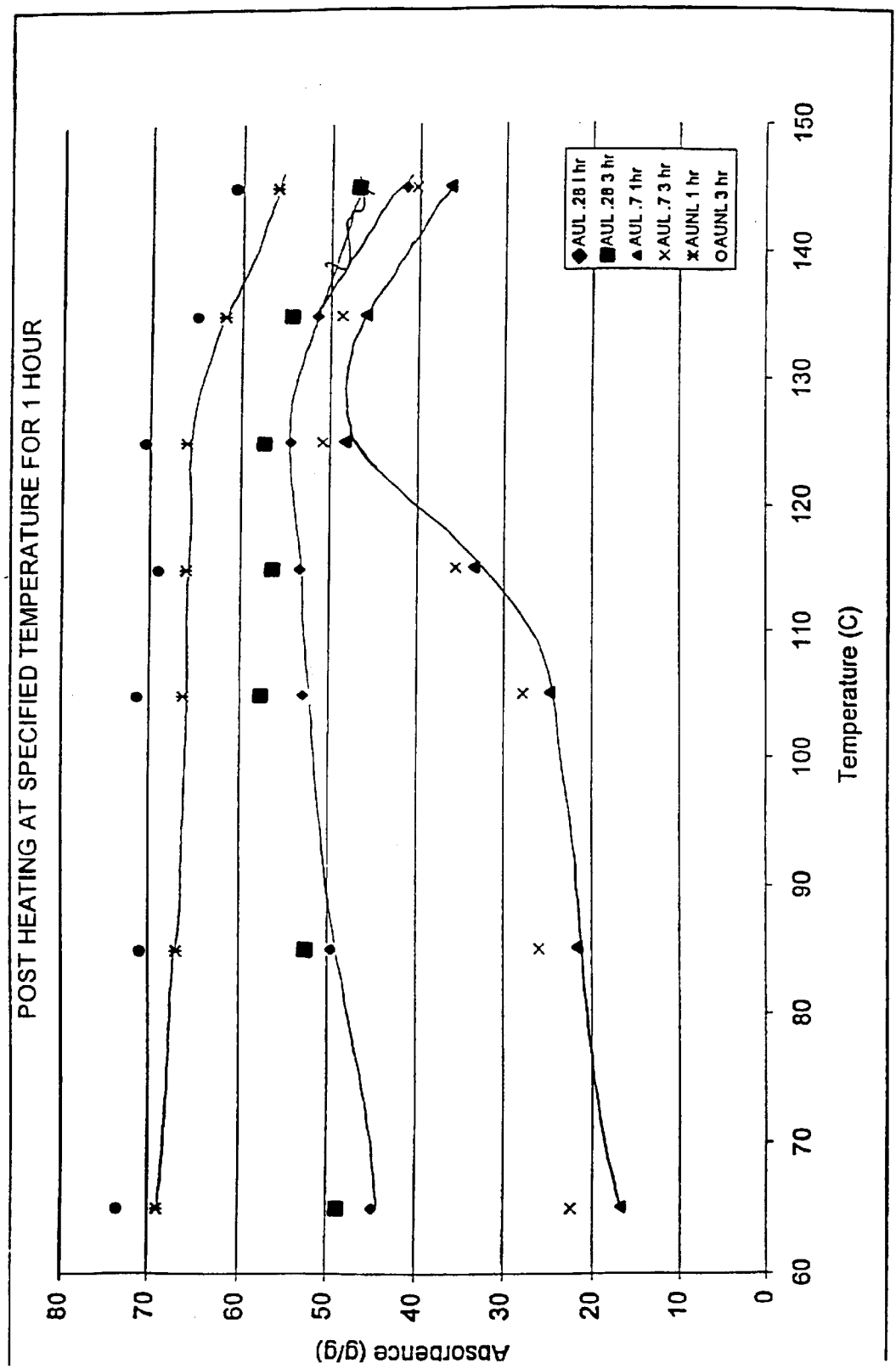
FIG. 6 contains plots of absorbance (in grams of synthetic urine per gram of multicomponent SAP particles) vs. annealing temperature for a one-hour annealing step.
Figure 7:
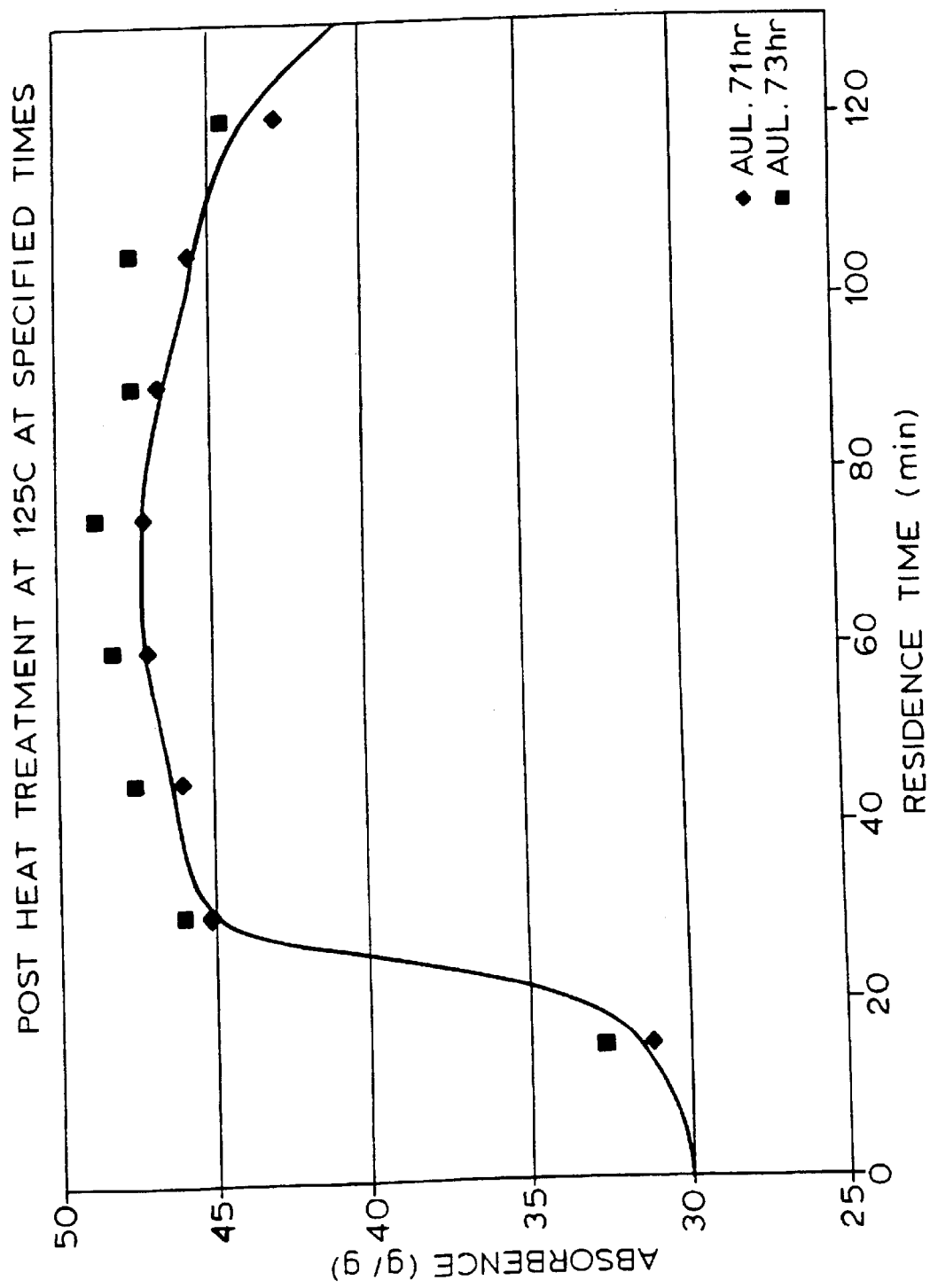
FIG. 7 contains a plot of absorbance (in grams of synthetic urine per gram of multicomponent SAP particles) vs. time for an annealing step performed at 125° C.

In addition to, or in lieu of, surface treating, the acidic resin or its particles, the basic resin or its particles, the matrix resin, or the multicomponent SAP particles, or any combination thereof, can be annealed to improve water absorption and retention properties under a load. It has been found that heating a resin for a sufficient time at a sufficient temperature above the Tg (glass transition temperature) of the resin or microdomains improves the absorption properties of the resin. FIGS. 6 and 7 contain graphs showing the effect of annealing time and temperature on the absorption properties of a multicomponent SAP particle of the present invention comprising 55% by weight poly(vinylamine) and 45% by weight poly(acrylic acid), made by the method set forth hereafter in Example 12.

In accordance with one important embodiment of the present invention, it has been found that when a layer of the acidic resin and basic resin particles, or a layer of the multicomponent SAP particles, is heated to at least about 50° C. during sheet material manufacture (e.g., by a heated pressure roll or oven), not only are the absorption properties improved, but the particles are strongly adhered to themselves and to any fiber or filler (e.g., clay) contained in the sheet material so that there is little to no loss of superabsorbent particles during manufacture and handling. Thus, a sheet material having 0%–60% by weight non-SAP fiber, and without added adhesive, has new and unexpected structural integrity, for the above-described uses, particularly diaper cores.

The graphs in FIGS. 6 and 7 show that heating multicomponent SAP particles for about 20 to about 120 minutes at a temperature of about 60° C. to about 150° C. improves absorption properties. The absorption properties, i.e., AUL and AUNL, graphed in FIGS. 6 and 7 are discussed in detail hereafter. Preferably, annealing is performed for about 30 to about 100 minutes at about 80° C. to about 140° C. during or after sheet material manufacture. To achieve the full advantage of annealing, the SAP particles are annealed for about 40 to about 90 minutes at about 100° C. to about 140° C. Similar results are achieved using a combination of the single component acidic and basic resins in the sheet materials.

In accordance with another important embodiment of the present invention, equivalent structural integrity can be achieved by adding water or other chemical expedient in an amount of at least about 2% by weight, preferably about 5% to about 30% deionized water, based on the total weight of acidic and basic resins, and compressing the resins together, while wet, at a pressure of at least 100 psig, preferably about 5,000 psig to about 10,000 psig. Other chemical expedients include, but are not limited to, alcohols (e.g., $C_{1-3}$alcohols), diols (e.g., propylene glycol), glycerin, aprotic amides (e.g., DMF and NMP), and DMSO.

A strong acidic resin can be used with either a strong basic resin or a weak basic resin, or a mixture thereof. A weak acidic resin can be used with a strong basic resin or a weak basic resin, or a mixture thereof. Preferably, the acidic resin is a weak acidic resin and the basic resin is a weak basic resin. This result is unexpected in view of the ion exchange art wherein a combination of a weak acidic resin and a weak basic resin does not perform as well as other combinations, e.g., a strong acidic resin and a strong basic resin. In more preferred embodiments, the weak acidic resin, the weak basic resin, and/or the multicomponent SAP particles are surface crosslinked and/or annealed.

As previously discussed, sodium poly(acrylate) conventionally is considered the best SAP, and, therefore, is the most widely used SAP in commercial applications. Sodium poly(acrylate) has polyelectrolytic properties that are responsible for its superior performance in absorbent applications. These properties include a high charge density, and charge relatively close to the polymer backbone.

However, an acidic resin in the free acid form, or a basic resin in the free base form, typically do not function as a commercially useful SAP because there is no ionic charge on either type of polymer. A poly(acrylic acid) resin, or a poly(vinylamine) resin, are neutral polymers, and, accordingly, do not possess the polyelectrolytic properties necessary to provide SAPs useful commercially in diapers, catamenial devices, and similar absorbent articles. The driving force for water absorption and retention, therefore, is lacking. This is illustrated in Tables 1 and 2 showing the relatively poor absorption and retention properties for a neutral poly(DAEA) in absorbing synthetic urine. However, when converted to a salt, an acidic resin, such as a polyacrylic acid, or a basic resin, such as a poly(dialkylaminoalkyl (meth)acrylamide), then behave such as a commercially useful SAP.

It has been found that basic resins, in their free base form, are useful components in superabsorbent materials further containing an acidic water-absorbing resin. For example, a superabsorbent material comprising an admixture of a poly(dialkylaminoalkyl (meth)acrylamide) and an acidic water-absorbing resin, such as polyacrylic acid, demonstrates good water absorption and retention properties. Such an SAP material comprises two uncharged, slightly crosslinked polymers, each of which is capable of swelling and absorbing aqueous media. When contacted with water or an aqueous electrolyte-containing medium, the two uncharged polymers neutralize each other to form a superabsorbent material. This also reduces the electrolyte content of the medium absorbed by polymer, further enhancing the polyelectrolyte effect. Neither polymer in its uncharged form behaves as an SAP by itself when contacted with water. However, superabsorbent materials, which contain a simple mixture of two resins, one acidic and one basic, are capable of acting as an absorbent material because the two resins are converted to their polyelectrolyte form. These superabsorbent materials have demonstrated good water absorption and retention properties. The multicomponent SAP particles, containing at least one microdomain of an acidic resin and at least one microdomain of a basic resin are preferred, however, since they exhibit improved water absorption and retention, and improved permeability, over simple mixtures of acidic resin particles and basic resin particles.

In the single component mixture of acidic and basic resin particles as well as in the multicomponent SAP particles, the weak basic resin is present in its free base, e.g., amine form, and the acidic resin is present in its free acid form. It is envisioned that a low percentage, i.e., about 25% or less, of the amine and/or acid functionalities can be in their charged form. The low percentage of charged functionalities does not adversely affect performance of the SAP particles, and can assist in the initial absorption of a liquid.

Both the mixture of single component acidic and basic resins and the multicomponent SAP particles contained separately or in admixture in the sheet materials of the present invention are useful particularly in planar articles designed to absorb large amounts of liquids, especially electrolyte-containing liquids, such as in diapers and catamenial devices.

The following nonlimiting examples illustrate the preparation of the multicomponent SAP particle embodiment for manufacturing the sheet materials of the present invention, and it should be understood that for each example, the sheet materials of the present invention can be manufactured to include the separate acidic and basic resin components of the multicomponent particles of the examples.

EXAMPLE 1

Preparation of Poly(Acrylic Acid) 0% Neutralized (Poly(AA) DN=0)

A monomer mixture containing acrylic acid (270 grams), deionized water (810 grams), methylene-bisacrylamide (0.4 grams), sodium persulfate (0.547 grams), and 2-hydroxy-2-methyl-1-phenyl-propan-1-one (0.157 grams) was prepared, then sparged with nitrogen for 15 minutes. The monomer mixture was placed into a shallow glass dish, then the monomer mixture was polymerized under 15 mW/cm$^2$ of UV light for 25 minutes. The resulting poly(AA) was a rubbery gel.

The rubbery poly(AA) gel was cut into small pieces, then extruded through a KitchenAid Model K5SS mixer with meat grinder attachment. The extruded gel was dried in a forced-air oven at 120° C., and finally ground and sized through sieves to obtain the desired particle size.

This procedure provided a lightly crosslinked polyacrylic acid hydrogel with a degree of neutralization of zero (DN=0).

EXAMPLE 2

Preparation of Poly(dimethylaminoethylacrylamide) (Poly(DAEA))

A monomer mixture containing 125 grams N-(2-dimethylaminoethyl) acrylamide (DAEA), 300 grams deionized water, 0.6 gram methylenebisacrylamide, and 0.11 grams V-50 initiator (i.e., 2,2'-azobis(2-amidinopropane) hydrochloride initiator available from Wako Pure Chemical Industries, Inc., Osaka, Japan) was sparged with argon for 15 minutes. Then the resulting reaction mixture was placed in a shallow dish and polymerized under 15 mW/cm$^2$ of UV light for 25 minutes. The polymerization was exothermic, eventually reaching about 100° C. The resulting lightly crosslinked poly(DAEA) was a rubbery gel. The rubbery poly(DAEA) gel was crumbled by hand, then dried at 60° C. for 16 hours, and finally ground and sized through sieves to obtain the desired particle size.

EXAMPLE 3

Preparation of Poly (dimethylaminopropylmethacrylamide) (Poly (DMAPMA))

A monomer mixture containing DMAPMA monomer (100 grams), deionized water (150 grams), methylenebisacrylamide (0.76 grams) and V-50 initiator (0.72 grams) was placed in a glass beaker. The monomer mixture was purged with argon for 25 minutes, covered, and then placed in an oven at about 60° C. for about 60 hours. The resulting lightly crosslinked poly(DMAPMA) was a rubbery gel. The rubbery poly(DMAPMA) gel was crumbled by hand, dried at 60° C. for 16 hours, and then ground and sized through sieves to obtain the desired particle size.

EXAMPLE 4

Preparation of a Poly(N-vinylformamide) and a Poly(vinylamine)

A monomer mixture containing N-vinylformamide (250 grams), deionized water (250 grams), methylenebisacrylamide (1.09 grams), and V-50 initiator (0.42 grams) was placed in a shallow dish, then polymerized under an ultraviolet lamp as set forth in Example 1 until the mixture polymerized into a rubbery gel. The lightly crosslinked poly(N-vinylformamide) then was hydrolyzed with a sodium hydroxide solution to yield a lightly crosslinked poly(vinylamine).

EXAMPLE 5

Preparation of a Strong Acidic Water-Absorbing Resin

A monomer mixture containing acrylic acid (51 grams), 2-acrylamido-2-methyl-1-propanesulfonic acid (AMPS, 25.8 grams), deionized water (230 grams), methylenebisacrylamide (0.088 grams), sodium persulfate (0.12 grams), and 2-hydroxy-2-methyl-1-phenyl-propan-1-one (0.034 grams) was prepared, then placed in shallow dish and polymerized under an ultraviolet lamp as set forth in Example 1 until the monomer mixture polymerizes into rubbery gel.

The gel was cut into small pieces then extruded through a KitchenAid Model K5SS mixer with a meat grinder attachment. The extruded gel then was dried in a forced-air oven at 120° C., ground, and sized through sieves to obtain the desired particle size.

This resulting lightly crosslinked acidic resin contained 15 mole percent strong acid functionality (—SO$_3$H) and 85 mole percent weak acid functionality (—CO$_2$H).

EXAMPLE 6

Preparation of a Crosslinked Poly(vinyl Alcohol-co-vinylamine) Resin

Poly(vinyl alcohol-co-vinylamine) (50 grams, 6 mol % vinylamine), available from Air Products Inc., Allentown, Pa., was dissolved in 450 grams of deionized water in a glass jar to form a viscous solution. Ethylene glycol diglycidyl ether (0.2 grams) was added to the viscous solution, with stirring. The jar then was covered and placed in a 60° C. oven for 16 hours to yield a rubbery gel of a lightly crosslinked poly(vinyl alcohol-co-vinylamine).

EXAMPLE 7

Preparation of a Crosslinked Poly(vinylamine) Resin

To 2 liters of a 3% by weight aqueous poly(vinylamine) solution was added 0.18 g of ethyleneglycol diglycidyl ether (EGDGE). The resulting mixture was stirred to dissolve the EGDGE, then the mixture was heated to about 60° C. and held for one hour to gel. The gel was heated to about 80° C. and held until about 90% of the water was removed. The resulting get then was extruded and dried to a constant weight at 80° C. The dried, lightly crosslinked poly (vinylamine) then was cryogenically milled to form a granular material.

EXAMPLE 8

Preparation of a Poly(DAEA)/Poly(AA) Multicomponent SAP (Poly(AA) Continuous Phase)

The undried, rubbery poly(AA) hydrogel prepared in Example 1 (133 grams) was cut into pieces and extruded through a KitchenAid Model K5SS mixer with meat grinder attachment. The gel then was mixed with 50 grams of the dry poly(DAEA) particles (<106 microns in size) prepared in Example 2. The resulting mixture was extruded three times using the KitchenAid mixer, then dried in a 60° C. forced-air oven for 16 hours and finally ground and sized through sieves to obtain the desired particle size. The process yielded 83 grams of multicomponent SAP particles comprising poly(DAEA) microdomains dispersed in a continuous poly (AA) phase, and having a weight ratio of poly(DAEA) to poly(AA) of about 60/40.

EXAMPLE 9

Surface Treatment of the Poly(DAEA)/Poly(AA) Multicomponent SAP of Example 8

A surface-treating solution was prepared by admixing 0.15 grams EGDGE, 7.88 grams propylene glycol, and 1.97 grams deionized water until homogeneous. Ten grams of the poly(DAEA)/poly(AA) multicomponent SAP of Example 8 were placed in a beaker fitted with a vertical shaft stirrer. The dry multicomponent SAP was stirred at a sufficient speed to fluidize the SAP in the beaker, then 0.4 grams of the surface-treating solution was added to the fluidized SAP dropwise via syringe. Then, stirring was stopped, and the beaker was placed in a 125° C. forced-air oven for one hour to yield a poly(DAEA)/poly(AA) multicomponent SAP surface treated with 600 ppm of EGDGE.

EXAMPLE 10

Preparation of a Poly(AA)/Poly(DMAPMA) Multicomponent SAP (Poly(DMAPMA) Continuous Phase)

The poly(DMAPMA) hydrogel prepared in Example 3 (70 grams) was cut into pieces and extruded through a KitchenAid Model K5SS mixer with meat grinder attachment. The gel then was mixed with 32 grams of dry poly(AA) particles (<106 microns in size) prepared in Example 1. The resulting mixture then was extruded three times using the KitchenAid mixer, followed by drying in a 60° C. forced-air oven at 60° C. for 16 hours, and finally grinding and sizing through sieves to obtain the desired particle size. The process yielded 60 grams of multicomponent SAP particles comprising poly(AA) microdomains dispersed in a continuous poly(DMAPMA) phase, and having a poly(AA) to poly(DMAPMA) weight ratio of about 50/50.

EXAMPLE 11

Surface Treatment of the Poly(AA)/Poly (DMAPMA) Multicomponent SAP of Example 10

A surface-treating solution was prepared by admixing 0.375 grams 1,8-dibromooctane and 9.625 grams isopropanol until homogeneous. Ten grams of the poly(AA)/poly(DMAPMA) multicomponent SAP of Example 10 were placed in a beaker fitted with a vertical shaft stirrer. The dry multicomponent SAP was stirred at a sufficient speed to fluidize the SAP in the beaker, then 0.4 grams of the surface-treating solution was added to the fluidized SAP dropwise via syringe. Next, stirring was stopped, and the beaker was placed in a 105° C. forced-air oven for one hour to yield a poly(AA)/poly(DMAPMA) multicomponent SAP surface treated with 1,500 ppm of 1,8-dibromooctane.

EXAMPLE 12

Poly(DAEA)/Poly(AA) Multicomponent SAP Prepared by Gel Coextrusion

Thirty grams of the poly(DAEA) of Example 2 were extruded through a KitchenAid Model K5SS mixer with meat grinder attachment. Twenty-four grams of the poly(AA) hydrogel of Example 1 also were extruded through a KitchenAid Model K5SS mixer with meat grinder attachment. The two extrudates then were combined via hand mixing, followed by extruding the resulting mixture two times using the meat grinder. The extruded product then was dried for 16 hours at 60° C., milled and sized to 180–710 microns, and finally surface treated with 200 ppm EGDGE (as described in Example 9). The procedure yields multicomponent SAP containing microdomains of poly(DAEA) and poly(AA), and having poly(DAEA)/poly(AA) weight ratio of about 60/40.

EXAMPLE 13

Preparation of Poly(vinylguanadine) (Poly(VG))

To 500 ml of an aqueous solution of poly(vinylamine) (1.98% solids, 93% hydrolyzed) was added 38.5 ml of 6M hydrochloric acid and 9.65 g of cyanamide ($H_2NCN$). The resulting solution was heated under reflux for 8 hours. The solution next was diluted to a volume of 3L (liters) with a 5% sodium hydroxide solution, then ultrafiltered ($M_w$ cut off of 100,000) with 15 of a 5% sodium hydroxide solution, followed by 15L of deionized water. The resulting product was concentrated to a 2.6% solids solution, having a pH 11.54. A poly(vinylamine) solution has a pH 10.0. The 2.6% solids solution gave a negative silver nitrate test, and a gravimetric analysis of the polymer, after the addition of HCl, gave the following composition: vinylguanidine 90%, vinylformamide 7%, and vinylamine 3%. Infrared analysis shows a strong absorption at $1651\ cm^{-1}$, which is not present in poly(vinylamine), and corresponds to a C=N stretch.

EXAMPLE 14

Preparation of a Crosslinked Poly(VG) Resin

The 2.6% solids solution of Example 13 was further concentrated to 12.5% solids by distillation. To this 12.5% solids solution was added 1 mole % EGDGE, and the resulting solution then was heated in a 60° C. oven for 5 hours to form a gel of lightly crosslinked poly(vinylguanidine).

EXAMPLE 15

Preparation of a Coextruded Poly(VG)/Poly(AA) Multicomponent SAP

The crosslinked poly(VG) hydrogel of Example 14 was coextruded with 1 mole equivalent of the poly(AA) of Example 1 by the method set forth in Example 12. A portion of the coextruded poly(VG)/poly(AA) multicomponent SAP then was surface crosslinked with 200 ppm EGDGE, by the method set forth in Example 9.

EXAMPLE 16

PEI/Poly(AA) Coextruded Multicomponent SAP Prepared by Gel Coextrusion

Aqueous solutions containing 10% and 20% by weight polyethyl-enimine (PEI, $M_w$ of 60,000, available commercially as EPOMIN P-1000, Aceto Corp., Lake Success, N.Y.) were crosslinked with 1.0 and 1.5 mole % EGDGE by the method set forth in Example 6, i.e., heating for 16 hours at 60° C., to provide rubbery gels. The rubbery PEI gels (37.4 wt. %) were coextruded with the poly(AA) gel of Example 1 (62.6 wt. %) in accordance with the method set forth in Example 12, and the resulting coextruded multicomponent SAPs were dried in an oven at 60° C. The dried multicomponent SAPs were cryogenically milled, and then sized.

In the test results set forth below, the multicomponent SAP particles of the present invention were tested for absorption under no load (AUNL) and absorption under load at 0.28 psi and 0.7 psi (AUL (0.28 psi) and AUL (0.7 psi)). Absorption under load (AUL) is a measure of the ability of an SAP to absorb fluid under an applied pressure. The AUL was determined by the following method, as disclosed in U.S. Pat. No. 5,149,335, incorporated herein by reference.

An SAP (0.160 g+/−0.001 g) is carefully scattered onto a 140-micron, water-permeable mesh attached to the base of a hollow Plexiglas cylinder with an internal diameter of 25 mm. The sample is covered with a 100 g cover plate and the cylinder assembly weighed. This gives an applied pressure of 20 $g/cm^2$ (0.28 psi). Alternatively, the sample can be covered with a 250 g cover plate to give an applied pressure of 51 $g/cm^2$ (0.7 psi). The screened base of the cylinder is placed in a 100 mm petri dish containing 25 milliliters of a test solution (usually 0.9% saline), and the polymer is allowed to absorb for 1 hour (or 3 hours). By reweighing the cylinder assembly, the AUL (at a given pressure) is calculated by dividing the weight of liquid absorbed by the dry weight of polymer before liquid contact.

The following tables contain absorption and retention data for the multicomponent SAP particles of the present invention, for individual polymers present in the multicomponent SAP particles, and for simple admixtures of the dry resins present in the multicomponent SAP particles. The data shows a significant improvement in water absorption and retention for the present multicomponent SAP particles containing microdomains of an acidic and/or basic resin polymers within each particle compared to the individual resins and a simple admixture of the individual resins. The data in Tables 1–6 shows the improved ability of multicomponent SAP particles of the present invention to absorb and retain an aqueous 0.9% saline solution.

TABLE 1

| SAP | AUL (0.28 psi, 1 hr.) | AUL (0.7 psi, 1 hr.) | AUNL (1 hr.) | AUL (0.28 psi, 3 hr.) | AUL (0.7 psi, 3 hr.) | AUNL (3 hr.) |
|---|---|---|---|---|---|---|
| Poly (DAEA) alone[1] | 9.6 | 8.1 | 23.9 | 13.5 | 9.3 | 24.2 |
| Polyacrylic Acid alone[2] | 11.9 | 10.8 | 14.3 | 12.0 | 10.8 | 14.3 |
| SAP-1[3] | 11.0 | 10.9 | 45.2 | 14.8 | 14.4 | 48.0 |
| SAP-2[4] | 12.5 | 9.6 | 26.7 | 18.9 | 13.1 | 30.1 |
| SAP-3[5] | 12.4 | 11.3 | 37.3 | 16.5 | 14.7 | 42.3 |
| SAP-4[6] | 20.1 | 17.2 | 28.6 | 24.7 | 20.7 | 34.1 |
| SAP-5[7] | 25.3 | 18.2 | 35.3 | 28.1 | 23 | 38.7 |
| Multicomponent SAP-1[8] | | | | | | |
| 0[9] | 23.7 | 16.3 | 41.6 | 26.9 | 20 | 41.7 |
| 200 | 26.7 | 24.7 | 41.2 | 27.1 | 25.1 | 39.9 |
| 400 | 27.3 | 24.1 | 43.4 | 27.5 | 24.5 | 44.0 |
| 600 | 29.2 | 23.8 | 41.8 | 29.5 | 24.0 | 41.2 |
| 800 | 26.6 | 24.1 | 40.9 | 26.7 | 24.2 | 41.7 |
| 1,000 | 27.5 | 24.3 | 39.9 | 27.8 | 24.2 | 40.7 |
| Multicomponent SAP-2[10] | | | | | | |
| 0[9] | 26.3 | 15.4 | 40 | 26.9 | 17.3 | 39.4 |
| 400 | 26.5 | 20.5 | 39.3 | 27 | 22.4 | 40.3 |
| 600 | 27 | 18.3 | 40.1 | 27.1 | 20.7 | 40.6 |

[1] particle size - 180–710 μm;
[2] 0% neutralization, particle size - 180–710 μm, surface crosslinked - 600 ppm EGDGE;
[3] mixture of 60% poly (DAEA), particle sizes less than 180 nm, and 40% polyacrylic acid - 0% neutralized;
[4] mixture of 60% poly (DAEA), particle sizes less than 180 nm, and 40% polyacrylic acid - 0% neutralized, crosslinked with 600 ppm EGDGE;
[5] mixture of 60% poly (DAEA), particle size - 180–710 μm, and 40% polyacrylic acid - 0% neutralized;
[6] mixture of 60% poly (DAEA), particle size - 180–710 μm, and 40% polyacrylic acid - 0% neutralized, crosslinked with 600 ppm EGDGE;
[7] mixture of 60% poly (DAEA), particle sizes less than 180 μm, and 40% polyacrylic acid - 20% neutralized, particle size 180–710 μm;
[8] multicomponent SAP containing microdomains of poly (DAEA) (<180 μm) as dispersed phase in poly (AA) (DN = 0) continuous phase, poly (DAEA)/poly (AA) weight ratio - 60/40;
[9] ppm surface crosslinking with EGDGE; and
[10] multicomponent SAP containing microdomains of poly (DAEA) (<180 μm) as dispersed phase in poly (AA) (DN = 20) continuous phase, poly (DAEA)/poly (AA) weight ratio - 60/40.

TABLE 2

| SAP | AUL (0.28 psi, 1 hr.) | AUL (0.7 psi, 1 hr.) | AUNL (1 hr.) | AUL (0.28 psi, 3 hr.) | AUL (0.7 psi, 3 hr.) | AUNL (3 hr.) |
|---|---|---|---|---|---|---|
| Poly (DMAPMA)[11] | 10.2 | 8.6 | 18 | 11.4 | 10 | 18.3 |
| Poly (DMAPMA)[12] | 9.3 | 5.2 | 17.4 | 11 | 6.9 | 17.8 |
| Polyacrylic acid[13] | 11.9 | 10.8 | 14.3 | 12.0 | 10.8 | 14.3 |
| SAP-6[14] | 14.5 | 10.9 | 18.8 | 17.2 | 14.3 | 20.9 |
| SAP-7[15] | 14 | 12 | 38.7 | 17.9 | 15.7 | 43.6 |
| SAP-8[16] | 12.5 | 10.4 | 24.8 | 14.5 | 12.4 | 24.8 |
| Multicomponent SAP-3[17] | | | | | | |
| 0[9] | 28.8 | 15 | 41.6 | 31 | 17.5 | 41.5 |
| 100 | 27.4 | 24.2 | 38.8 | 27.1 | 23.6 | 38.8 |
| 200 | 27.3 | 24.2 | 39.8 | 25.8 | 23 | 39 |
| 400 | 26 | 23 | 37 | 25.2 | 22.5 | 36.4 |
| 600 | 25.1 | 22.3 | 37.1 | 24.7 | 21.3 | 36.1 |

TABLE 2-continued

| SAP | AUL (0.28 psi, 1 hr.) | AUL (0.7 psi, 1 hr.) | AUNL (1 hr.) | AUL (0.28 psi, 3 hr.) | AUL (0.7 psi, 3 hr.) | AUNL (3 hr.) |
|---|---|---|---|---|---|---|
| Multicomponent SAP-4[18] | | | | | | |
| 0[9] | 31.9 | 11.6 | 44.2 | 31.8 | 15.7 | 44.9 |
| 200 | 27.6 | 24.3 | 37.8 | 27.5 | 23.4 | 38.1 |
| 400 | 27.5 | 23.7 | 37.4 | 27.2 | 23.1 | 38.8 |
| Multicomponent SAP-5[19] | | | | | | |
| 0[20] | 23.6 | 12.9 | 37.9 | 25 | 14.4 | 38.5 |
| 1500 | 24.7 | 16.9 | 36.4 | 25.5 | 18.3 | 37.5 |

[11] Poly (DMAPMA), particle size less than 106 μm;
[12] Poly (DMAPMA), particle size 106–180 μm;
[13] Polyacrylic acid, particle size 180–710 μm - 0% neutralized, surface crosslinked with 600 ppm EGDGE;
[14] mixture of 60% Poly (DMAPMA), particle size 106–180 μm, and 40% polyacrylic acid - 0% neutralized;
[15] mixture of 60% Poly (DMAPMA), particle size <106 μm, and 40% polyacrylic acid - 0% neutralized;
[16] mixture of 50% Poly (DMAPMA), and 50% polyacrylic acid - 0% neutralized;
[17] multicomponent SAP containing microdomains of poly (DMAPMA) (<106 μm) as dispersed phase in poly (AA) (DN = 0) continuous phase, poly (DMAPMA)/poly (AA) weight ratio 60/40;
[18] multicomponent SAP containing microdomains of poly (DMAPMA) (106–180 μm) as dispersed phase in poly (AA) (DN = 0) continuous phase, poly (DMAPMA)/poly (AA) weight ratio 60/40;
[19] multicomponent SAP containing microdomains of poly (AA) (DN = 0%) (<106 μm) as dispersed phase in poly (DMAPMA) continuous phase, poly (AA)/poly (DMAPMA) weight ratio 50/50; and
[20] ppm surface crosslinking with dibromooctane.

TABLE 3

| SAP | AUL (0.28 psi, 1 hr.) | AUL (0.7 psi, 1 hr.) | AUNL (1 hr.) | AUL (0.28 psi, 3 hr.) | AUL (0.7 psi, 3 hr.) | AUNL (3 hr.) |
|---|---|---|---|---|---|---|
| Poly (vinylamine) alone | 14.2 | 14.4 | 21.4 | 15 | 14.3 | 23.4 |
| SAP-9[21] | 21.2 | 18.6 | 28.3 | 23.8 | 20.5 | 36.3 |
| Multicomponent SAP-6[22] | | | | | | |
| 0[9] | 14.9 | 12.8 | 53.8 | 16.9 | 15.6 | 55.4 |
| 100 | 37.5 | 30.1 | 45.5 | 37.5 | 30.1 | 45.5 |
| 200 | 36.2 | 30.4 | 48.5 | 35.9 | 30.2 | 47.4 |
| 400 | 34.6 | 30.6 | 44.9 | 34.6 | 30.6 | 46.2 |

[21] mixture of 37% poly(vinylamine) and 63% poly (AA); and
[22] multicomponent SAP containing microdomains of poly (vinylamine) (<180 μm) as dispersed phase in poly (AA) (DN = 0) continuous phase, poly (vinylamine)/poly (AA) weight ratio - 37/63.

TABLE 4

Coextruded Multicomponent SAP of Example 12
(60/40 weight ratio poly (DAEA)/poly (AA))

| Surface Treatment | AUL (0.28 psi, 1 hr.) | AUL (0.7 psi, 1 hr.) | AUNL (1 hr.) | AUL (0.28 psi, 3 hr.) | AUL (0.7 psi, 3 hr.) | AUNL (3 hr.) |
|---|---|---|---|---|---|---|
| 0 | 30.5 | 13.3 | 41.1 | 30.6 | 16.3 | 40.2 |
| 200 ppm EGDGE | 31 | 27.7 | 40.2 | 30.8 | 27.3 | 39.9 |

TABLE 5

| SAP | AUL (0.28 psi, 1 hr.) | AUL (0.7 psi, 1 hr.) | AUNL (1 hr.) | AUL (0.28 psi, 3 hr.) | AUL (0.7 psi, 3 hr.) | AUNL (3 hr.) |
|---|---|---|---|---|---|---|
| Poly (vinylguanidine) hydrochloride alone | 21 | 16.1 | 31.2 | 22.4 | 18.0 | 32.7 |
| Multicomponent SAP-7[23] | | | | | | |
| 0[9] | 18.8 | 12.7 | 40.6 | 21.2 | 15.3 | 46.8 |
| 200 | 22 | 19.2 | 33.5 | 23.5 | 20.3 | 37.4 |

[23]multicomponent SAP containing microdomains of poly (VG) and poly (AA), with a poly (VG)/poly (AA) weight ratio - 50/50.

TABLE 6

Coextruded Multicomponent SAP of Example 16
(37.4/62.6 weight ratio PEI/poly(AA))

| PEI Gel (% Solids) | Cross-linker Level[24] | AUL (0.28 psi, 1 hr.) | AUL (0.7 psi, 1 hr.) | AUNL (1 hr.) | AUL (0.28 psi, 3 hr.) | AUL (0.7 psi, 3 hr.) | AUNL (3 hr.) |
|---|---|---|---|---|---|---|---|
| 20 | 1.0 | 23 | 19.5 | 32 | 24.3 | 20.8 | 34.9 |
| 10 | 1.5 | 20.1 | 16.2 | 28.4 | 22.4 | 18.1 | 31.9 |

[24]mole % EGDGE.

EXAMPLE 17

Preparation of a Multicomponent SAP Having a Poly(AA) Core Surrounded by a PEI Shell Sorbitan monooleate (0.81 g) was dissolved in 200 ml of heptane. Ten grams of crosslinked, unneutralized polyacrylic acid (180–425 μm) was added to this solution to act as seed for the core/shell composite particles. The resulting mixture was stirred at 700 rpm with a paddle stirrer. Polyethyleneimine (PEI) (27.6 g, 30% in water, $M_w$=750,000) was added to the polyacrylic acid/heptane slurry, followed immediately by the addition of 3.6 g of EGDGE. The EGDGE and PEI were allowed to cure for 4.5 hours at room temperature. The resulting SAP particles were allowed to settle, and the supernatant heptane was decanted. The SAP particles were rinsed three times with 100 ml of acetone. The SAP particles were allowed to dry overnight at room temperature, then further dried at 80° C. for 2 hours to yield 23.43 g of the multicomponent SAP particles.

The SAP particles of Example 17 then were tested for an ability to absorb synthetic urine under no load (AUNL) and under load (AUL) at 0.28 psi and 0.7 psi, in accordance with the previously described method. The results are summarized below:

| Surface Treatment | AUNL (1 hr) | AUL 0.28 psi, (1 hr) | AUL 0.7 psi (1 hr) | AUNL (3 hr) | AUL 0.28 psi, (3 hr) | AUL 0.7 psi (3 hr) |
|---|---|---|---|---|---|---|
| None | 15.22 | 12.09 | 10.38 | 15.78 | 13.12 | 11.74 |

EXAMPLE 18

Preparation of a Multicomponent SAP Having a Poly(AA) Core Surrounded by a Poly(vinylamine) Shell Sorbitan monooleate (1.88 g) was dissolved in 500 ml of heptane. Ten grams of crosslinked, unneutralized polyacrylic acid (180–425 μm) was added to this solution to act as seed for the core/shell composite particles. The resulting mixture was stirred at 700 rpm with a paddle stirrer. Poly (vinylamine) (84 g, 10.67% in water, $M_w$>100,000) was added to the polyacrylic acid/heptane slurry, followed immediately by the addition of 1.5 g of EGDGE. The EGDGE and poly(vinylamine) were allowed to cure for 6 hours at room temperature. The resulting SAP particles were allowed to settle, and the supernatant heptane was decanted. The SAP particles were rinsed three times with 200 ml of acetone. The SAP particles were dried at 80° C. for 3 hours to yield 17.89 g of the multicomponent SAP particles.

The SAP particles of Example 18 then were tested for an ability to absorb synthetic urine. The results are summarized below:

| Surface Treatment | AUNL (1 hr) | AUL 0.28 psi, (1 hr) | AUL 0.7 psi (1 hr) | AUNL (3 hr) | AUL 0.28 psi, (3 hr) | AUL 0.7 psi (3 hr) |
|---|---|---|---|---|---|---|
| None | 49.88 | 39.28 | 33.20 | 51.83 | 41.79 | 35.23 |

EXAMPLE 19

Preparation of a Multicomponent SAP Containing Agglomerated Poly(AA) and Poly(vinylamine)

An agglomeration solution containing the following ingredients was prepared:

| | |
|---|---|
| 0.25 g | EGDGE |
| 0.32 g | Aluminum sulfate |
| 0.31 g | Magnesium sulfate |
| 4.10 g | Water |
| 15.00 g | Propylene glycol. |

Under rapid agitation, 2.1 g of poly(vinylamine) (<180 μm, 5 mole % crosslinked with EGDGE) and 2.38 g of poly(AA) (<180 μm, 0.07 mole % crosslinked with MBA) were fluidized. With continued mixing, 0.84 g of the agglomeration solution was added to the fluidized powder blend. The resulting SAP particles were spread on a glass dish and dried at 125° C. for 2.5 hours.

The ability of the SAP particles to absorb and retain synthetic urine was determined. The results are summarized below:

| Surface Treatment | AUNL (1 hr) | AUL 0.28 psi, (1 hr) | AUL 0.7 psi (1 hr) | AUNL (3 hr) | AUL 0.28 psi, (3 hr) | AUL 0.7 psi (3 hr) |
|---|---|---|---|---|---|---|
| None | 55.09 | 40.40 | 31.22 | 56.71 | 41.01 | 37.80 |

EXAMPLE 20

Preparation of a Multicomponent SAP Comprising an Interpenetrating Polymer Network of Poly(AA) and Poly(vinylamine)

Reticulated poly(sodium acrylate) polymer beads (1.19 g) were acidified with 20 ml of 1M HCl, and allowed to stand for 1.5 hours. The poly(AA) beads then were filtered on a medium glass frit and rinsed with 50 ml of isopropyl alcohol. Air was drawn through the acidified poly(AA) beads for 0.5 hour to remove isopropyl alcohol from the pores of the poly(AA). The poly(AA) foam beads then were added to a premixed solution of 11.0 g of poly(vinylamine) (10.67%, $M_w$>100,000) and 0.24 g of EGDGE. The resulting mixture coagulated and was allowed to cure for 2 hours at 60° C. The resulting multicomponent SAP particles were spread on a dish and dried at 60° C. overnight to yield 2.8 g of the agglomerated SAP particles. A portion of the resulting multicomponent SAP particles was annealed at 125° C. for 1 hour to effect surface crosslinking. The remaining portion of the particles was not annealed. The ability of the IPN SAP particles of Example 20 were tested for an ability to absorb and retain synthetic urine. The results are summarized below:

| Surface Treatment | AUNL (1 hr) | AUL 0.28 psi, (1 hr) | AUL 0.7 psi (1 hr) | AUNL (3 hr) | AUL 0.28 psi, (3 hr) | AUL 0.7 psi (3 hr) |
|---|---|---|---|---|---|---|
| None | | | 22.1 | | | 22.4 |
| Annealing for 1 hr @ 125° C. | 32.8 | 25.2 | 21.7 | 34. | 22.9 | 22.8 |

EXAMPLE 21

Preparation of a Multicomponent SAP Comprising a Layer of Poly(AA) in Laminar Contact with a Layer of Poly(vinylamine)

To 186 g of 5 wt % poly(AA) ($M_w$ of about 1.25×10$^6$) in water was added 1.18 g of EGDGE, and the viscous solution was mixed thoroughly. Separately, 106 g of poly(vinylamine) (10.67%, $M_w$>100,000) and 2.3 g of EGDGE were quickly mixed and spread on a 9"×13" Teflon-coated metal sheet, then cured at 80° C. for 10 minutes. Next, the poly(AA) solution was spread on the poly(vinylamine) gel and allowed to cure and dry at 80° C. for 4 hours. The sheets shrunk during drying, and then the laminate was comminuted. A portion of the resulting multicomponent SAP particles was neither surface crosslinked nor annealed. A second portion was annealed at 125° C. for 1 hour. A third portion was surface crosslinked with PG/H$_2$O at 120° C. in an identical manner as Example 19. The SAP particles of Example 21 were tested for an ability to absorb and retain synthetic urine. The results are summarized below:

| Surface Treatment | AUNL (1 hr) | AUL 0.28 psi (1 hr) | AUL 0.7 psi (1 hr) | AUNL (3 hr) | AUL 0.28 psi (3 hr) | AUL 0.7 psi (3 hr) |
|---|---|---|---|---|---|---|
| None | 32.4 | 22.4 | 23.7 | 35.1 | 25.1 | 27 |
| Annealed for 1 hr @ 125° C. | 25.3 | 20.1 | 22.1 | 29.1 | 21.7 | 24.4 |
| Cross-linked with PG/H$_2$O (80/20) | 27 | 20.5 | 20.8 | 29.7 | 22.3 | 24.7 |

To demonstrate that a multicomponent SAP particles can contain an acidic resin and/or a basic resin that is partially neutralized, a series of is tests was performed on multicomponent SAP particles containing 45% by weight poly(AA) and 55% by weight poly(vinylamine). The multicomponent SAP particles were prepared as set forth in Example 12, but the percent neutralization of the poly(AA) and poly(vinylamine) was changed. The various multicomponent SAP particles were tested for an ability to absorb and retain synthetic urine, and the results are summarized in Table 7.

TABLE 7

| % Neutralized Poly(vinylamine)/ % Neutralized Poly(AA) (by weight) | Surface Crosslinking | AUL (0.7 psi, 1 hr) | AUL (0.7 psi, 3 hr) |
|---|---|---|---|
| 0/0 | None | 16.8 | 21.6 |
| 0/10 | None | 13.4 | 16.9 |
| 0/25 | None | 12.6 | 16 |
| 10/0 | None | 37.2 | 37.7 |
| 25/0 | None | 24.4 | 25.3 |
| 10/10 | None | 19.2 | 24.3 |
| 25/25 | None | 19.8 | 19.3 |
| 50/50 | None | 11.9 | 13.8 |
| 0/0 | PG/H$_2$O [25] | 43.3 | 47.6 |
| 0/10 | PG/H$_2$O | 34 | 36.9 |
| 0/25 | PG/H$_2$O | 14.4 | 17.4 |
| 10/0 | PG/H$_2$O | 30.9 | 31.4 |
| 25/0 | PG/H$_2$O | 24.1 | 25.3 |
| 10/10 | PG/H$_2$O | 39.3 | 41.2 |
| 25/25 | PG/H$_2$O | 18.9 | 18.7 |
| 50/50 | PG/H$_2$O | 12.1 | 14.5 |

[25] Surface treatment with propylene glycol/water (80/20 ratio) as set forth in Example 19.

In another series of tests, the ratio of acidic water-absorbing resin to basic water-absorbing resin in the multicomponent SAP particles was varied. In particular, Table 8 summarizes the AUNL data and the AUL data at different pressures for a series of multicomponent SAP particles containing poly(vinylamine) and poly(AA) over the range of 25% to 75% by weight. The multicomponent SAP particles used in this series of tests were prepared in accordance with the multicomponent SAP particles prepared in Example 12, and contained 55% by weight poly(vinylamine) and 45% by weight poly(acrylic acid). All multicomponent SAP particles used in the test were surface crosslinked with 50 ppm EGDGE. The multicomponent SAP particles were tested for an ability to absorb and retain synthetic urine.

TABLE 8

| Weight Ratio Poly(vinylamine)/Poly(AA) | AUL 0.28 psi (1 hr) | AUL 0.7 psi (1 hr) | AUL 1.4 psi (1 hr) | AUNL (1 hr) | AUL 0.28 psi (3 hr) | AUL 0.7 psi (3 hr) | AUL 1.4 psi (3 hr) | AUNL (3 hr) | AUL 0.28 psi (17 hr) | AUL 0.7 psi (17 hr) | AUL 1.4 psi (17 hr) | AUNL (17 hr) |
|---|---|---|---|---|---|---|---|---|---|---|---|---|
| 25/75 | 41.3 | 36.6 |  | 53.6 | 41.2 | 36.6 |  | 54 | 39.1 | 33.3 |  | 52.3 |
| 30/70 | 46.3 | 42.2 |  | 58.7 | 46.4 | 42.8 |  | 59.6 | 43.1 | 38.7 |  | 58.4 |
| 35/65 | 43.6 | 38.5 |  | 54.4 | 44.2 | 39.5 |  | 54.8 | 42 | 35.8 |  | 54.3 |
| 40/60 | 52.1 | 44.3 |  | 63.9 | 53.7 | 46.5 |  | 66.7 | 51.7 | 43.2 |  | 65.2 |
| 45/55 | 50.4 | 46 |  | 61.1 | 51.4 | 47.4 |  | 63.2 | 47.3 | 41.9 |  | 61.9 |
| 50/50 | 52.2 | 45 | 26 | 62.5 | 54.8 | 47.7 | 29 | 66.7 | 52.8 | 45.4 | 30.9 | 66.4 |
| 55/45 | 52.1 | 47.3 | 27.4 | 62.5 | 54.8 | 49.3 | 31.3 | 66.2 | 53.1 | 44.8 | 32.5 | 65.4 |
| 60/40 | 52.8 | 47 | 27.8 | 64.6 | 55.2 | 49.6 | 30.9 | 68 | 52.6 | 44 | 33 | 67.6 |
| 65/35 | 50 | 45.9 |  | 59.2 | 51.6 | 47.3 |  | 61.8 | 48.8 | 41 |  | 61.4 |
| 70/30 | 47.5 | 43.1 |  | 57.4 | 48.3 | 43.8 |  | 59.4 | 43.5 | 37.2 |  | 56.7 |
| 75/25 | 43.9 | 39.3 |  | 53.6 | 43.9 | 39.2 |  | 54.8 | 38.9 | 31.2 |  | 51.4 |

In another series of tests, multicomponent SAP particles containing 45% poly(AA) and 55% poly(vinylamine) by weight were prepared as set forth in Example 12. The multicomponent SAP particles were prepared by extruding the blended gels of acidic resin and basic resin using a KitchenAid mixer (as a control), or using a Brabender twin screw extruder containing both mixing and conveying elements. In some tests, additional back pressure was provided by a breaker plate and/or a screen. The speed of the Brabender extruder was varied. Both untreated and surface treated (i.e., PG/H$_2$O 80/20) multicomponent SAP particles were tested. The various samples were tested for an ability to absorb synthetic urine. The results, summarized in Table 9, show that the more intimate blending provided by the Brabender extruder improved the absorption and retention properties of the SAP particles.

TABLE 9

| Method of Extrusion | Surface Treatment | AUNL (1 hr) | AUL 0.28 psi (1 hr) | AUL 0.7 psi (1 hr) | AUNL (3 hr) | AUL 0.28 psi (3 hr) | AUL 0.7 psi (3 hr) |
|---|---|---|---|---|---|---|---|
| KitchenAid (control) | None | 69.6 | 33 | 15.4 | 73.3 | 39.3 | 21.7 |
| Brabender-no plate 25 rpm | None | 71.4 | 41.7 | 13.9 | 74.7 | 46.6 | 19.6 |
| Brabender-no plate 100 rpm | None | 70.7 | 43.5 | 15.5 | 73.8 | 56.2 | 23.6 |
| Brabender-plate 25 rpm | None | 72 | 46.7 | 16 | 74.1 | 55.1 | 22.1 |
| Brabender-plate 100 rpm | None | 70.5 | 48.4 | 16.9 | 72.6 | 60 | 23.2 |
| Brabender-plate 150 rpm | None | 69.7 | 50.5 | 29.5 | 72.1 | 59.3 | 35.4 |
| Brabender-plate 40 mesh screen 25 rpm | None | 70.5 | 54.4 | 16.3 | 73.3 | 59.7 | 23.9 |
| Brabender-plate 40 mesh screen 150 rpm | None | 68.9 | 57.7 | 33.2 | 69 | 59.9 | 42.1 |
| KitchenAid (control) | PG/H$_2$O 80/20 | 64.3 | 51.9 | 40.3 | 69.9 | 55.7 | 44 |
| Brabender-no plate 25 rpm | PG/H$_2$O 80/20 | 66.2 | 53.7 | 42 | 70.4 | 56.9 | 44.6 |
| Brabender-no plate 100 rpm | PG/H$_2$O 80/20 | 65.4 | 52.8 | 41.6 | 68.8 | 56.1 | 45.4 |
| Brabender-plate 25 rpm | PG/H$_2$O 80/20 | 66.8 | 53.7 | 42.3 | 70.4 | 56.9 | 45.5 |
| Brabender-plate 100 rpm | PG/H$_2$O 80/20 | 66 | 53 | 44 | 68.8 | 55.5 | 47.6 |
| Brabender-plate 150 rpm | PG/H$_2$O 80/20 | 65.5 | 52.3 | 44.6 | 67.8 | 54.5 | 47.2 |
| Brabender-plate 40 mesh screen 25 rpm | PG/H$_2$O 80/20 | 65.2 | 54 | 45.6 | 68.3 | 56.2 | 49.1 |
| Brabender-plate 40 mesh screen 150 rpm | PG/H$_2$O 80/20 | 63.5 | 50.7 | 44.2 | 64.9 | 53.1 | 47.1 |

In addition to an ability to absorb and retain relatively large amounts of a liquid, it also is important, particularly when contained in a sheet material, wherein the SAP particles are partially hydrated and/or heated to at least 50° C., compressed together to achieve adhesion of adjacent particles, for an SAP to exhibit good permeability, and, therefore, rapidly absorb the liquid. Therefore, in addition to absorbent capacity, or gel volume, useful SAP particles also have a high gel strength, i.e., the swelled (hydrated) particles resist deformation after absorbing a liquid. In addition, the permeability or flow conductivity of a hydrogel formed when SAP particles swell, or have already swelled, in the presence of a liquid is extremely important property for practical use of the SAP particles in a water-absorptive sheet material. Differences in permeability or flow conductivity of the absorbent polymer can directly impact on the ability of an absorbent sheet material article to acquire and distribute body fluids.

Many types of SAP particles exhibit gel blocking. "Gel blocking" occurs when the SAP particles are wetted and swell, which inhibits fluid transmission to the interior of the SAP particles and between absorbent SAP particles. Wetting of the interior of the SAP particles or the absorbent structure as a whole, therefore, takes place via a very slow diffusion process, possibly requiring up to 16 hours for complete fluid absorption. In practical terms, this means that acquisition of a fluid by the SAP particles, and, accordingly, the absorbent structure, such as a diaper, can be much slower than the rate at which fluids are discharged, especially in gush situations. Leakage from an absorbent structure, therefore, can occur well before the SAP particles in the absorbent structure are fully saturated, or before the fluid can diffuse or wick past the "gel blocked" particles into the remainder of the absorbent structure. Gel blocking can be a particularly acute problem if the SAP particles lack adequate gel strength, and deform or spread under stress after the SAP particles swell with absorbed fluid.

Accordingly, an SAP particle can have a satisfactory AUL value, but will have inadequate permeability or flow conductivity to be useful at high concentrations in absorbent structures. In order to have a high AUL value, it is only necessary that the hydrogel formed from the SAP particles has a minimal permeability such that, under a confining pressure of 0.3 psi, gel blocking does not occur to any significant degree. The degree of permeability needed to simply avoid gel blocking is much less than the permeability needed to provide good fluid transport properties. Accordingly, SAPs that avoid gel blocking and have a satisfactory AUL value can still be greatly deficient in these other fluid handling properties.

Accordingly, an important characteristic of the sheet materials of the present invention, containing multicomponent SAP particles or a combination of a single component acidic resin and a single component basic resin, is permeability when swollen with a liquid to form a hydrogel zone or layer, as defined by the Saline Flow Conductivity (SFC) value of the SAP particles. SFC measures the ability of an SAP to transport saline fluids, such as the ability of the hydrogel layer formed from the swollen SAP to transport body fluids. A material having relatively high SFC value is an air-laid web of wood pulp fibers. Typically, an air-laid web of pulp fibers (e.g., having a density of 0.15 g/cc) exhibits an SFC value of about $200 \times 10^{-7}$ cm$^3$sec/g. In contrast, typical hydrogel-forming SAPs exhibit SFC values of $1 \times 10^{-7}$ cm$^3$sec/g or less. When an SAP is present at high concentrations in an absorbent structure, as in the articles of the present invention, and then swells to form a hydrogel under usage pressures, the boundaries of the hydrogel come into contact, and interstitial voids in this high SAP concentration region become generally bounded by hydrogel. When this occurs, the permeability or saline flow conductivity properties in this region is generally indicative of the permeability or saline flow conductivity properties of a hydrogel zone formed from the SAP alone. Increasing the permeability of these swollen high concentration regions to levels that approach or even exceed conventional acquisition/distribution materials, such as wood pulp fluff, can provide superior fluid handling properties for the absorbent structure, thus decreasing incidents of leakage, especially at high fluid loadings.

The sheet materials of the present invention include SAP particles having an SFC value that approach or exceed the SFC value of an air-laid web of wood pulp fibers. This is particularly important in the sheet materials of the present invention containing high, localized concentrations of SAP particles in an absorbent structure. High SFC values also indicate an ability of the resultant hydrogel to absorb and retain body fluids under normal usage conditions.

The SFC value of the multicomponent SAP particles are substantially improved over the SFC value for a standard poly(AA) SAP, as illustrated in the data summarized in Table 10. A method for determining the SFC value of SAP particles is set forth in Goldman et al. U.S. Pat. No. 5,599,335, incorporated herein by reference.

TABLE 10

| Time (min) | Sample 1 (Control)[26] AUL 0.7 psi | Sample 2 (Comparative)[27] AUL 0.7 psi | Sample 3[28] AUL 0.7 psi | Sample 4[29] AUL 0.7 psi | Sample 5[30] AUL 0.7 psi | Sample 6[31] AUL 0.7 psi | Sample 7[32] AUL 0.7 psi |
|---|---|---|---|---|---|---|---|
| 0 | 0 | 0 | 0 | 0 | 0 | 0 | 0 |
| 5 | 25.3 | 14.8 | 26 | 26.3 | 17.8 | 19.3 | 13.6 |
| 10 | 30.7 | 20.9 | 33.2 | 34.5 | 23.4 | 20.4 | 16.2 |
| 15 | 32.1 | 25.1 | 37.9 | 38.8 | 26.3 | 21 | 17.4 |
| 30 | 33.8 | 31.2 | 43.3 | 44.1 | 29.9 | 20.8 | 17.6 |
| 45 | 34.2 | 34.3 | 45.8 | 45.6 | 31.8 | 21.6 | 19.3 |
| 60 | 34.5 | 36.4 | 47.6 | 46.2 | 32.4 | 21.7 | 20.1 |
| 120 | 35.2 | 40 | 49.1 | 47.6 | 33.6 | 22.3 | 20.5 |
| 180 | 35.2 | 42.3 | 49.7 | 48 | 35.6 | 22.8 | 21.7 |
| SFC[33] | 15 | 115 | 368 | 685 | 707 | 534 | 930 |

[26] Standard, commercial SAP, i.e., neutralized poly(AA), 75% DN, available as A2300, from Chemdal, Corp., Palatine, IL;
[27] Comparative sample containing a dry blend of 55% by weight unneutralized poly(vinylamine) particles and 45% by weight unneutralized poly(AA) particles;
[28] Multicomponent SAP particles of the present invention, containing 55% unneutralized poly(vinylamine) and 55% poly(AA), prepared in a KitchenAid mixer in accordance with Example 12;
[29] Multicomponent SAP particles of the present invention, containing 55% unneutralized poly(vinylamine) and 45% poly(AA), prepared in accordance with Example 12;
[30] Multicomponent SAP particles of the present invention, containing 55% unneutralized poly(vinylamine) and 45% poly(AA), prepared in accordance with Example 18;
[31] Multicomponent SAP particles of the present invention, containing 55% unneutralized poly(vinylamine) and 45% poly(AA), prepared in accordance with Example 20;
[32] Multicomponent SAP particles of the present invention, containing 55% unneutralized poly(vinylamine) and 45% poly(AA), prepared in accordance with Example 21; and
[33] in $\times 10^{-7}$ cm$^3$ sec/g.

The data summarized in Table 10 shows a substantial improvement in AUL at 0.7 psi and SFC for multicomponent particles of the present invention in comparison to a control SAP and a comparative dry blend of SAP particles. Accordingly, multicomponent SAP particles have an SFC value of at least about $150 \times 10^{-7}$ cm$^3$sec/g, and preferably at least about $250 \times 10^{-7}$ cm$^3$sec/g. To achieve the full advantage of the present invention, the SFC value of the multicomponent particles incorporated into the sheet materials of the present invention is at least about $350 \times 10^{-7}$ cm$^3$sec/g, and can range to greater than $1000 \times 10^{-7}$ cm$^3$sec/g.

Figure 8:
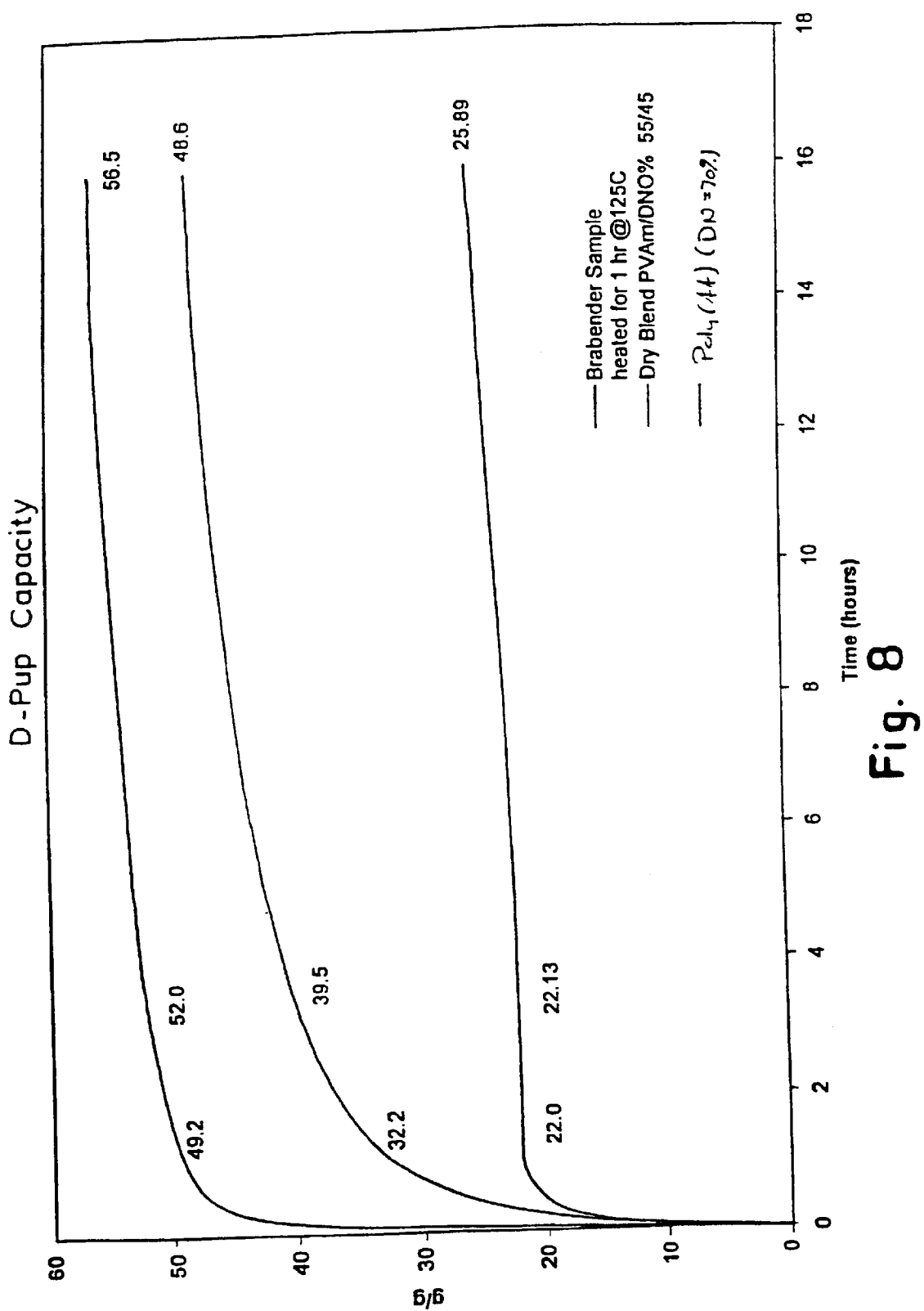
FIGS. 8 and 9 contain plots of PUP at 0.7 psi (in g/g) vs. time (hrs) for present multicomponent SAP particles and prior art SAPs.

The multicomponent SAP particles, and their separated acidic and basic resin components, also exhibit excellent diffusion of a liquid through and between the particles. FIG. 8 contains plots of Performance Under Pressure (PUP) capacity at 0.7 psi over time for a dry blend of 55% unneutralized poly(vinylamine) and 45% unneutralized poly(AA), for a standard commercial poly(AA) SAP, and for the multicomponent SAP. The PUP capacity test is similar to the AUL test, but the SAP particles are allowed to absorb a fluid on demand. The PUP test is designed to illustrate absorption kinetics of an SAP particle.

In contrast, the plots of FIG. 8 illustrate that the multicomponent SAP particles (i.e., 55/45 weight ratio unneutralized poly(vinylamine)/poly(AA) particles prepared using a Brabender extruder in accordance with Example 12 and annealed for 1 hour at 125° C.) essentially attain their absorptive capacity after 1 hour, and have attained their absorptive capacity after 3 hours. The plots show that after 3 hours, the PUP capacity of the dry blend has not been attained. The multicomponent SAP particles, therefore, demonstrate a faster absorption of liquids, and a better diffusion rate of liquids into and through the particles, in addition to an ability to absorb and retain a greater amount of liquids than typical SAP products.

FIG. 8 also shows that a standard poly(AA) attains an absorptive capacity quickly, but does not absorb and retain as much of the electrolyte-containing liquid. Overall, FIG. 8 shows that the multicomponent SAPs exhibit both a) improved absorption and retention, and b) improved permeability and absorption kinetics.

Figure 9:
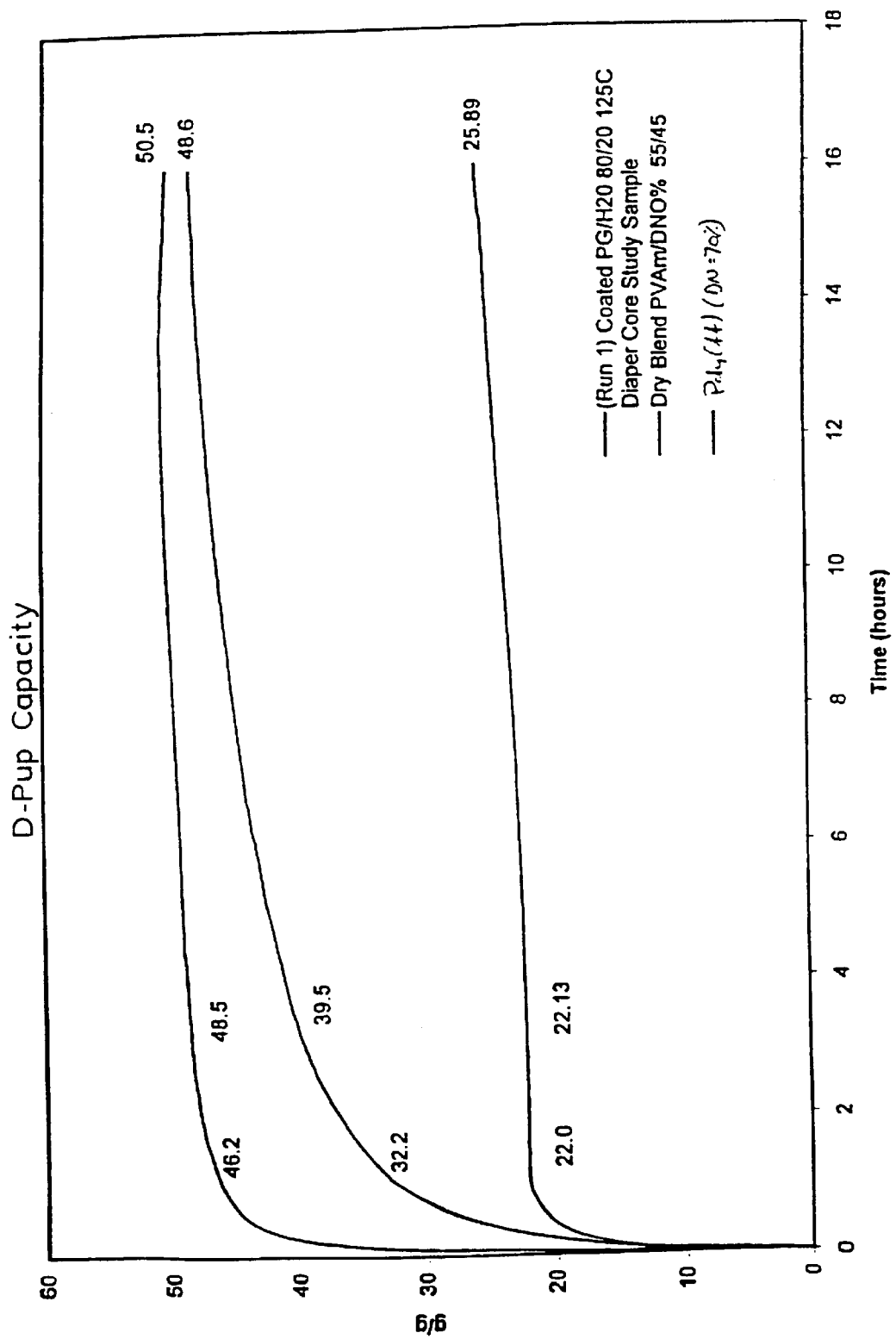

FIG. 9 contains similar plots again showing improved absorption, retention, permeability, and absorption kinetics for a multicomponent SAP particle identical to those used in FIG. 8, except the particles tested in FIG. 9 were surface coated with 80/20 PG/H$_2$O and heated at 125° C. for 1 hour.

Figure 10:
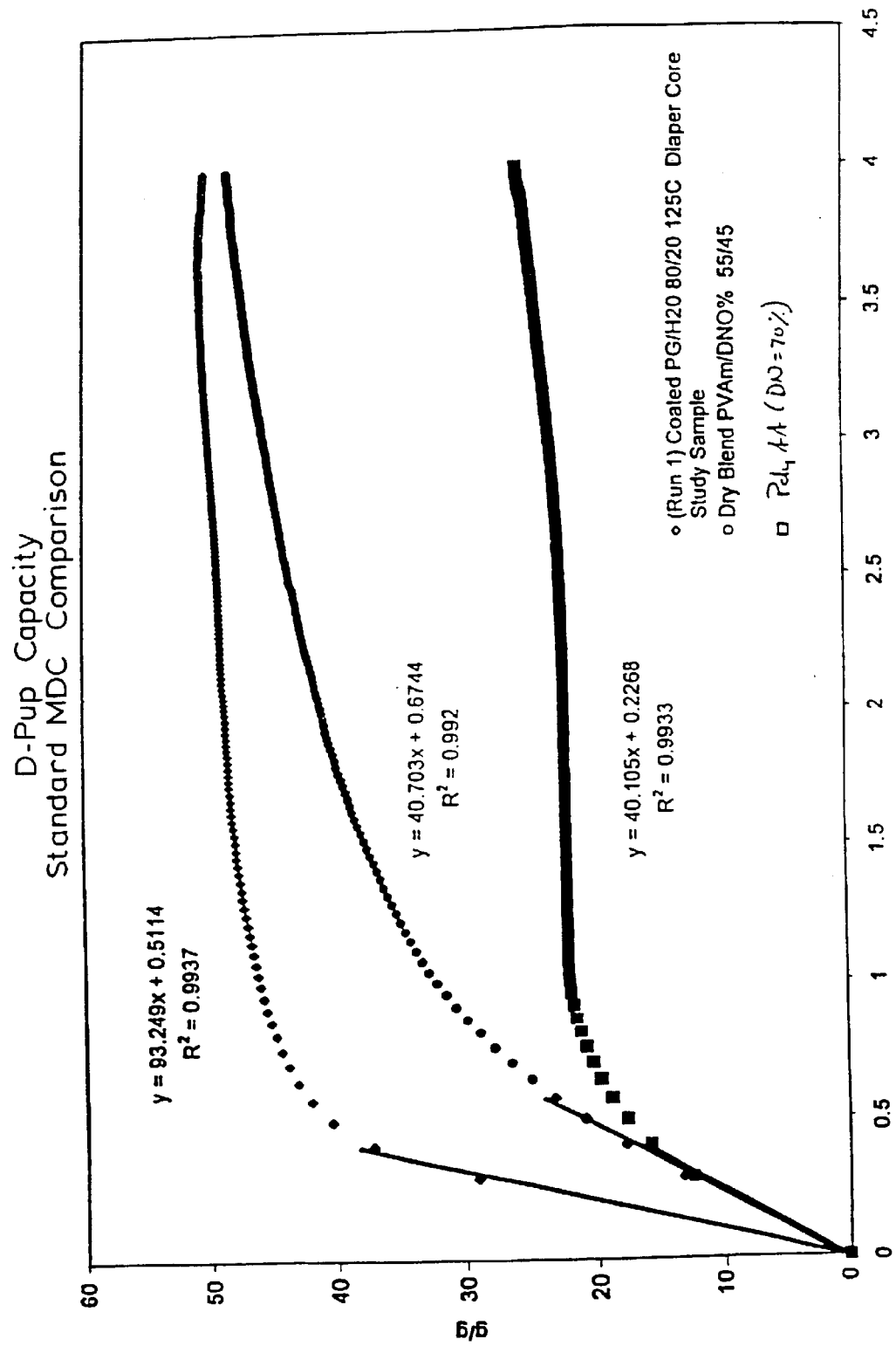
FIGS. 10 and 11 contain plots for initial Performance Under Pressure (PUP) capacity vs. $t^{1/2}$ for present multicomponent SAP particles and prior art SAPs.
Figure 11:
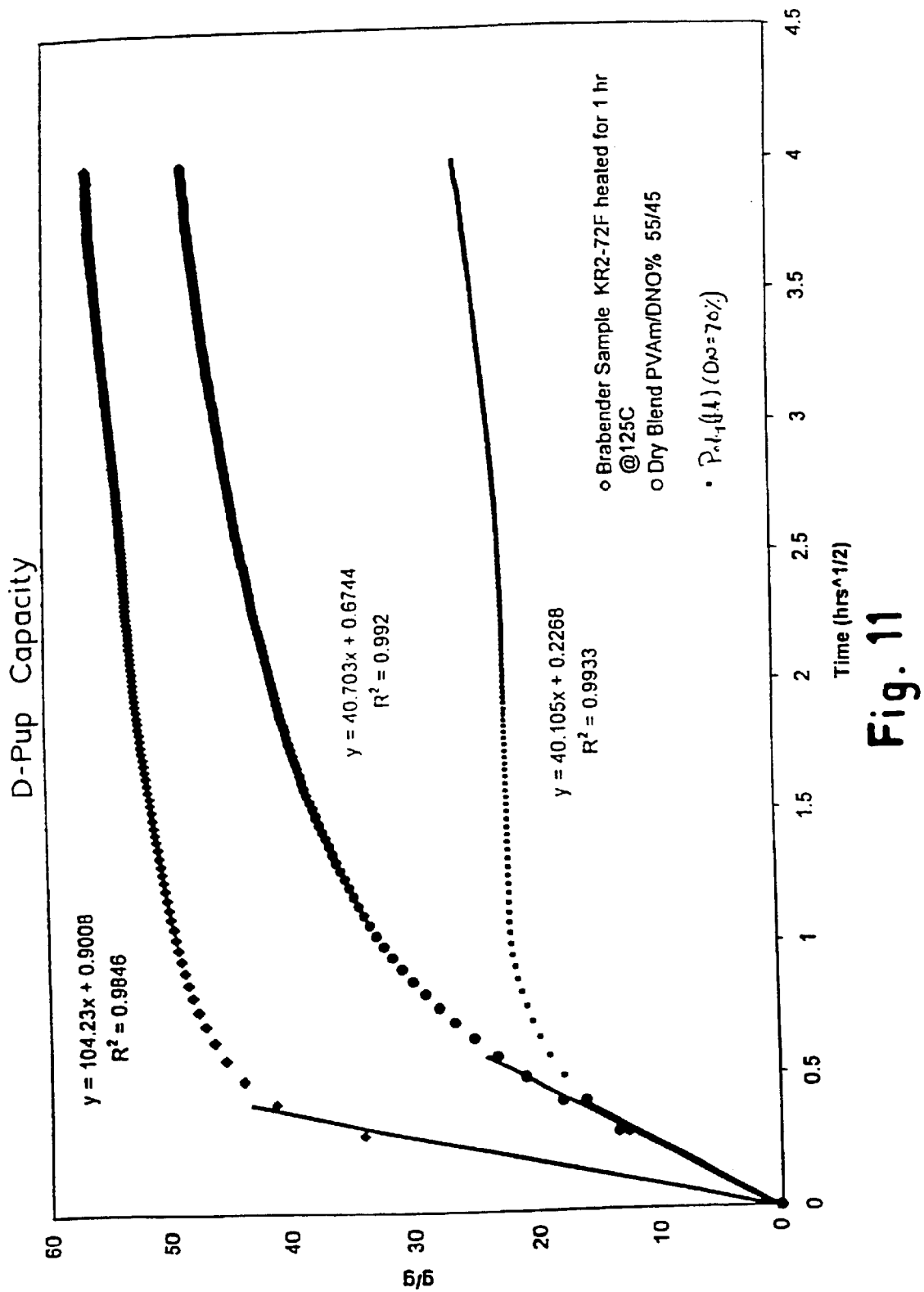

FIGS. 10 and 11 illustrate the improved initial performance under pressure (PUP) capacity rate for multicomponent SAP particles. FIG. 10 shows the comparative initial PUP capacity rate for absorbency vs. (time) $^{1/2}$ for 16 hours between multicomponent SAP particles containing a 55/45 weight ratio of poly(vinylamine) and poly(acrylic acid) surface crosslinked with 80/20 PG/H$_2$O, a dry blend of poly(vinylamime) and poly(acrylic acid), and a standard 75% neutralized poly(AA) SAP. The plots in FIG. 10 provide a better measurement of the initial slope of the plots, and, therefore, provides a more meaningful comparison of initial PUP capacity rate.

The plots in FIG. 10 show a substantially improved initial PUP capacity rate for the multicomponent SAP particles prepared using a KitchenAid mixer (93.2 g/g/hr$^{1/2}$) compared to a dry blend of SAP particles (40.7 g/g/hr$^{1/2}$) and to a standard poly(AA) (40.1 g/g/hr$^{1/2}$). FIG. 11 shows similar results for multicomponent SAP particles prepared in a Brabender extrusion apparatus and annealed for 1 hour at 125° C, i.e., initial PUP capacity of 104.2 g/g/hr$^{1/2}$.

The multicomponent SAP particles, therefore, have an initial PUP capacity rate of at least 50 g/g/hr$^{1/2}$, and preferably at least 70 g/g/hr$^{1/2}$. To achieve the full advantage of the present invention, the multicomponent SAP particle has an initial PUP capacity rate of greater than 90 g/g/hr$^{1/2}$, and preferably greater than 100 g/g/hr$^{1/2}$.

In another test, the free swell rate (FSR) of a multicomponent SAP particle was compared to the FSR of a standard poly(AA) SAP and 55/45 weight ratio of a poly(vinylamine)/poly(acrylic acid) dry particle blend. The FSR test, also known as a lock-up test, is well known to persons skilled in the art.

The multicomponent SAP particle had an FSR (in g/g/sec) of 0.49 and 0.48, for 55/45 weight ratio multicomponent SAP particles made in a KitchenAid mixer and a Brabender extruder, respectively. In comparison, a dry blend had an FSR of 0.10 and a standard neutralized poly(AA) had an FSR of 0.32. Multicomponent SAP particles therefore, have an FSR of greater than 0.35, preferably greater than 0.40, and most preferably greater than 0.45. These data further show the improved ability of the multicomponent SAP particles to absorb and retain larger amounts of an electrolyte-containing liquid quickly and in sheet material form.

The multicomponent SAP particles also can be mixed with particles of a second (single component) water-absorbing resin to provide an SAP material having improved absorption properties. The second water-absorbing resin can be an acidic water-absorbing resin, a basic water-absorbing resin, or a mixture thereof. The SAP material comprises about 10% to about 90%, and preferably about 25% to about 85%, by weight, multicomponent SAP particles and about 10% to about 90%, and preferably, about 25% to about 85%, by weight, particles of the second water-absorbing resin. More preferably, the SAP material contains about 30% to about 75%, by weight, multicomponent SAP particles. To achieve the full advantage of the present invention, the SAP material contains about 35% to about 75%, by weight, the multicomponent SAP particles. The multicomponent SAP particles can be prepared by any of the previously described methods, e.g., extrusion, agglomeration, or interpenetrating polymer network, and can be of any shape, e.g., granular, fiber, powder, or platelets.

The second water-absorbing resin can be any of the previously discussed acidic resins used in the preparation of the blended or multicomponent SAP particles. The second water-absorbing resin, either acidic or basic, can be unneutralized (DN=0), partially neutralized (0<DN<100), or completely neutralized (DN=100). A preferred acidic water-absorbing resin used as the second resin is polyacrylic acid, preferably partially neutralized polyacrylic acid, e.g., DN about 50%, and preferably about 70% up to about 100%. The second water-absorbing resin also can be any of the previously discussed basic resins used in the preparation of a multicomponent SAP. Preferred basic water-absorbing resins used as the second resin are poly(vinylamine) or a poly(dialkylaminoalkyl(meth)acrylamide). Blends of acidic resins, or blends of basic resins, can be used as the second water-absorbing resin. Blends of an acidic resin and a basic resin also can be used as the second water-absorbing resin.

To illustrate the improved absorption properties demonstrated by an SAP material comprising multicomponent SAP particles and particles of a second water-absorbing resin, mixtures of multicomponent SAP particles and partially neutralized (DN=70) polyacrylic acid (poly(AA)) particles were prepared. As used here and throughout the specification poly(AA) (DN=70) refers to a standard, commercial poly(AA) neutralized about 70% to about 80%, and poly(AA)(DN=0) refers to unneutralized poly(AA). The multicomponent SAP particles contain microdomains of poly(vinylamine) dispersed in poly(AA) (DN=0). The poly(vinylamine)/poly(AA) weight ratio of the multicomponent SAP particles was 55/45. The resulting SAP material was tested for an ability to absorb synthetic urine under load at 0.7 psi, in accordance with the previously described method. The results are summarized below:

| wt ratio[1] | AUL 0.7 psi (1 hr.) | AUL 0.7 psi (3 hr.) | SFC (× 10$^{-7}$ cm$^3$ sec/g) |
|---|---|---|---|
| 100/0 | 26.7 | 27.1 | 14 |
| 75/25 | 30.2 | 30.7 | 26 |
| 50/50 | 36.7 | 37.7 | 72 |
| 25/75 | 40.8 | 42.6 | 189 |
| 0/100 | 43.0 | 46.4 | 787 |

[1]weight ratio of partially neutralized poly(AA) particles to multicomponent SAP particles.

The data presented above shows a substantial improvement in absorption properties achieved by an SAP material comprising a blend of multicomponent SAP particles and particles of a second, single-component water-absorbing resin over conventional, partially neutralized poly(AA). The improved results are more clearly demonstrated by comparing the data presented above to the data summarized in the following Table 11, which contains absorption under load data for various mixtures of acidic and basic water-absorbing resins that lack a multicomponent SAP.

TABLE 11

| Example | Blend Ratio[5] | AUL 0.7 psi (1 hr) | AUL 0.7 psi (3 hr) |
|---|---|---|---|
| 1[1] | 75/25 | 27.1 | 28.9 |
| 1 | 50/50 | 30.9 | 33 |
| 1 | 25/75 | 35.9 | 40.2 |
| 2[2] | 75/25 | 26.6 | 27.3 |
| 2 | 50/50 | 28.7 | 30.3 |
| 2 | 25/75 | 26.3 | 27.3 |
| 3[3] | 75/25 | 25.3 | 26 |
| 3 | 50/50 | 21.3 | 22.8 |
| 3 | 25/75 | 15.7 | 16.4 |
| 4[4] | 55/45 | 37 | 45.2 |

[1] Blend of (a) partially neutralized poly(AA) (DN = 70) and (b) a mixture containing 55% by weight poly(vinylamine) and 45% by weight poly(AA) (DN = 0);
[2] Blend of (a) partially neutralized poly(AA) (DN = 70) and (b) poly(vinylamine);
[3] Blend of (a) partially neutralized poly(AA) (DN = 70) and (b) poly(AA) (DN = 0);
[4] Blend of (a) poly(vinylamine) and (b) poly(AA) (DN = 0); and
[5] Weight ratio of (a) to (b) in each blend.

Table 12 contains additional AUL data at 0.7 psi showing the substantially improved absorption properties and SFC for blends containing particles of a multicomponent SAP. In particular, the data in Table 12 shows that an SAP material comprising a blend of multicomponent SAP particles and particles of a second, single-component water-absorbing resin (i.e., Samples 5–7) greatly outperformed a standard poly(AA) absorbent resin (i.e., Sample 1) and a dry blend of water-absorbing resins (i.e., Samples 2 and 3). The blend of multicomponent SAP particles and particles of a second water-absorbing resin also performed well compared to an absorbent containing 100% multicomponent SAP particles.

Figure 14:
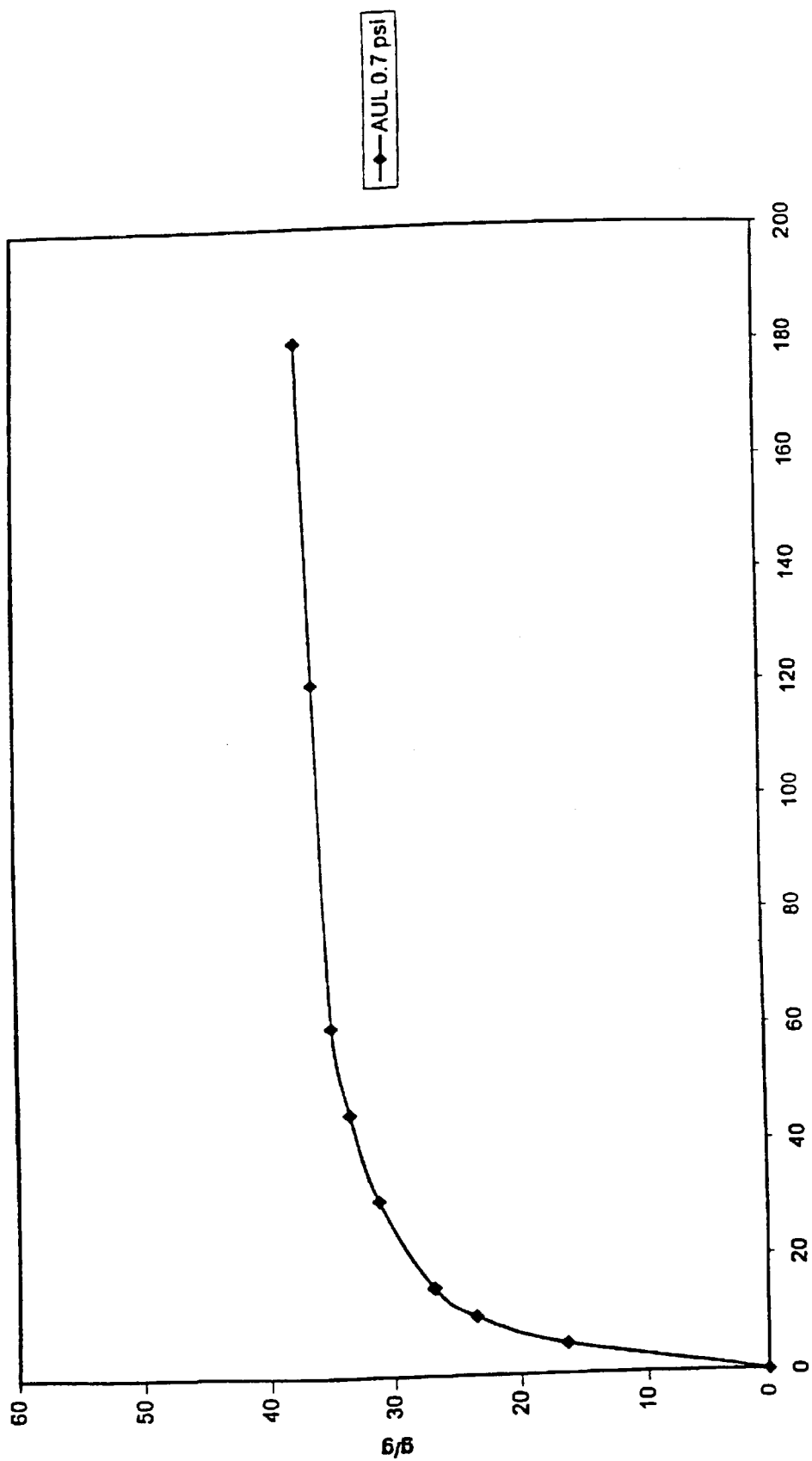
FIGS. 14–17 are plots of absorbance (in g/g) vs. time (minutes) for a variety of blends of superabsorbent particles.
Figure 15:
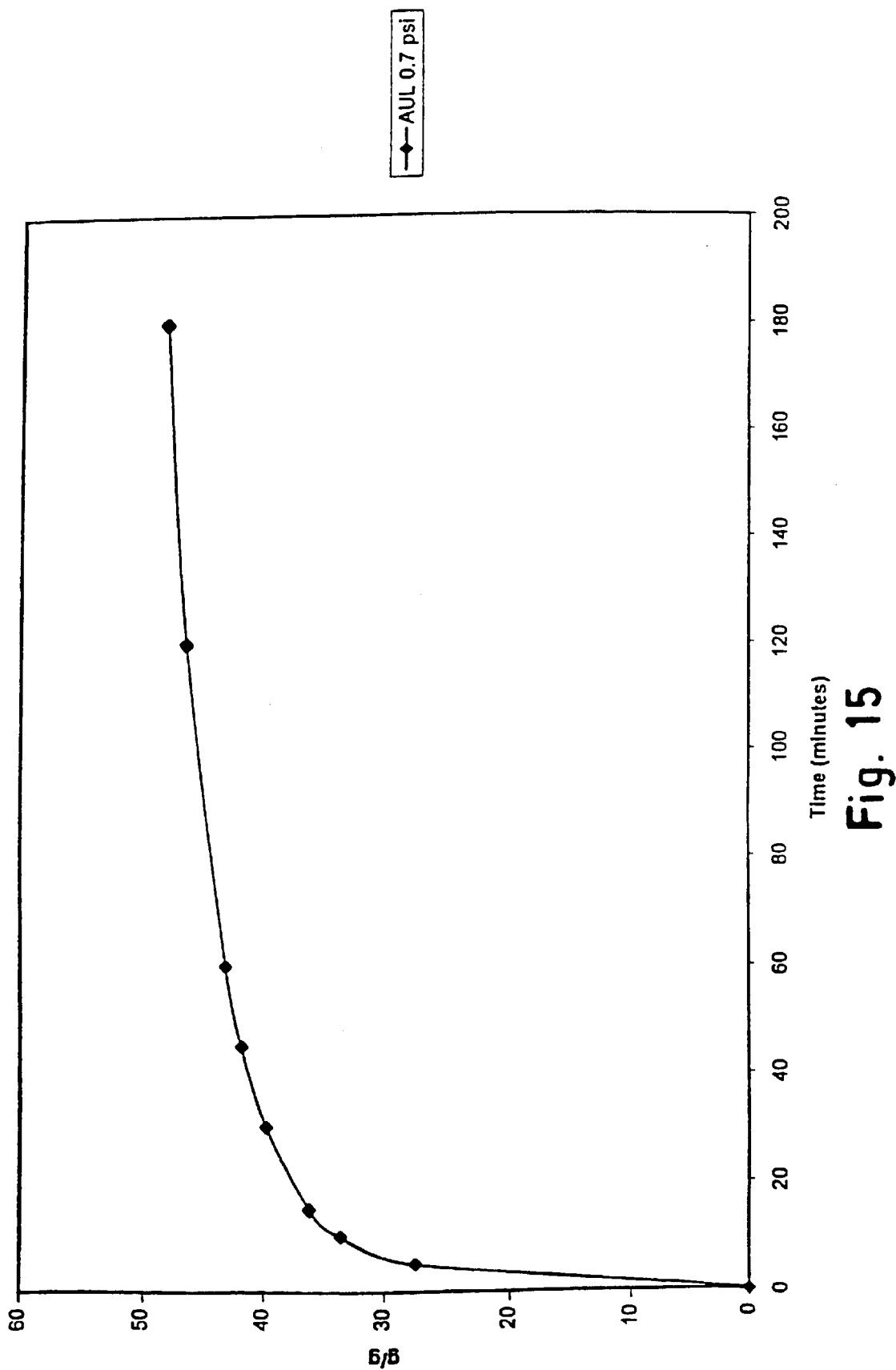
Figure 16:
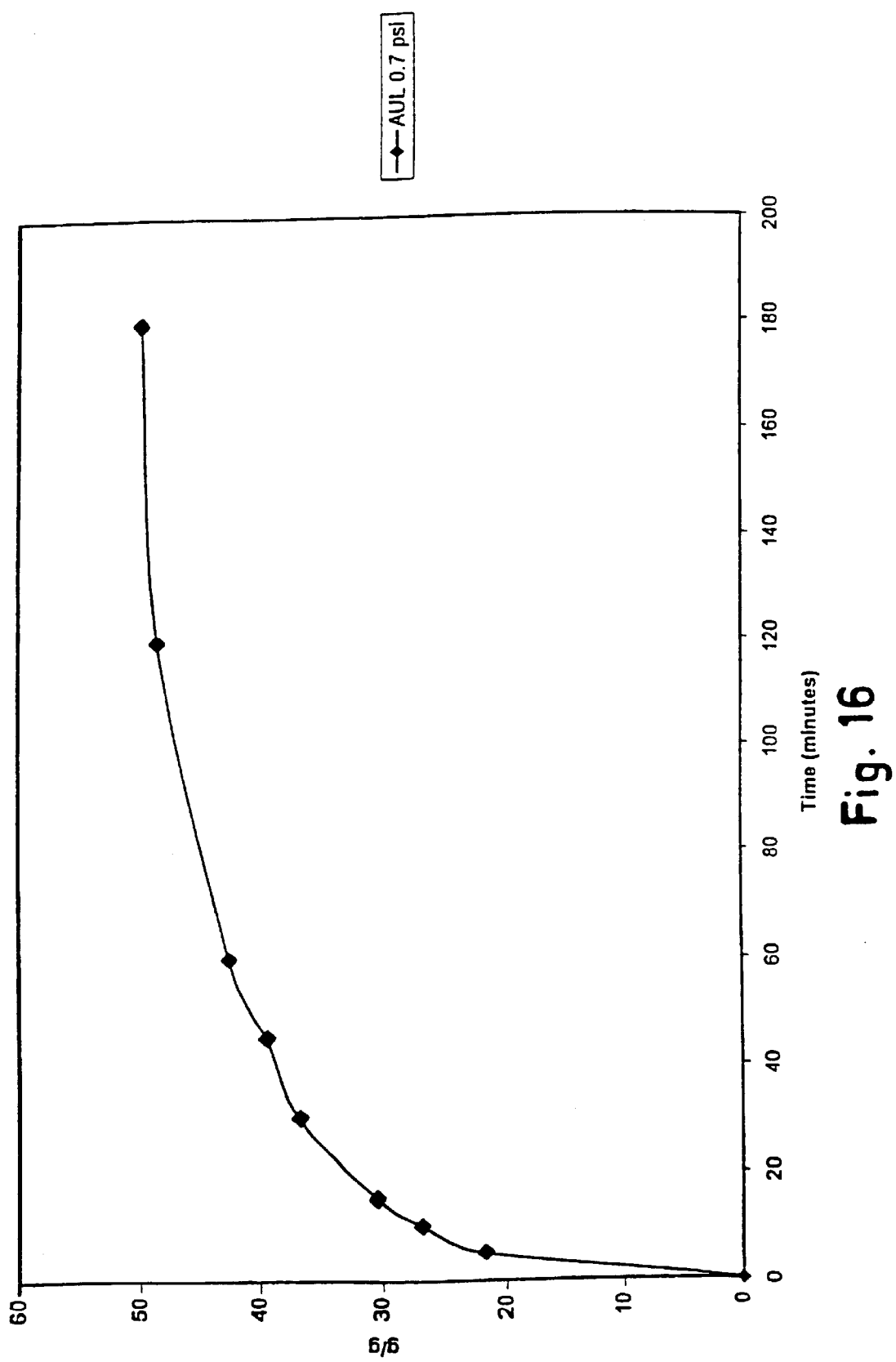
Figure 17:
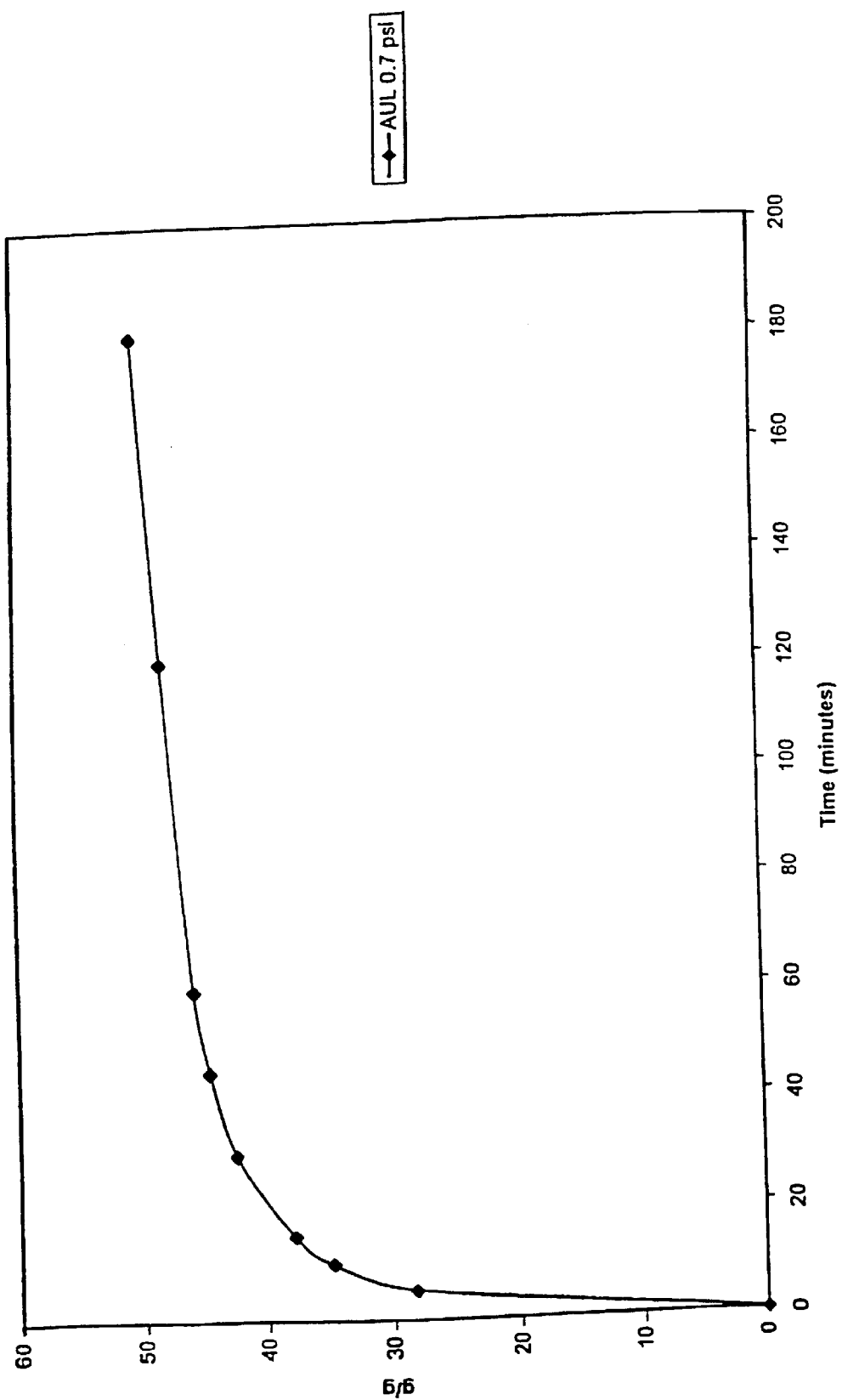

FIGS. 14–17 contain plots of absorbance (g/g) vs. time for various SAP materials and dry blends. FIG. 14 illustrates the absorption properties for a dry blend of poly(AA) (DN=70), poly(vinylamine), and poly(AA) (DN=0). The results in FIG. 14 are inferior to the results summarized in FIG. 15, which illustrate the absorption properties for an SAP material containing 80% multicomponent SAP, 11% poly(vinylamine), and 9% poly(AA) (DN=70). FIGS. 16 and 17 also show improved absorption properties for a blend of 90% multicomponent SAP and 10% poly(vinylamine) (FIG. 16) and for a blend of 90% multicomponent SAP and 10% poly(AA) (DN=0) (FIG. 17).

Figure 18:
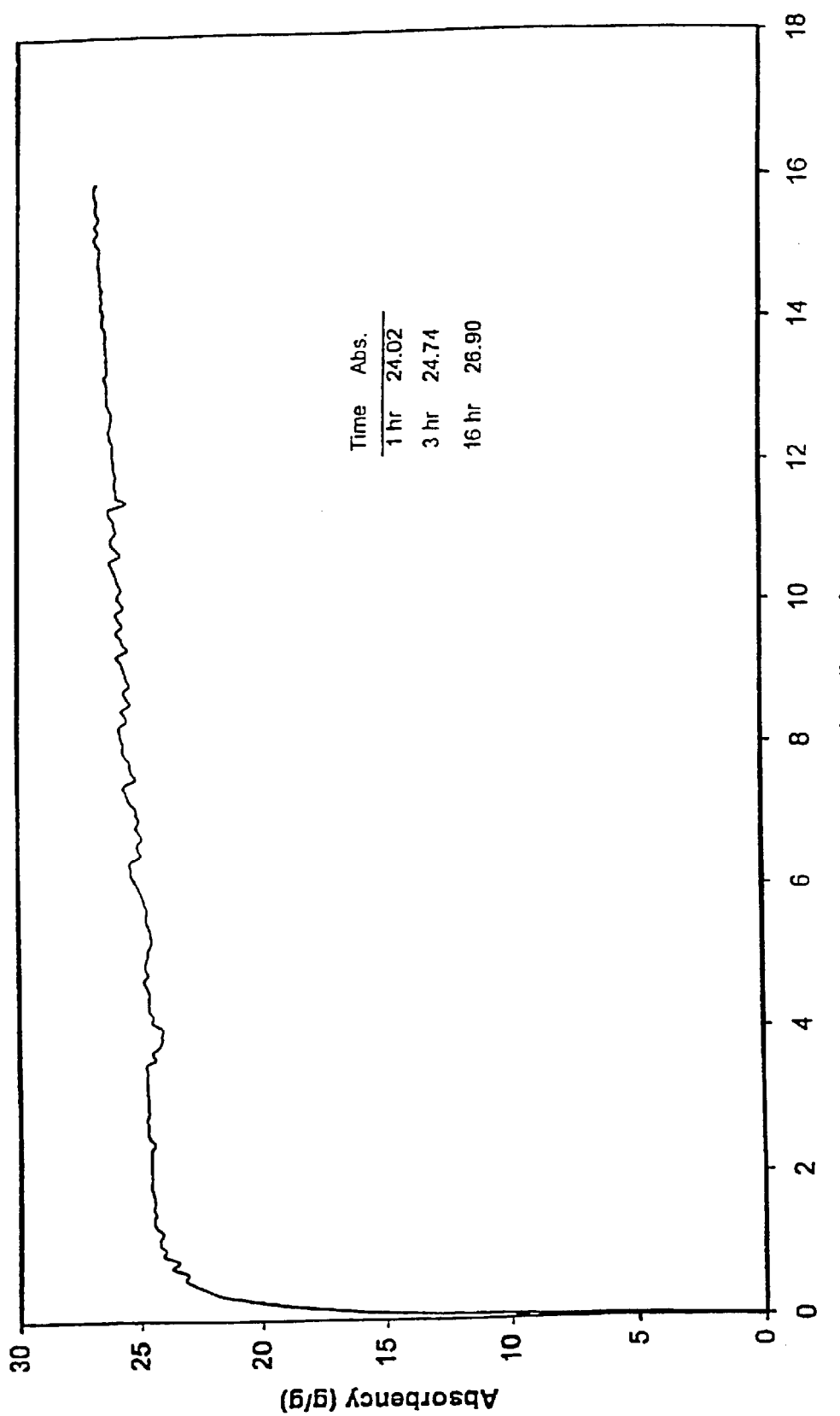
FIG. 18 is a plot of PUP at 0.7 psi vs. time (hrs) for a superabsorbent material containing 25% multicomponent SAP particles and 75% poly(AA)(DN=70), by weight.
Figure 19:
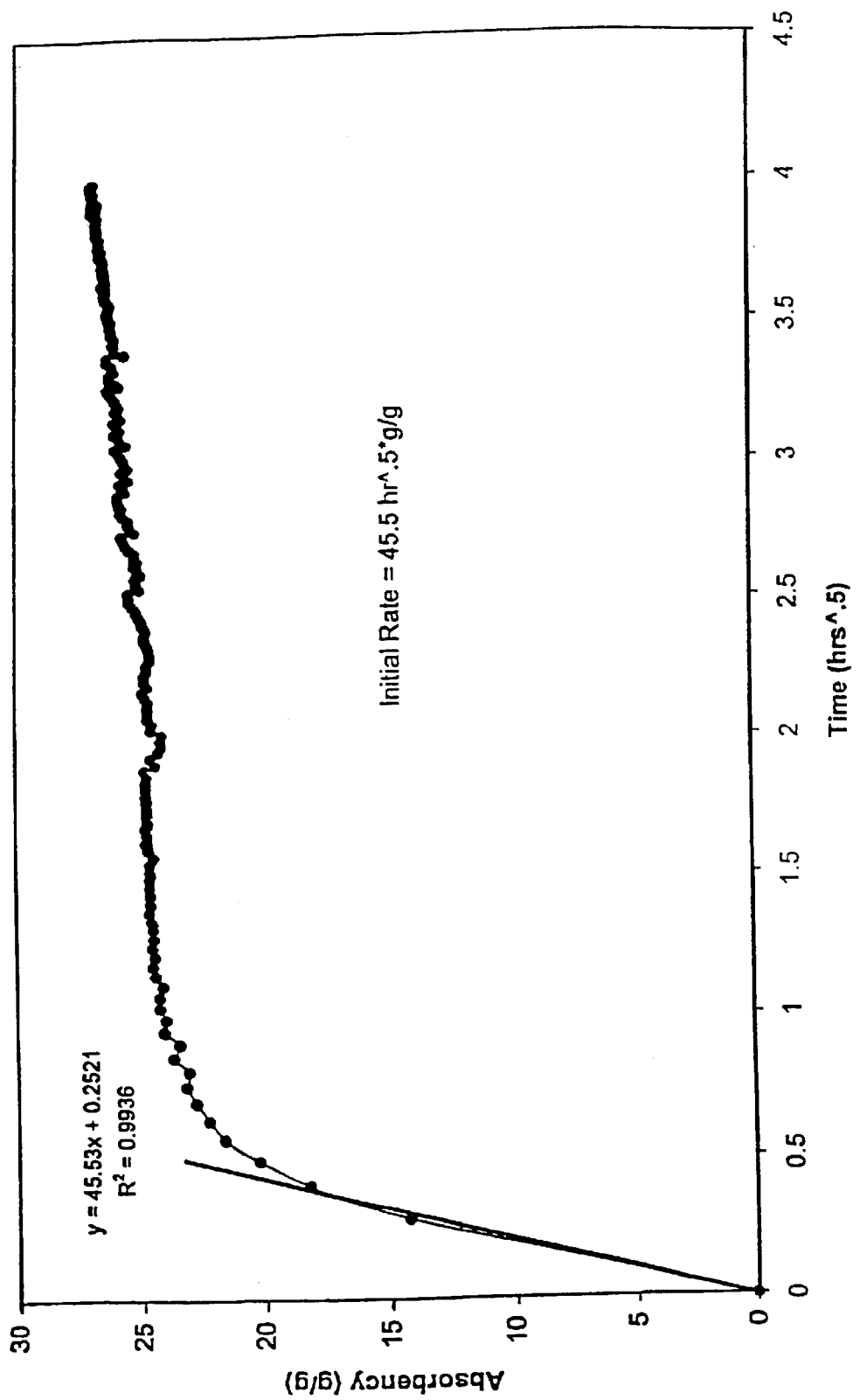
FIG. 19 is a plot of initial PUP capacity vs. $t^{1/2}$ for a superabsorbent material containing 25% multicomponent SAP particles and 75% poly(AA)(DN=70), by weight.

FIGS. 18 and 19 show that the present superabsorbent materials exhibit excellent permeability and absorption kinetics, in addition to excellent liquid absorption and retention. The plots in FIGS. 18 and 19 illustrate performance properties for a superabsorbent material containing, by weight, 75% poly(AA)(DN=70) particles and 25% multicomponent SAP particles (55/45, by weight, poly(vinylamine/poly(AA) (DN=0). This superabsorbent material had an SFC of $34.4 \times 10^{-7}$ cm$^3$sec/g. FIG. 18 contains a plot of PUP at 0.7 psi over time. FIG. 18 demonstrates that a present superabsorbent material essentially attains its maximum absorption capacity after one hour (24.02 g/g). After 3 hours, the absorptive capacity was 24.74 g/g. After 16 hours, the absorptive capacity was 26.90 g/g.

The data presented above illustrates that a the multicomponent SAP particles have an SFC of greater than $15 \times 10^{-7}$ cm$^3$ sec/g, and typically greater than $20 \times 10^{-7}$ cm$^3$ sec/g. Preferred embodiments have an SFC about $30 \times 10^{-7}$ cm$^3$ sec/g or greater, for example, up to about $800 \times 10^{-7}$ cm$^3$ sec/g. In particular, an SAP material containing 25% multicomponent SAP particle and 75% poly(AA)(DN=70) particles has an SFC of 34.4 cm$^3$ sec/g. An SAP material

TABLE 12

| Time (min) | Sample 1 (control)[26] | Sample 2 (comparative)[27] | Sample 3 (comparative)[34] | Sample 4 (comparative)[28] | Sample 5[35] | Sample 6[36] | Sample 7[37] | Sample 8[38] |
|---|---|---|---|---|---|---|---|---|
| 0 | 0 | 0 | 0 | 0 | 0 | 0 | 0 | 0 |
| 5 | 25.3 | 14.8 | 16.4 | 26 | 21.7 | 28.3 | 27.5 | 24.4 |
| 10 | 30.7 | 20.9 | 23.5 | 33.2 | 26.8 | 34.7 | 33.6 | 30.2 |
| 15 | 32.1 | 25.1 | 26.8 | 37.9 | 30.4 | 37.8 | 36.2 | 32.8 |
| 30 | 33.8 | 31.2 | 31.2 | 43.3 | 36.9 | 42.5 | 39.8 | 36.5 |
| 45 | 34.2 | 34.3 | 33.4 | 45.8 | 39.5 | 44.6 | 41.9 | 38.1 |
| 60 | 34.5 | 36.4 | 34.8 | 47.6 | 42.7 | 45.9 | 43.3 | 38.9 |
| 120 | 35.2 | 40.0 | 36.1 | 49.1 | 48.7 | 48.2 | 46.7 | 40.1 |
| 180 | 35.2 | 42.3 | 37.3 | 49.7 | 50.1 | 50.4 | 48.4 | 46.4 |
| SFC | 15 | 115 | 59 | 368 | 194 | 207 | 244 | 179 |

[34] Comparative sample containing a dry blend of 25% poly(AA) (DN = 70), 41.5% poly(vinylamine), and 33.5% poly(AA) (DN = 0);
[35] SAP material containing 10% poly(vinylamine) and 90% multicomponent SAP containing 55% poly(vinylamine) and 45% poly(AA), prepared in accordance with Example 12;
[36] SAP material containing 10% poly(AA) (DN = 0) and 90% multicomponent SAP containing 55% poly(vinylamine) and 45% poly(AA), prepared in accordance with Example 12;
[37] SAP material containing 11% poly(vinylamine), 9% poly(AA) (DN = 0), and 80% multicomponent SAP containing 55% poly(vinylamine) and 45% poly(AA), prepared in accordance with Example 12;
[38] Blend of 25% poly(AA) (DN = 70) and 75% multicomponent SAP containing 55% poly(vinylamine) and 48% poly(AA), prepared in accordance with Example 12.

Figure 12:
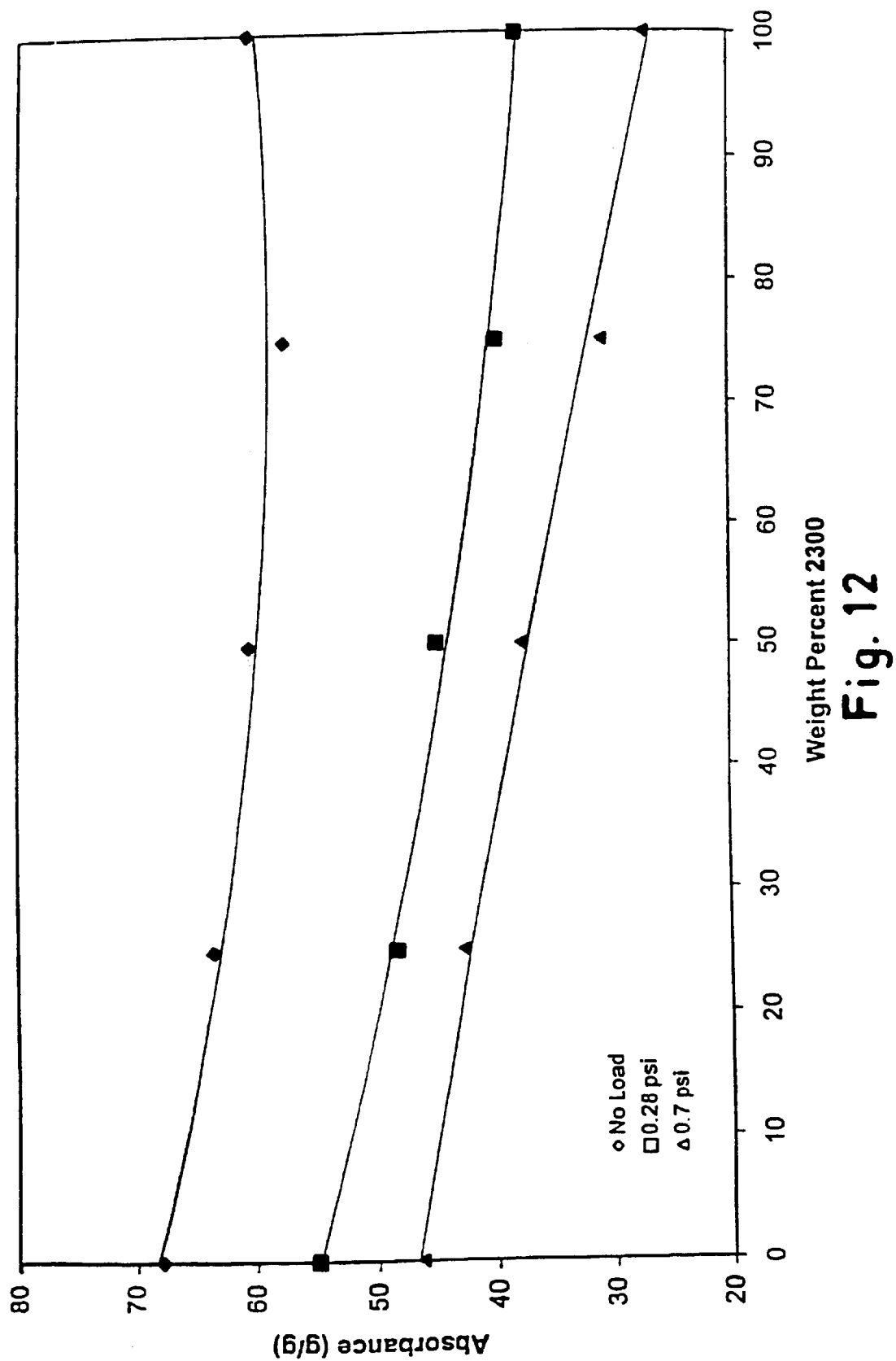
FIG. 12 contains plots of absorbance (in g/g) vs. weight percent of poly(AA) (DN=70) in a blend of multicomponent SAP particles and particles of poly(AA) (DN=70)
Figure 13:
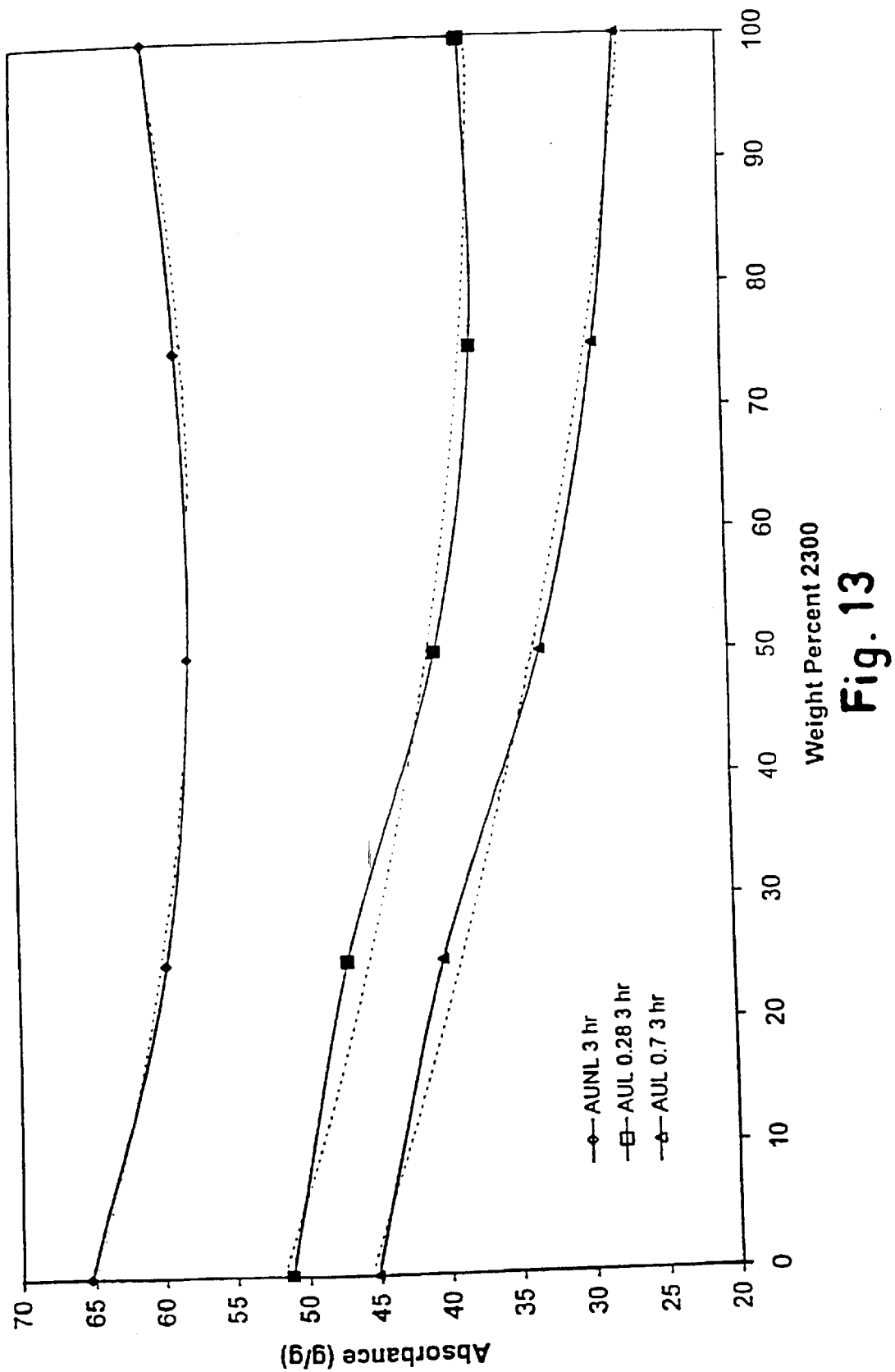
FIG. 13 contains plots of absorbance (in g/g) vs. weight percent of poly(AA) (DN=70) in a blend of particles of poly(AA) (DN=70), particles of poly(AA) (DN=0), and particles of poly(vinylamine)

To further illustrate the improved absorption properties of an SAP material comprising a blend of (a) multicomponent SAP particles and (b) particles of a second water-absorbing resin, FIG. 12 contains plots of absorbance (g/g), both under load and not under load, for various combinations of poly(AA) (DN=70) and a multicomponent SAP containing 55% poly(vinylamine) dispersed in 45% poly(AA) (DN=0). The combinations tested in FIG. 12, which contain multicomponent SAP particles, outperformed the combinations tested in FIG. 13, which contain a blend of poly(AA) (DN=70), poly(AA) (DN=0), and poly(vinylamine) particles.

containing 75% multicomponent SAP particles and 25% poly(AA)(DN=70) has an SFC of 189 cm$^3$ sec/g.

FIG. 19 illustrates the initial PUP capacity rate for absorbency vs. (time)$^{1/2}$ over 4 hours for a multicomponent SAP material. The plot in FIG. 19 demonstrates an improved initial PUP capacity rate of 45.5 g/g/hr$^{1/2}$ for the multicomponent superabsorbent material. A standard poly(AA)(DN=70) has an initial PUP capacity rate of 40.7 g/g/hr$^{1/2}$.

To further illustrate that the multicomponent SAP particles, and superabsorbent materials containing multicomponent SAP particles, (a) have an improved ability to absorb liquids faster, (b) have a better liquid diffusion rate, and (c) have an improved ability to absorb and retain liquids, laboratory diaper cores containing the multicomponent SAP particles were prepared and compared to laboratory diaper cores containing a conventional SAP and to commercially available diapers. In particular, the following diaper cores were prepared:

| | |
|---|---|
| Core A | 100% poly(AA) (DN = 70) |
| Core B | 100% multicomponent SAP particles containing 55% poly(vinylamine) and 45% poly(AA) (DN = 0), by weight. |
| Core C | 16.5% multicomponent SAP (as in Core B), 33.5% poly(AA) (DN = 70), and 50% fluff pulp, by weight, |
| Core D | 23.3% multicomponent SAP (as in Core B), 46.7% poly(AA) (DN = 70), and 30% fluff pulp, by weight, |
| Core E | 33.5% multicomponent SAP (as in Core B), 16.5% poly(AA) (DN = 70), and 50% fluff pulp, by weight, |
| Core F | 46.7% multicomponent SAP (as in Core B), 23.5% poly(AA) (DN = 70), and 30% fluff pulp, by weight, |
| Core G1 | 27.5% poly(vinylamine), 22.5% poly(AA)- (DN = 0), and 50% fluff pulp, by weight, |
| Core G2 | identical to Core G1 except the multicomponent SAP was surface crosslinked with 500 ppm EGDGE, |
| Core H1 | 38.5% poly(vinylamine), 31.5% poly(AA)- (DN = 0), and 30% fluff pulp, by weight, |
| Core H2 | identical to Core G1 except the multicomponent SAP was surface crosslinked with 500 ppm EGDGE. |

Cores A and B are referred to as "pulpless" cores, i.e., the cores contain 100% of an SAP. Typically, commercial diapers contain 45% to 60% by weight of a pulp to achieve rapid absorption of a liquid. Diaper Cores A through H2 were compared to one another, and to other laboratory cores and commercial diapers, to illustrate the improved permeability and absorption kinetics, and improved liquid absorption and retention, provided by a diaper having a core that contains multicomponent SAP particles of the present invention, either as the sole SAP, or as a component in a superabsorbent material.

Present day diapers generally consist of a topsheet made from a nonwoven material that is in contact with the skin of the wearer, an acquisition layer below (i.e., opposite the skin of wearer) the topsheet, a core that is below the acquisition layer, and a backsheet below the core. This construction is well known in the industry. In a preferred embodiment, the present diaper consists essentially of a topsheet, a core, and a backsheet, i.e., an acquisition layer is not present. As illustrated below, the improvements provided by present multicomponent SAP particles, or superabsorbent material, permit an acquisition layer to be omitted from a disposable diaper. Such a result is both new and unexpected in the art in that an expensive acquisition layer can be omitted, the diaper is lighter and thinner, and absorptive properties are not adversely affected.

Cores A through H2, and the other laboratory cores referred to herein, were prepared using a conventional laboratory procedure as follows:

A laboratory core-forming unit comprising a two-chamber vacuum system forms an airlaid fluff pulp absorbent composite matrix to produce a 12 cm×21 cm diaper core. The core-forming unit comprises a roller brush on a variable-speed laboratory motor, a fiber distribution screen in close proximity to the brush, a forming screen on an adjustable damper, and a vacuum system capable of supplying a consistent and continuous negative pressure between 8 and 15 inches of water.

The core-forming unit is contained such that the vacuum pulls the fibers and granular material from an adjustable introduction slide, through the rotating brush and distribution screen, directly onto the forming screen. The vacuum exhaust is recirculated through the inlet of the formation slide, thereby controlling the temperature and humidity of the operation.

When forming a core, the desired amount of defiberized fluff pulp is evenly disbursed in small pieces onto the brush roller in the upper chamber. In the lower chamber, a rectangular tissue, or topsheet (21 cm×12 cm), is placed onto the forming screen. For most cores, the sliding upper chamber lid is partially closed to leave about a one-half inch gap. In the case of a homogeneous pulp/SAP core, the SAP is sprinkled through the gap into the upper chamber immediately after the brush begins rotating. In order to achieve a homogeneous distribution, a small amount of SAP is added to the fluff prior to beginning the motor. The amount of time used to introduce the remainder of the SAP varies with the amount of fluff pulp utilized. After the fiber and absorbent polymer material are deposited, the motor is turned off, and the damper unit containing the laboratory core is removed from the lower chamber. The uncompressed core then is placed on a backsheet made from a polymeric film, and put into a compression unit. At this time, another rectangular tissue and a nonwoven coverstock is placed on top of the core. Absorbent cores are compressed for a given amount of time, typically 5 minutes, with a hydraulic press at pressures of between about 5,000 psi and about 10,000 psi, and typically about 7,000 psi, to achieve the desired density. After the 5 minutes, the laboratory-prepared absorbent cores are removed from the press, weighed, and measured for thickness.

Cores A through H2, and other laboratory cores and commercial diapers, were tested for rewet under a 0.7 psi load, liquid acquisition time, and liquid acquisition rate. The following describes the procedure to determine the acquisition and rewet under load of a hygienic article, like a diaper. These tests exhibit the rate of absorption and fluid retention of a 0.9%, by weight, saline solution, by a hygienic article over 3 to 5 separate fluid insults while under a load of 0.7 psi.

Apparatus 100 ml separatory funnel, configured to deliver a flow rate of 7 ml/sec., or equivalent;
3.642 kg circular weight (0.7 psi) 10 cm diameter, with 2.38 cm ID perspex dose tube through the center of weight;
VWR Scientific, 9 cm filter paper or equivalent;
2.5 kg circular weight (0.7 psi)—8 cm diameter;
Digital timer;
Electronic balance (accuracy of a 0.01 gram); Stopwatch.

Procedure

1. Preparation
(a) Record the weight (g) of the hygienic article, e.g., diaper, to be tested;
(b) Place hygienic article flat on the bench top, for example, by removing any elastics and/or taping the ends of the article to the bench top;
(c) Place the 3.64 kg circular weight onto the hygienic article with the opening of the perspex dose tube positioned at the insult point (i.e., 5 cm toward the front from the center).

2. Primary Insult and Rewet Test
(a) Measure 100 ml of 0.9% NaCl solution (i.e., 0.9% by weight sodium chloride in deionized or distilled water) into separatory funnel. Dispense the NaCl solution into the perspex tube of the weight at a flow rate of 7 ml/sec and start the timer immediately. Stop the timer when all of the NaCl solution has completely disappeared from the surface of the hygienic article at the base of the perspex tube. Record this time as the primary acquisition time (sec).
(b) After 10 minutes have elapsed, remove the weight and conduct the rewet test procedure:
  (i) Weigh a stack of 10 filter papers, record this value (dry weight).
  (ii) Place the filter papers over the insult point on the hygienic article. Set the timer for 2 minutes. Place the 2.5 kg weight onto the filter papers and start timer immediately.
  (iii) After 2 minutes have elapsed, remove the weight and reweigh the filter papers (wet weight). Subtract the dry weight of the filter papers from the wet weight, this is the rewet value. Record this value as the primary rewet value (g).
3. Secondary Insult and Rewet Test
(a) Place the 3.64 kg weight back onto the hygienic article in the same position as before. Repeat step 2a using 50 ml NaCl solution (recoding the absorption time as the secondary acquisition time) and steps 2b (i)–(iii) using 20 filter paper (recording the rewet values as the secondary rewet).
4. Tertiary, and additional, Insult and Rewet Tests
(a) Place the load back onto the diaper in the same position as before. Repeat step 2a using 50 ml of NaCl solution (recording the absorption time as the tertiary acquisition time) and steps 2b (i)–(iii) using 30 filter paper (recording the rewet value as the tertiary or subsequent rewet).

The following FIGS. 20–29 illustrate improved diapers that contain multicomponent SAP particles, or that contain other superabsorbent materials.

Figure 20:
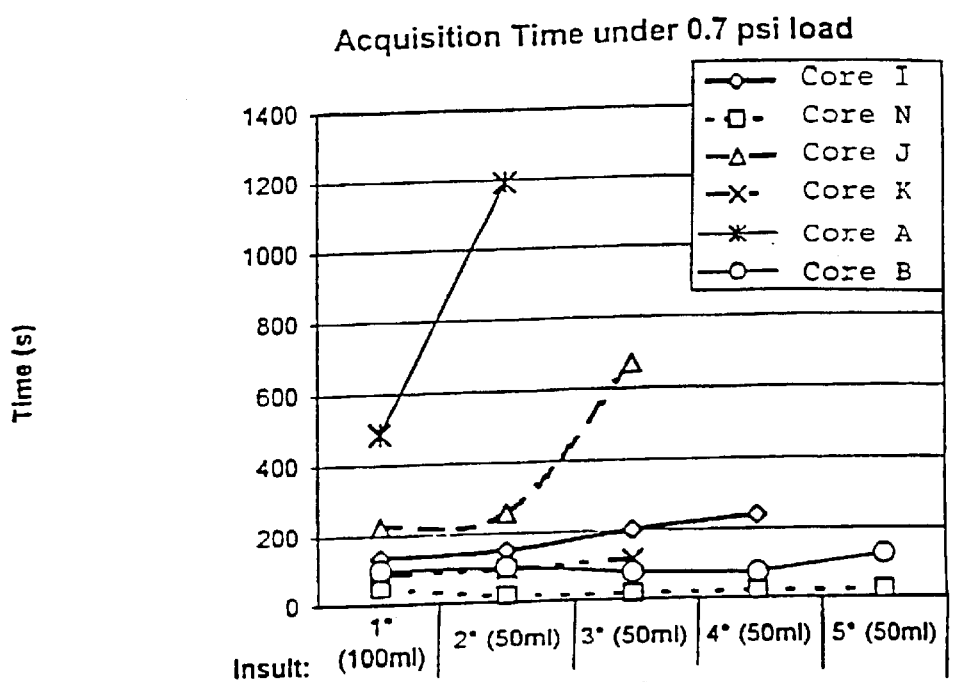
FIGS. 20, 21, 23–26, and 28 are plots of acquisition time (seconds) vs. number of insults for a series of laboratory prepared diaper cores under a load of 0.7 psi.

FIG. 20 contains plots of acquisition time vs. number of insults with 0.9% aqueous saline, under a 0.7 psi load, for diapers containing Cores A and B, a core containing 50% of a multicomponent SAP and 50% fluff (Core N), a comparative core containing 50% poly(AA)(DN=70) and 50% fluff (Core I), a core identical to Core I, but absent an SAP (Core J), and a core identical to Core J but containing twice the amount of fluff as Core J (Core K). In FIG. 20, Cores B and N contain multicomponent (combined acidic and basic resins) particles. Cores A, I, J, and K are comparative cores.

Cores B and N exhibited an excellent ability to acquire 0.9% saline under a 0.7 psi load. Cores J and K acquired the saline slowly, especially during rewetting. Core I represents a standard core containing 50% SAP, and has a higher acquisition time than Cores B or N. The acquisition time for Core A could not be measured beyond the third insult because acquisition was very slow.

Figure 21:
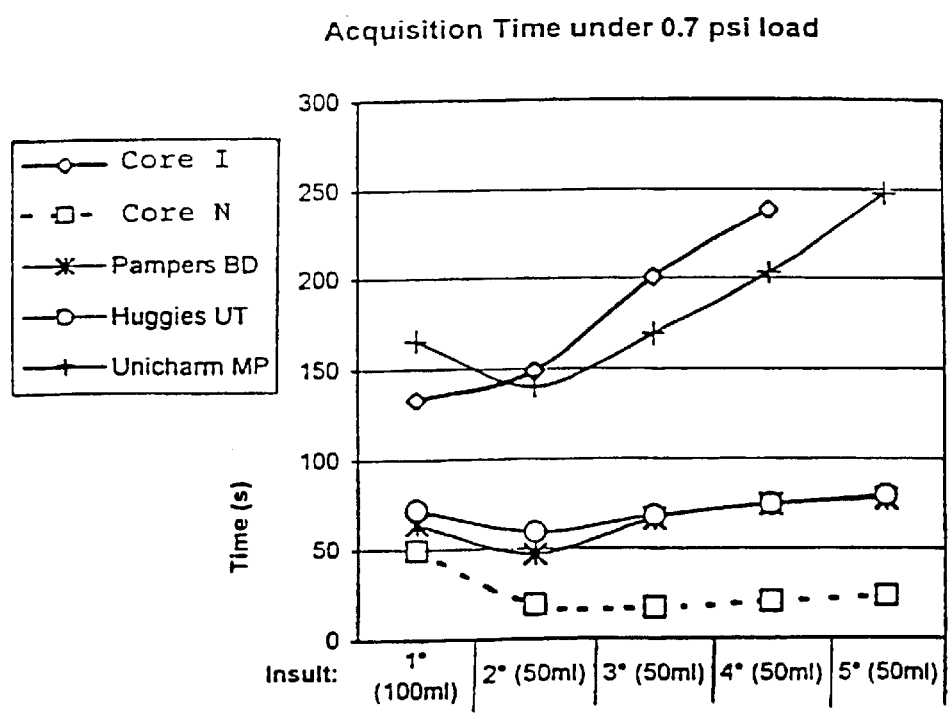
Figure 22:
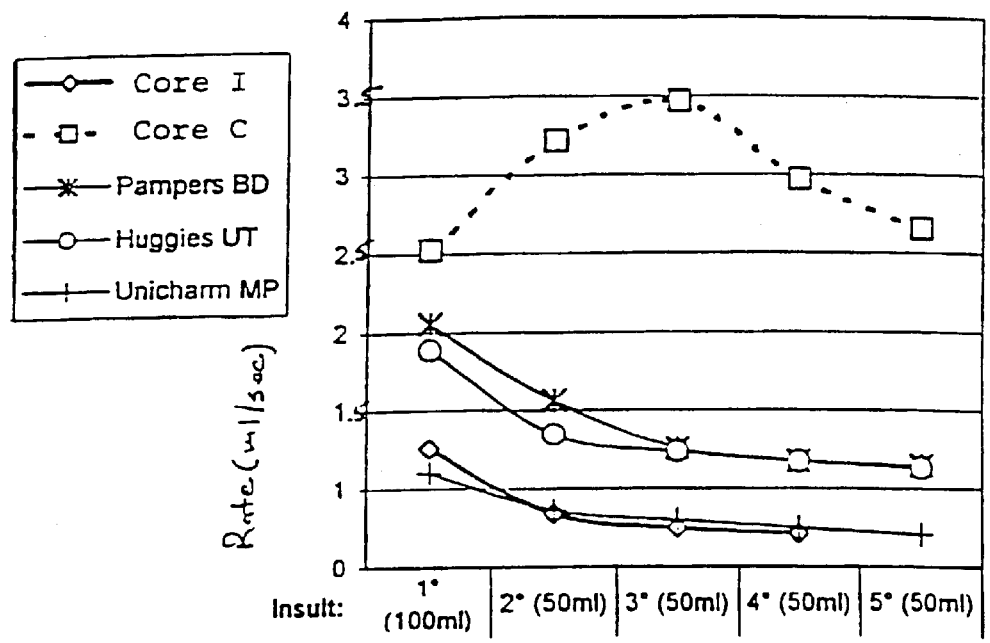
FIGS. 22, 27, and 29 are plots of acquisition rate vs. number of insults for a series of laboratory prepared diaper cores under a load of 0.7 psi.

FIG. 21 illustrates the acquisition time under a 0.7 psi load for Cores I and N and for various commercial diapers. FIG. 21 shows that Core N significantly outperforms both comparative laboratory cores (Core I) and commercial diapers with respect to acquisition time of 0.9% saline under a 0.7 psi load. FIG. 22 illustrates that a core of the present invention, i.e., Core C, has a greater acquisition rate at 0.7 psi than commercial diapers and comparative laboratory cores containing poly-(AA)(DN=70) (i.e., acquisition rate is greater than 2 ml/sec for an initial 100 milliliter insult and four subsequent 50 milliliter insults with 0.9% saline).

Figure 23:
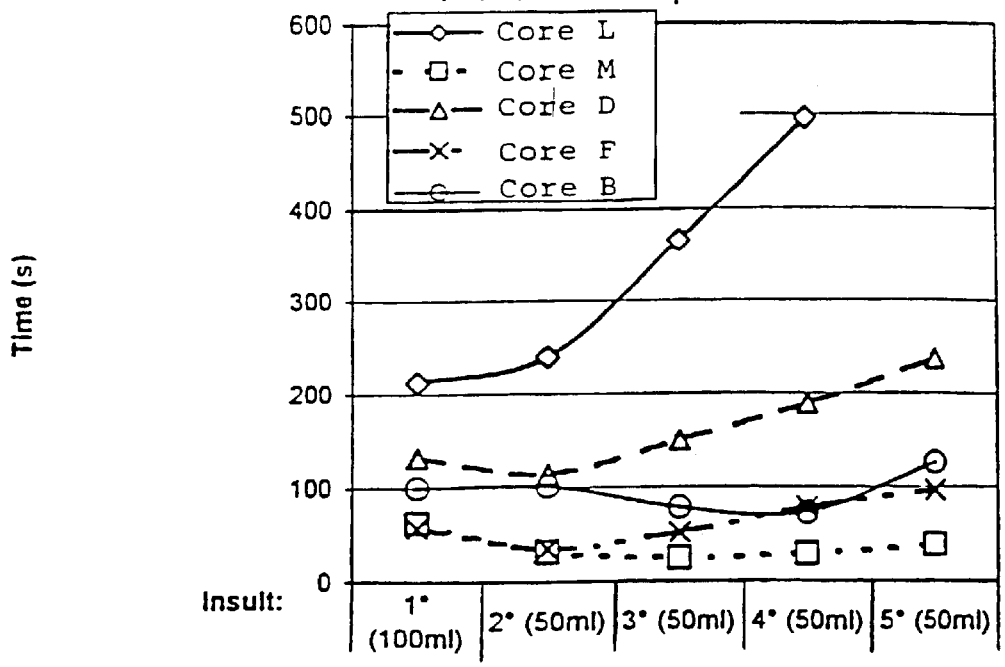

FIG. 23 contains acquisition times for Cores B, D, and F, for a comparative core containing 70% poly(AA)(DN=70) and 30% fluff (Core L), and for a core containing 70% multicomponent SAP particles and 30% fluff (Core M). Cores B, D, F, and M of the present invention significantly outperformed Core L with respect to acquisition time. Core L could not be tested for the fifth insult because the acquisition time was too great.

Figure 24:
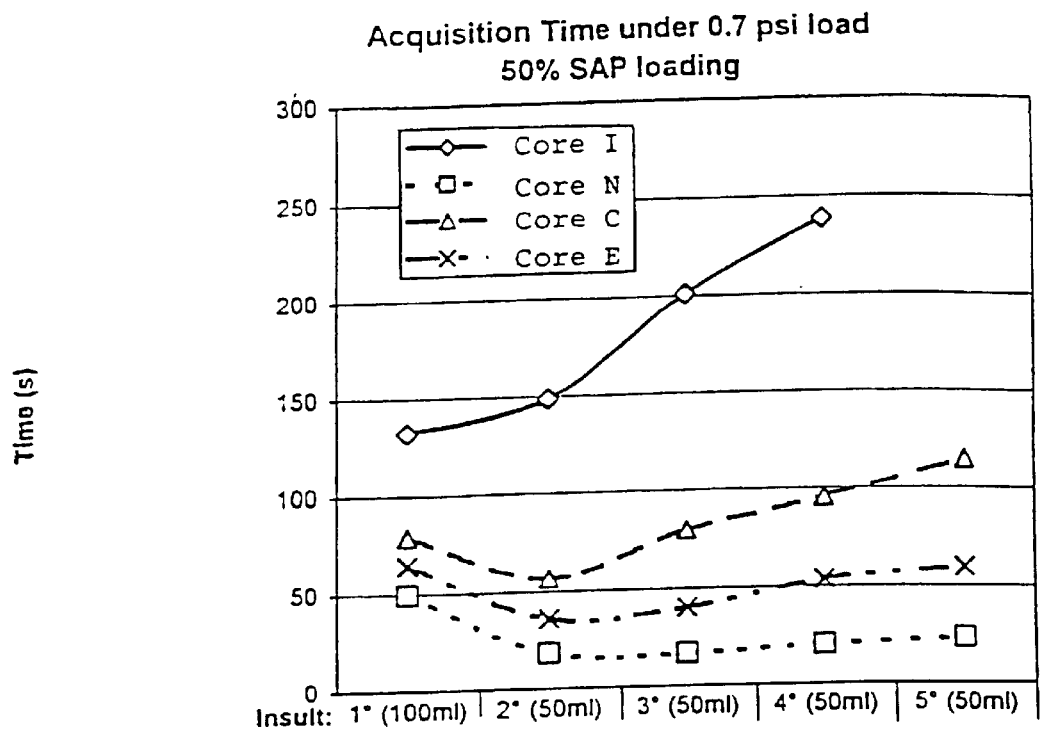
Figure 25:
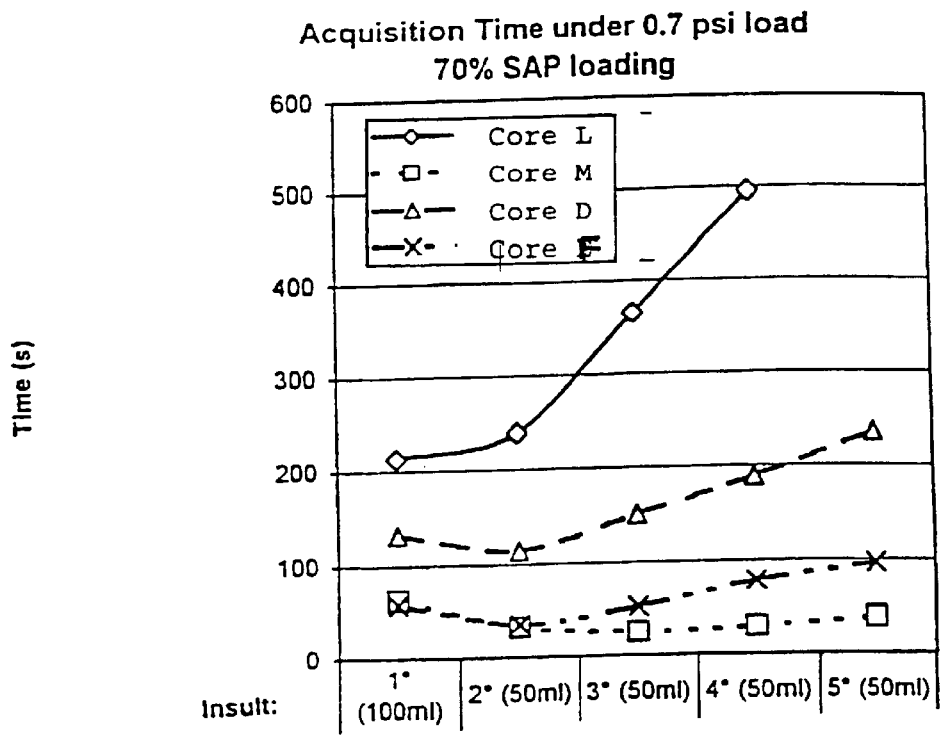
Figure 26:
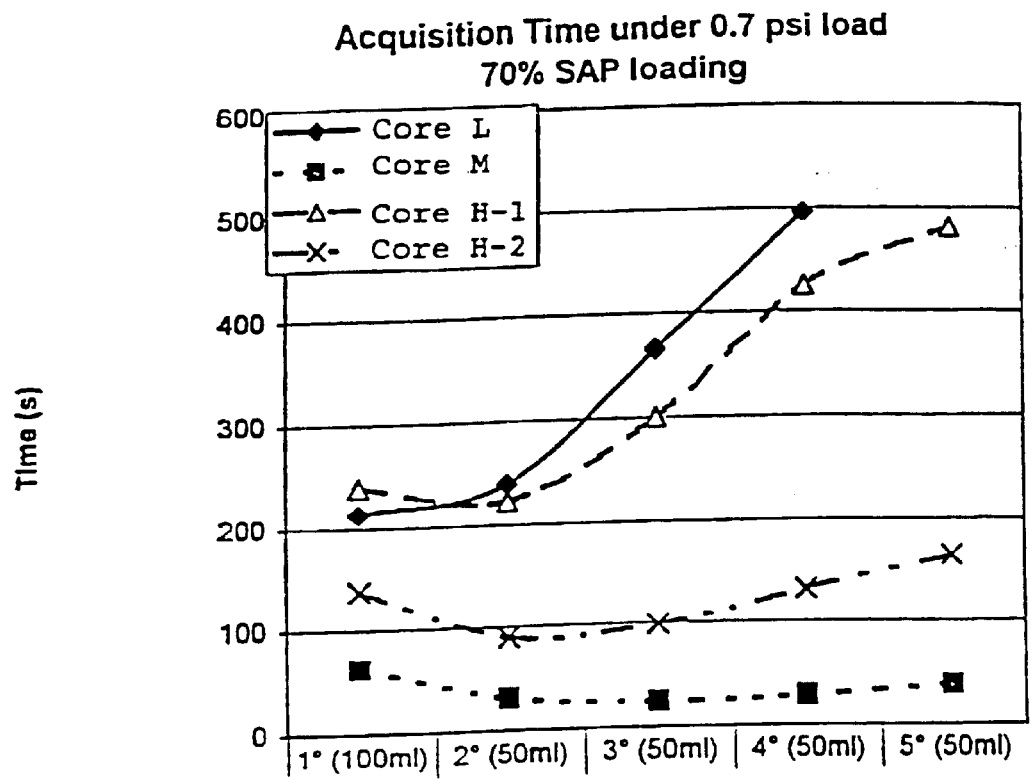
Figure 27:
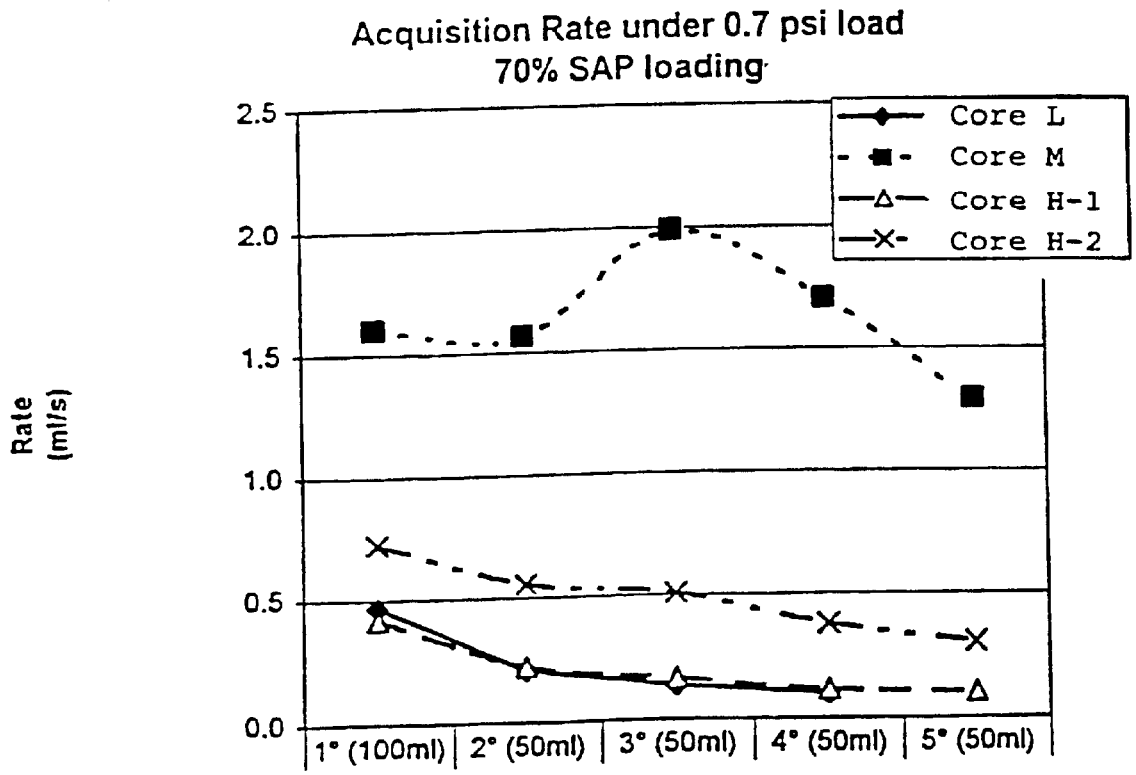
Figure 28:
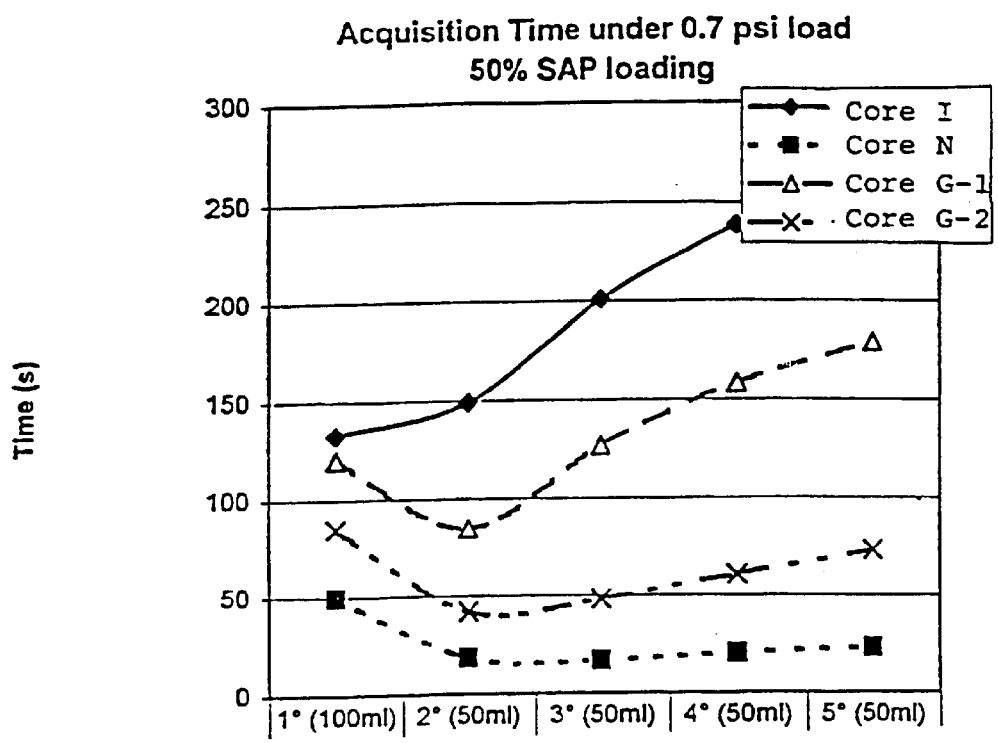
Figure 29:
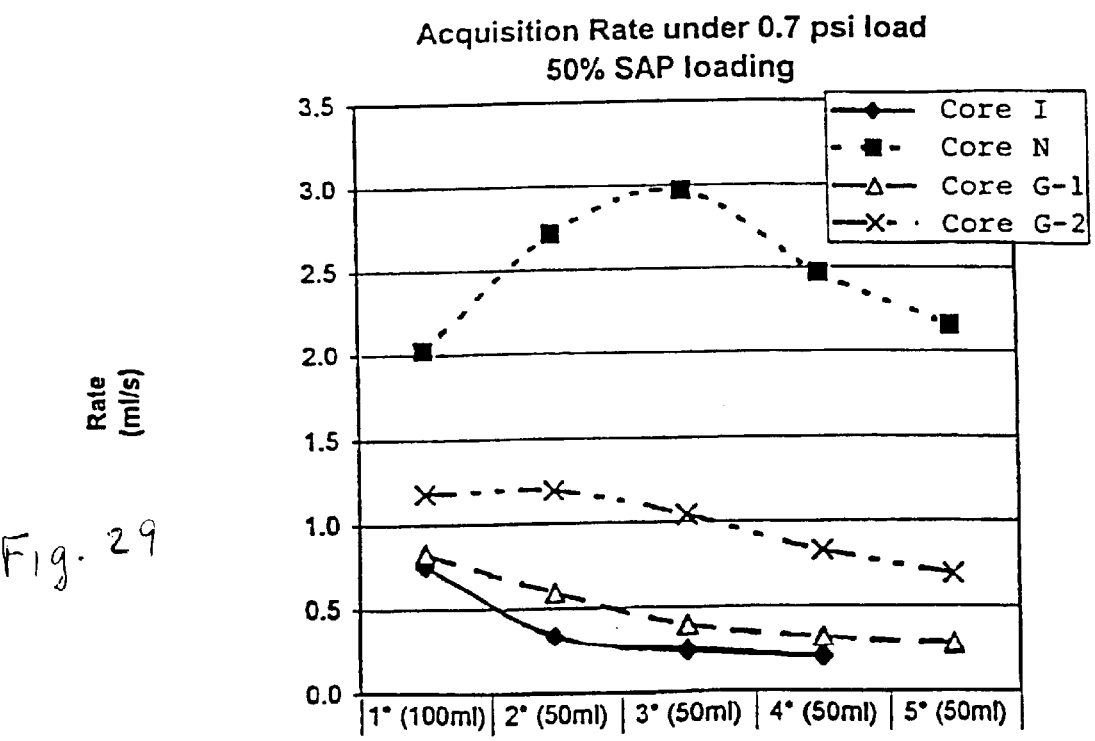

FIG. 24 similarly compared Cores C, E, I, and N. All cores contained 50% SAP, and Cores C, E, and N, containing multicomponent particles, significantly outperformed comparative Core I. FIG. 25 contains similar plots for cores containing 70% SAP. Cores D, F, and M significantly outperformed comparative Core L with respect to acquisition time.

FIGS. 26–29 contain plots of acquisition time and acquisition rate, and show that at both a 70% SAP loading of the core (FIGS. 26 and 27) and at a 50% SAP loading of the core (FIGS. 28 and 29), the cores containing multicomponent particles, i.e., cores G1, G2, H1, H2, M, and N, significantly out-performed comparative cores I and L.

Overall, the data presented in FIGS. 20–29 demonstrate that a diaper core of the present invention, containing multicomponent SAP particles, maintains a flat, essentially constant, or surprisingly a decreased, acquisition time over five insults, whereas prior cores demonstrate an increased acquisition time as the number of insults increase. The data also shows an unexpected faster acquisition rate as the number of insults increases, i.e., an acquisition rate for a subsequent insult is greater than for a previous insult. Such results are unexpected because prior cores exhibit a decrease in acquisition rate as the number of insults increase. The sheet material cores, therefore, have second acquisition rates that are at most 20% slower than a first acquisition rate, and typically are 1%–20% slower, are equal to, or are greater than the first acquisition rate. The practical result of these improved properties is a core having a greatly improved ability to prevent leakage in gush situations and in rewet situations, even in the absence of acquisition layers.

The data also shows that significant improvements in liquid absorption, both with respect to kinetics and retention, are observed if the standard poly(AA)(DN=70) presently used in cores is completely replaced by multicomponent SAP particles, or is replaced by a blend of superabsorbent resins, i.e., a composition containing multicomponent SAP particles and a second water-absorbing resin, such as poly (AA)(DN=70).

To further illustrate that the bicomponent SAP materials (particles of an acidic water-absorbing resin blended with particles of a basic water-absorbing resin) have an improved ability to absorb and retain liquids similar to the cores containing the multicomponent SAP particles, laboratory diaper cores containing the bicomponent SAP material were prepared and tested in the same manner as the cores containing multicomponent SAP particles, and compared to laboratory diaper cores containing a conventional SAP. In particular, the following diaper cores were prepared:

| | |
|---|---|
| Core A1 | 50% poly(AA) (DN = 70) and 30% fluff |
| Core A2 | 70% poly(AA) (DN = 70) and 50% fluff |
| Core B1 | 27.5% poly(vinylamine), 22.5% poly(AA)-(DN = 0), and 50% fluff pulp, by weight, |
| Core C1 | identical to Core B except the poly(vinyl-amine) was surface crosslinked with 500 ppm EGDGE, |

| | -continued |
|---|---|
| Core D1 | 38.5% poly(vinylamine), 31.5% poly(AA)-(DN = 0), and 50% fluff pulp, by weight, |
| Core E1 | identical to Core B except the poly(vinyl-amine) was surface crosslinked with 500 ppm EGDGE, |

FIGS. 30–33 illustrate the improved properties of diapers that contain bicomponent SAP materials.

Figure 30:
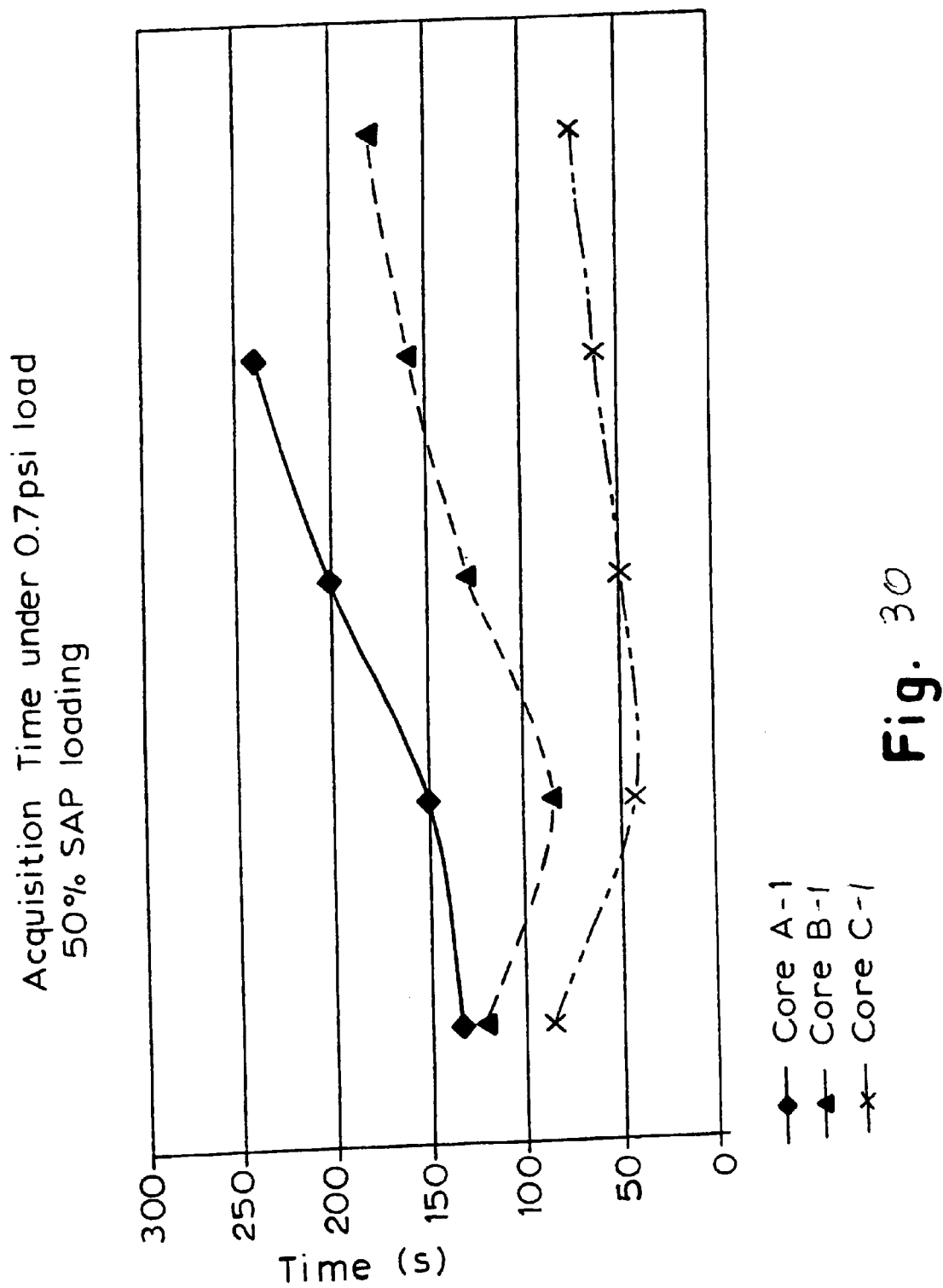
FIGS. 30 and 31 are plots of acquisition time (seconds) vs. number of insults for a series of laboratory prepared diaper cores under a load of 0.7 psi.

FIG. 30 contains plots of acquisition time vs. number of insults with 0.9% aqueous saline, under a 0.7 psi load, for diapers containing Cores A1, B1, and C1. In FIG. 30, Cores B1 and C1 are cores containing the bicomponent blend of acidic and basic resins. Core A1 is a comparative core.

Cores B1 and C1 exhibited an excellent ability to acquire 0.9% saline under a 0.7 psi load. Core A1 acquired the saline relatively slowly, especially during rewetting. Core A1 represents a standard core containing 50% SAP, and has a higher acquisition time than Cores B1 or C1. The acquisition time for Core A1 could not be measured beyond the fourth insult because acquisition was very slow.

Figure 31:
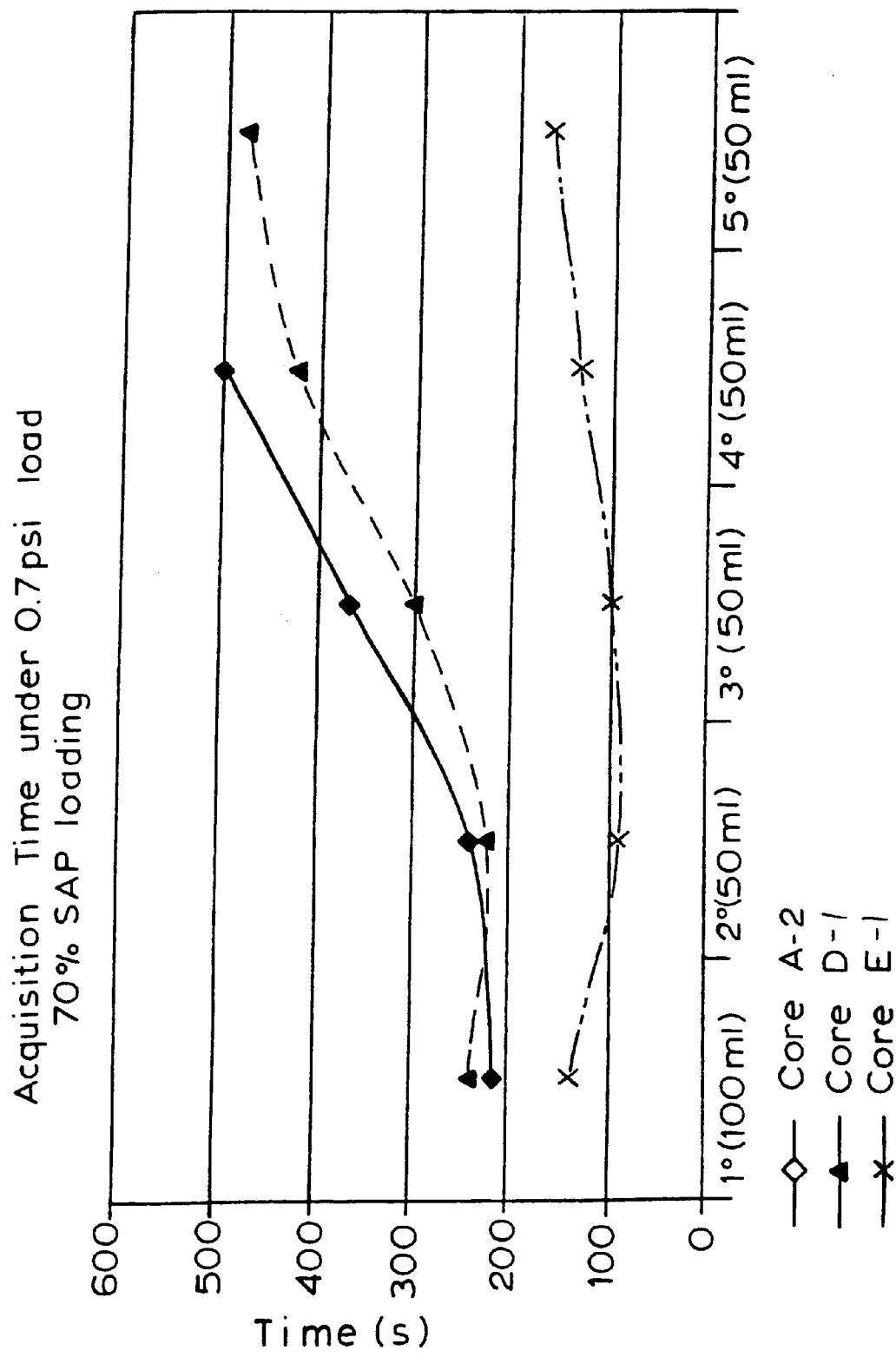

FIG. 31 illustrates the acquisition time for Cores A2, D1, and E1. FIG. 31 shows that Cores D1 and E1 significantly outperform a comparative laboratory core (Core A2) with respect to acquisition time of 0.9% saline under a 0.7 psi load.

Figure 32:
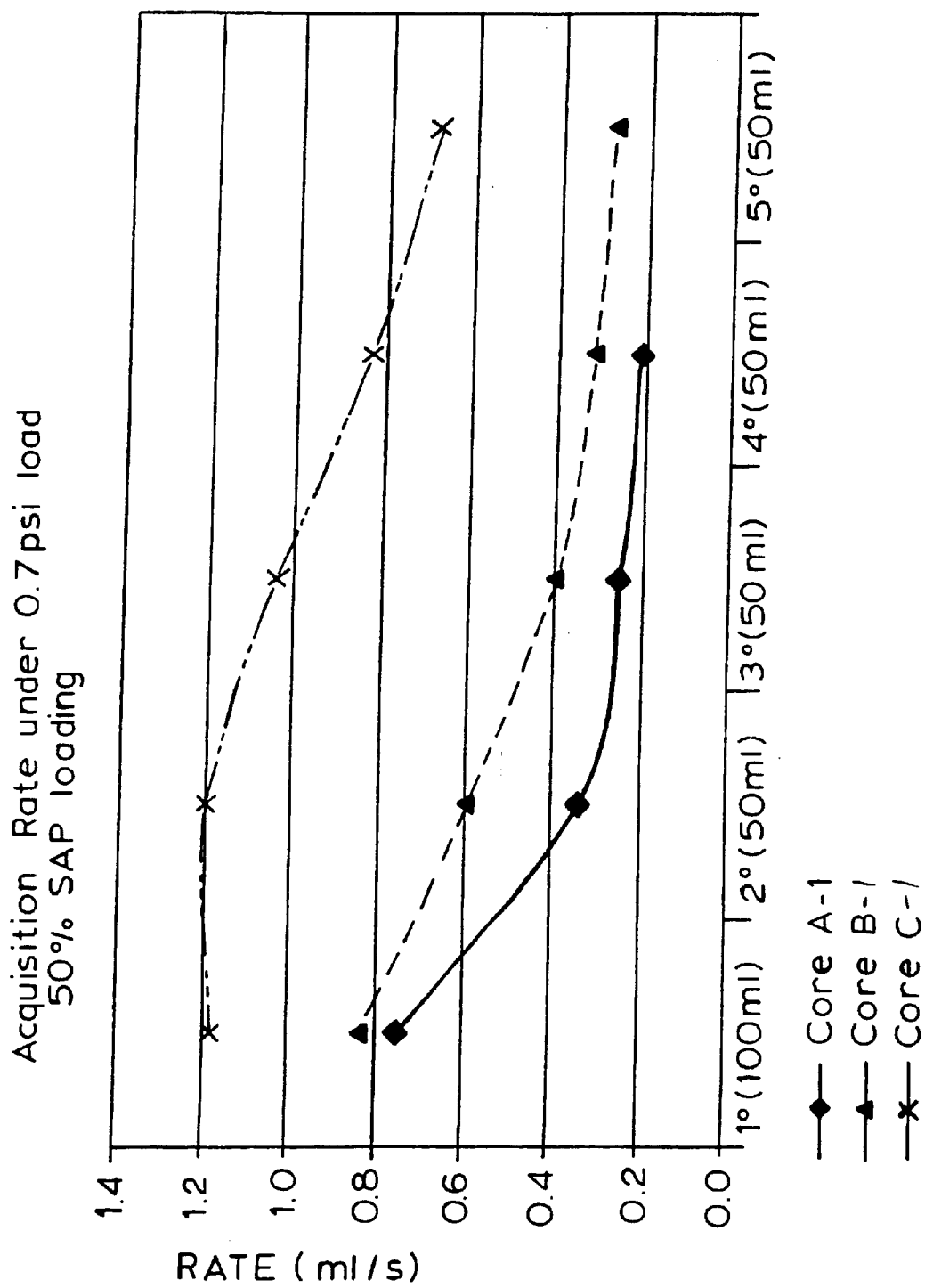
FIGS. 32 and 33 are plots of acquisition rate (ml/sec) vs. number of insults for a series of laboratory prepared diaper cores under a load of 0.7 psi.
Figure 33:
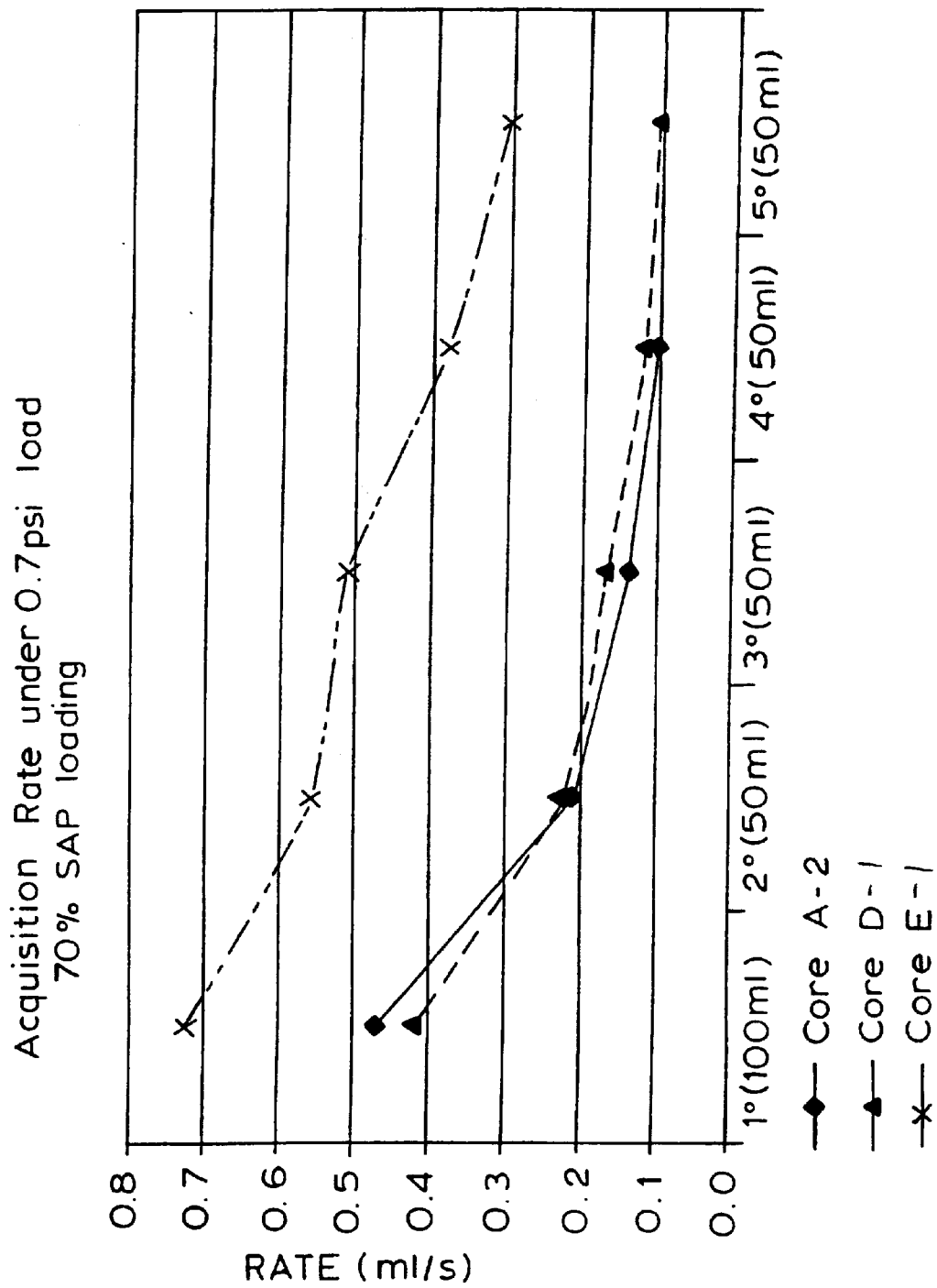

FIGS. 32 and 33 illustrate that a core containing the bicomponent blend of acidic and basic resins, i.e., Cores B1–E1, have a greater acquisition rate than comparative laboratory cores containing poly(AA)(DN=70).

Overall, the data presented in FIGS. 30–33 demonstrate that a sheet material diaper core of the present invention maintains a flat, essentially constant, or surprisingly a decreased, acquisition time over five insults, whereas prior art diaper cores demonstrate an increased acquisition time over prior cores. The data also shows an improved acquisition rate as the number of insults increases. Such results are unexpected because prior cores exhibit a decrease in acquisition rate as the number of insults increase, especially between the first and second insult. The sheet materials of the present invention maintain the initial acquisition rate after a second insult with saline (see FIG. 32). The present cores, therefore, can have a second acquisition rate that is at most 20% slower than a first acquisition rate, and preferably is at least equal to the first acquisition rate. The practical result of these improved properties is a core having an improved ability to prevent leakage in gush situations and in rewet situations.

The data shows that improvements in liquid absorption, both with respect to kinetics and retention, are observed if the standard poly(AA)(DN=70) presently used in cores is completely replaced by the bicomponent SAP material.

The improved results demonstrated by a core of the present invention also permit the thickness of the core to be reduced. Typically, cores contain 50% or more fluff or pulp to achieve rapid liquid absorption while avoiding problems like gel blocking. The present cores, which contain a bicomponent SAP material, acquire liquids sufficiently fast to reduce problems, like gel blocking, and, therefore, the amount of fluff or pulp in the core can be reduced. A reduction in the amount of the low-density fluff results in a thinner core, and, accordingly, a thinner diaper.

Therefore, a core of the present invention can contain at least 50% of an SAP, preferably at least 75% of an SAP, and up to 100% of an SAP. In various embodiments, the presence of a fluff or pulp is no longer necessary, or desired, while retaining structural integrity in the sheet material manufactured, even without an adhesive resin and little or no fiber. In each case, the SAP in a present core contains multicomponent SAP particles, or its separate components, in an amount of about 15% to 100% of the weight of the sheet material article. Additional SAP articles can be a second water-absorbing resin, either basic or acidic. The second water-absorbing resin preferably is not neutralized, but can have a degree of neutralization up to 100%. The multicomponent SAP particles can be admixed with particles of a second water-absorbing resin for introduction into a diaper core. Alternatively, the diaper core can contain zones of multicomponent SAP particles and zones of a second water-absorbing resin.

In addition to a thinner sheet material layer, e.g., diaper core, sheet material cores, manufactured in accordance with the present invention, also allow an acquisition layer to be omitted from the diaper. The acquisition layer in a diaper typically is a nonwoven or fibrous material, typically having a high degree of void space or "loft," that assists in the initial absorption of a liquid. The present cores acquire liquid at a sufficient rate such that diapers free of an acquisition layers are practicable.

Sheet Material Testing

Airlaid sheet materials were made on a commercial pilot line. General considerations on making airlaid product in this line with SAP is that it is difficult to make the product (especially at low basis weight, e.g., $\leq 200$ gsm (grams per $m^2$) which contain in excess of 50% SAP, unless there is an increase in bicomponent fiber (from 5% to 10% by weight or more, based on the dry weight of the sheet material). Even with increasing bicomponent fiber, the upper limit is about 60% SAP as the mat does not have enough integrity to be handled and processed. Even in these cases, the tendency of the granular SAP to be lost from the web is substantial.

Using the variations of the multicomponent particles (MDC) or a blend (MBIE) of acidic resin (polyacrylic acid) and poly(vinylamine) basic resin in a 50:50 by weight blend, product was made from 20% to 80% SAP content, with 5% bicomponent fiber, and also at 50% and 80% with no bicomponent fiber. It is not feasible to make such a structure with no bicomponent fiber, utilizing conventional SAP and no other adhesive or bonding additive.

Specifics of articles made and the basic steps that were followed are outlined as follows:

Airlaid Production at Pilot Line

Two types of multicomponent superabsorbent were used to make thin, highly densified airlaid nonwoven fabrics in roll form. Controls of conventional polyacrylate salt (sodium polyacrylate) SAP fabrics were also made when possible.

The process of forming these airlaid products involved the following steps:

A standard tissue sheet, of approximately 18-g/m² basis weight (BW) and appropriate porosity, was utilized as a carrier sheet for the subsequent mat to be supported on the forming wires. This carrier sheet was conveyed by the forming screen under several forming heads to which fluff pulp fibers, optionally bicomponent fibers, and the absorbent water-absorbent resin particles were conveyed by air, mechanically and pneumatically dispersed, and deposited upon the moving carrier sheet by a vacuum pulled from below the forming screen. The cellulosic fluff pulp fibers were generated from a fluff pulp roll that was metered to a hammermill that broke the pulp down into the component fibers and dispersed them into the conveying air. The bicomponent fibers, when used, were separated from bales, and metered into the conveying air by appropriate equipment. The granular absorbent polymer, whether multicomponent particles containing both acidic and basic resins (MDC), a blend of acidic resin particles with basic resin particles (MBIE), or conventional sodium polyacrylate, was metered into the conveying air by a loss in eight feeder.

The mats were compacted by nip rollers utilizing high pressure, e.g., 5,000–10,000 psi, and at slightly elevated temperature, approximately 40–60° C., then conveyed through a thru-air oven, operating at about 135° C. The heated web was then conveyed through a calender roll, also under high pressure and slightly elevated temperature. The mat was then optionally wound or slit to obtain an absorbent fabric of desired length and width.

During the process of making the airlaid absorbent fabrics, it was demonstrated that utilizing this type of dual absorbent material allowed a higher concentration of SAP particles to be incorporated in a lower portion of cellulosic fluff pulp fibers, from 50% to 80%, and it was also possible to do this without an increase in bicomponent (thermal-bondable) fibers, and in fact was possible without the use of any bicomponent fiber at all.

The resulting nonwoven fabrics were highly flexible, with a minimum of coarseness, had sufficient strength to handle through the process, and displayed very little SAP shakeout.

Laboratory Produced Cores

Cores were generated using the lab core-formed or other manual means. The core former, which is an apparatus that creates cores to be made by air laid means for lab evaluation, was mainly used to evaluate the comparative multicomponent resin particles of MDC; MBIE—blends of the acidic and basic rsin components of MDC; and conventional SAP particles. Other laboratory "core work" showed that tissue laminates from 85% to 97% MDC could be formed utilizing only pressure and moisture, or pressure and heat. Tables 13–16 follow:

TABLE 13

Analysis of SAP extraction from Airlaid (dry process) samples
All samples were flexed for one minute and then shaken for a
further minute and the amount of SAP removed was measured

| Sample ID | % SAP | % bico | % fluff | % tissue/ moisture (20 g/m²)* | SAP type | Thickness (mm) | Density (g/m³) | BW (g/m²*) | weight of sample used (g) | weight of SAP in sample (g) | weight of SAP removed (g) | % SAP loss |
|---|---|---|---|---|---|---|---|---|---|---|---|---|
| A | 80 | 0 | 20 | 1 carrier | SAF | 0.89 | 0.23 | 205 | 5.02 | 4.016 | 0.36 | 7.2 |
| B | 80 | 0 | 20 | 1 carrier | LAF | 0.98 | 0.21 | 208 | 4.99 | 3.992 | 0.45 | 9.0 |
| C | 80 | 0 | 20 | 1 carrier | 50—50 MBIE | 0.93 | 0.21 | 196 | 4.87 | 3.896 | 0.48 | 9.9 |
| D | 80 | 0 | 20 | 2 carriers needed | 2300 | 1.03 | 0.20 | 205 | 5.43 | 4.070 | 4.34 | 79.9 |
| E | 95 | 0 | 0 | 5.0**/20* | LAF | 1.52 | 0.86 | 1312 | 1.15 | 1.093 | 0.032 | 2.8 |
| F | 97.5 | 0 | 0 | 2.5**/20* | SAF | 1.42 | 0.96 | 1369 | 1.07 | 1.043 | 0.014 | 1.3 |
| G | 97.5 | 0 | 0 | 2.5**/20* | MBIE | 1.55 | 0.87 | 1345 | 1.06 | 1.034 | 0.017 | 1.6 |
| H | 80 | 0 | 20 | 5.0**/20* | 2300 | Fell apart | | | | | | |

*= 20% H₂O , based on the dry weight of the resin particles, added to the tissue carrier(s).
**= percent by weight tissue, based on the dry weight of the sheet material product.
SAF = standard amine formulation MDC (50% PAA; 50% PVAm)
LAF = low amine formulation MDC (67% PAA; 33% PVAm)
MBIE = Blend of PAA and PVAm
2300 = Conventional SAP 2300 (Na polyacrylate) - required carrier tissue on top and bottom. Weight of tissue excluded form losses.

TABLE 14

Analysis of SAP extraction from Airlaid (dry process) samples
All samples were flexed for one minute and then shaken for a
further minute and the amount of SAP removed was measured

| Sample ID | % SAP | % bico | % fluff | SAP type | Thickness (mm) | Density (g/m³) | BW (g/m²*) | weight of sample used (g) | weight of SAP in sample (g) | weight of SAP removed (g) | % SAP loss |
|---|---|---|---|---|---|---|---|---|---|---|---|
| I | 80 | 0 | 20 | 10 SAP/90 SAF | 0.9 | 0.22 | 200 | 3.292 | 2.634 | 0.192 | 7.3 |
| J | 80 | 0 | 20 | 10 SAP/90 LAF | 0.95 | 0.2 | 193 | 2.785 | 2.228 | 0.661 | 29.7 |
| K | 80 | 0 | 20 | 90 SAP/10 SAF | 0.95 | 0.2 | 193 | 2.957 | 2.366 | 1.092 | 46.2 |
| L | 80 | 0 | 20 | 90 SAP/10 LAF | 0.95 | 0.19 | 180 | 2.42 | 1.936 | 1.255 | 64.8 |
| M | 80 | 0 | 20 | 50 SAP/50 SAF | 0.95 | 0.21 | 200 | 3.07 | 2.456 | 0.498 | 20.3 |
| N | 80 | 0 | 20 | 50 SAP/50 LAF | 0.95 | 0.21 | 200 | 3.086 | 2.469 | 0.572 | 23.2 |
| O | 80 | 0 | 20 | 100 SAP/0 MDC | 1 | 0.2 | 193 | 3.297 | 2.638 | 0.94 | 35.6 |
| P | 80 | 0 | 20 | 0 SAP/100 SAF | 1.2 | 0.17 | 200 | 2.932 | 2.346 | 0.232 | 9.9 |
| Q | 80 | 0 | 20 | 0 SAP/100 LAF | 0.95 | 0.24 | 227 | 3.185 | 2.548 | 0.198 | 7.8 |

SAF = standard amine formulation MDC (50% PAA; 50% PVAm)
LAF = low amine formulation MDC (67% PAA; 33% PVAm)

TABLE 14-continued

Analysis of SAP extraction from Airlaid (dry process) samples
All samples were flexed for one minute and then shaken for a
further minute and the amount of SAP removed was measured

| Sample ID | % SAP | % bico | % fluff | SAP type | Thickness (mm) | Density (g/m$^3$) | BW (g/m$^2$*) | weight of sample used (g) | weight of SAP in sample (g) | weight of SAP removed (g) | % SAP loss |
|---|---|---|---|---|---|---|---|---|---|---|---|

SAP = Conventional SAP (Na polyacrylate)
*Basis weight including 18 g/m$^2$ from tissue.

TABLE 15

Analysis of SAP extraction from Airlaid (dry process) samples
All samples were flexed for one minute and then shaken for
a further minute and the amount of SAP removed was measured

| Sample ID | % SAP | % bico | % fluff | SAP type | Thickness (mm) | Density (g/m$^3$) | BW (g/m$^2$*) | weight of sample used (g) | weight of SAP in sample (g) | weight of SAP removed (g) | % SAP loss |
|---|---|---|---|---|---|---|---|---|---|---|---|
| R | 50 | 5 | 45 | SAF | 0.79 | 0.28 | 218 | 2.756 | 1.378 | 0.0062 | 0.4 |
| S | 50 | 5 | 45 | 2440 | 1 | 0.2 | 218 | 2.608 | 1.304 | 0.3468 | 26.6 |
| T | 50 | 5 | 45 | LAF | 0.88 | 0.24 | 218 | 2.7354 | 1.368 | 0.0215 | 1.6 |
| U | 50 | 5 | 45 | CL15 | 1 | 0.2 | 218 | 2.484 | 1.242 | 0.2512 | 20.2 |
| V | 20 | 5 | 75 | LAF | 1.13 | 0.19 | 218 | 2.837 | 0.567 | 0.0262 | 4.6 |
| W | 80 | 5 | 15 | SAF | 0.6 | 0.36 | 218 | 2.5617 | 2.049 | 0.003 | 0.1 |
| X | 50 | 0 | 20 | SAF | 0.94 | 0.23 | 218 | 2.5877 | 1.294 | 0.0256 | 2.0 |
| Y | 80 | 5 | 15 | LAF | 0.59 | 0.32 | 218 | 2.3434 | 1.875 | 0.0313 | 1.7 |
| Z | 80 | 0 | 20 | SAF | 0.59 | 0.32 | 218 | 2.0494 | 1.640 | 0.0131 | 0.8 |
| AA | 80 | 0 | 20 | LAF | 0.68 | 0.3 | 218 | 2.8505 | 2.280 | 0.0479 | 2.1 |

SAF = standard amine formulation MDC (50% PAA; 50% PVAm)
LAF = low amine formulation MDC (67% PAA; 33% PVAm)
CL15 = Conventional SAP Salsorb CL15 (Na polyacrylate)
2440 = Conventional SAP 2440 (Na polyacrylate)
*Basis weight including 18 g/m$^2$ from tissue.

TABLE 16

Measurement of tensile strength of Airlaid (dry process)
water-absorbent sheet materials
All samples were measured for tensile strength in the machine
direction and cross machine direction.
Test was carried out according to EDANA test method

| Sample ID | % SAP | % bico[1] | % fluff | SAP type | Thickness (mm) | Density (g/m$^3$) | BW (g/m$^2$*) | CSA (mm$^2$) |
|---|---|---|---|---|---|---|---|---|
| A' | 50 | 5 | 45 | SAF | 0.79 | 0.28 | 218 | 39.5 |
| B' | | | | | | | | 39.5 |
| C' | | | | | | | | 39.5 |
| D' | 50 | 5 | 45 | 2440 | 1 | 0.2 | 218 | 50 |
| E' | | | | | | | | 50 |
| F' | | | | | | | | 50 |
| G' | 50 | 5 | 45 | LAF | 0.88 | 0.24 | 218 | 44 |
| H' | | | | | | | | 44 |
| I' | | | | | | | | 44 |
| J' | 50 | 5 | 45 | CL15 | 1 | 0.2 | 218 | 50 |
| K' | | | | | | | | 50 |
| L' | | | | | | | | 50 |
| M' | 20 | 5 | 75 | LAF | 1.13 | 0.19 | 218 | 56.5 |
| N' | | | | | | | | 56.5 |
| O' | | | | | | | | 56.5 |
| P' | 80 | 5 | 15 | SAF | 0.6 | 0.36 | 218 | 30 |
| Q' | | | | | | | | 30 |
| R' | | | | | | | | 30 |
| S' | 80 | 0 | 20 | SAF | 0.94 | 0.23 | 218 | 47 |
| T' | | | | | | | | 47 |
| U' | | | | | | | | 47 |
| V' | 80 | 5 | 15 | LAF | 0.59 | 0.32 | 218 | 29.5 |
| W' | | | | | | | | 29.5 |
| X' | | | | | | | | 29.5 |
| Y' | 80 | 0 | 20 | SAF | 0.59 | 0.32 | 218 | 29.5 |
| Z' | | | | | | | | 29.5 |
| AA' | | | | | | | | 29.5 |
| BB' | 80 | 0 | 20 | LAP | 0.68 | 0.3 | 218 | 34 |
| CC' | | | | | | | | 34 |
| DD' | | | | | | | | 34 |

| Sample ID | Original length[2] (mm) | Extension (mm) | % Strain | Load at break point (g) | Stress (Nmm$^2$) |
|---|---|---|---|---|---|
| | | Machine direction | | | |
| A' | 100 | 113.6 | 13.6 | 1814.0 | 45.9 |
| B' | 100 | 113.7 | 13.7 | 2595.0 | 40.4 |
| C' | 100 | 115.5 | 15.5 | 1558.0 | 39.4 |
| AVERAGE | | | 14.3 | 1655.7 | 41.9 |
| SD | | | 1.1 | 138.4 | 3.5 |
| D' | 100 | 114.9 | 14.9 | 791.0 | 15.8 |
| E' | 100 | 113.4 | 13.4 | 792.0 | 15.8 |
| F' | 100 | 113.7 | 13.7 | 753.0 | 15.1 |
| AVERAGE | | | 14.0 | 778.7 | 15.6 |
| SD | | | 0.8 | 22.2 | 0.4 |
| G' | 100 | 117.5 | 17.5 | 1087.0 | 24.7 |
| H' | 100 | 114.6 | 14.6 | 1026.0 | 23.3 |
| I' | 100 | 116.0 | 16.0 | 1093.0 | 24.8 |
| AVERAGE | | | 16.0 | 1068.7 | 24.3 |
| SD | | | 2.5 | 37.1 | 0.8 |
| J' | 100 | 119.1 | 19.1 | 1139.0 | 22.8 |
| K' | 100 | 114.7 | 14.7 | 915.0 | 18.3 |

TABLE 16-continued

Measurement of tensile strength of Airlaid (dry process) water-absorbent sheet materials
All samples were measured for tensile strength in the machine direction and cross machine direction.
Test was carried out according to EDANA test method

| | | | | | |
|---|---|---|---|---|---|
| L' | 100 | 116.0 | 16.0 | 1052.0 | 21.0 |
| AVERAGE | | | 16.6 | 1035.3 | 20.7 |
| SD | | | 2.3 | 112.9 | 2.3 |
| M' | 100 | 115.7 | 15.7 | 1095.0 | 19.4 |
| N' | 100 | 113.5 | 13.5 | 984.0 | 17.4 |
| O' | 100 | 114.3 | 14.3 | 1060.0 | 18.8 |
| AVERAGE | | | 14.5 | 1046.3 | 18.5 |
| SD | | | 1.1 | 56.7 | 1 |
| P' | 100 | 114.3 | 14.3 | 1225.0 | 40.8 |
| Q' | 100 | 116.0 | 16.0 | 1318.0 | 43.9 |
| R' | 100 | 115.6 | 15.6 | 1275.0 | 42.5 |
| AVERAGE | | | 15.3 | 1272.7 | 42.4 |
| SD | | | 0.9 | 46.5 | 1.6 |
| S' | 100 | 115.7 | 15.7 | 1092.0 | 23.2 |
| T' | 100 | 112.4 | 12.4 | 912.0 | 19.4 |
| U' | 100 | 114.3 | 14.3 | 1060.0 | 22.6 |
| AVERAGE | | | 14.1 | 1021.3 | 21.7 |
| SD | | | 1.7 | 96.0 | 2.0 |
| V' | 100 | 115.1 | 15.1 | 905.0 | 30.7 |
| W' | 100 | 115.6 | 15.6 | 964.0 | 32.7 |
| X' | 100 | 213.5 | 13.5 | 839.0 | 28.4 |
| AVERAGE | | | 14.7 | 902.7 | 30.6 |
| SD | | | 1.1 | 62.5 | 2.1 |
| Y' | 100 | 115.8 | 15.8 | 1041.0 | 35.3 |
| Z' | 100 | 115.0 | 15.0 | 934.0 | 31.7 |
| AA' | 100 | 114.9 | 14.9 | 865.0 | 29.3 |
| AVERAGE | | | 15.2 | 94.7 | 32.1 |
| SD | | | 0.5 | 88.7 | 3.0 |
| BB' | 100 | 114.3 | 14.3 | 669.0 | 19.7 |
| CC' | 100 | 115.5 | 15.5 | 716.0 | 21.1 |
| DD' | 100 | 115.3 | 15.3 | 746.0 | 21.9 |
| AVERAGE | | | 15.0 | 710 | 20.9 |
| SD | | | 0.6 | 38.8 | 1.1 |
| Cross direction | | | | | |
| A' | 100 | 112.7 | 12.7 | 985.0 | 24.9 |
| B' | 100 | 110.7 | 10.7 | 991.0 | 25.1122 |
| C' | 100 | 109.9 | 9.9 | 965.0 | 24.4 |
| AVERAGE | | | 11.1 | 980.3 | 24.8 |
| SD | | | 1.4 | 13.6 | 0.3 |
| D' | 100 | 113.7 | 13.7 | 421.0 | 8.4 |
| E' | 200 | 109.3 | 9.3 | 406.0 | 8.1 |
| F' | 100 | 112.5 | 12.5 | 392.0 | 7.8 |
| AVERAGE | | | 11.8 | 406.3 | 8.1 |
| SD | | | 2.3 | 14.5 | 0.3 |
| G' | 100 | 111.3 | 11.3 | 648.0 | 14.7 |
| H' | 100 | 111.6 | 11.6 | 632.0 | 14.4 |
| I' | 100 | 112.7 | 12.7 | 647.0 | 14.7 |
| AVERAGE | | | 11.9 | 642.3 | 14.6 |
| SD | | | 0.7 | 9.0 | 0.2 |
| J' | 100 | 106.6 | 6.6 | 380.0 | 7.6 |
| K' | 100 | 106.8 | 6.8 | 452.0 | 9.0 |
| L' | 100 | 109.5 | 9.5 | 530.0 | 10.6 |
| AVERAGE | | | 7.6 | 454.0 | 9.1 |
| SD | | | 1.6 | 75.0 | 1.5 |
| M' | 100 | 108.4 | 8.4 | 497.0 | 8.8 |
| N' | 100 | 110.8 | 10.8 | 556.0 | 9.8 |
| O' | 100 | 109.6 | 9.6 | 510.0 | 9.0 |
| AVERAGE | | | 9.0 | 521.0 | 9.2 |
| SD | | | 1.2 | 31.0 | 0.5 |
| P' | 100 | 112.8 | 12.8 | 885.0 | 29.5 |
| Q' | 100 | 116.6 | 16.6 | 818.0 | 27.3 |
| R' | 100 | 112.9 | 12.9 | 822.0 | 27.4 |
| AVERAGE | | | 14.1 | 841.7 | 28.1 |
| SD | | | 2.2 | 37.6 | 1.3 |
| S' | 100 | 109.5 | 9.5 | 577.7 | 12.3 |
| T' | 100 | 110.0 | 10.0 | 610.2 | 13.0 |
| U' | 100 | | | | |
| AVERAGE | | | 9.8 | 594.0 | 12.6 |
| SD | | | 0.4 | 23.0 | 0.5 |
| V' | 100 | 111.8 | 11.8 | 502.7 | 17.0 |
| W' | 100 | 112.9 | 12.9 | 545.7 | 18.5 |
| X' | 100 | 115.5 | 15.5 | 512.1 | 17.4 |
| AVERAGE | | | 13.4 | 520.2 | 17.6 |
| SD | | | 1.9 | 22.6 | 0.8 |
| Y' | 100 | 109.0 | 9.0 | 486.4 | 16.5 |
| Z' | 100 | 108.0 | 8.0 | 474.2 | 16.1 |
| AA' | 100 | 108.0 | 8.0 | 483.7 | 16.4 |
| AVERAGE | | | 8.3 | 481.4 | 16.3 |
| SD | | | 0.6 | 6.4 | 0.2 |
| BB' | 100 | 110.5 | 10.5 | 30/.8 | 9.1 |
| CC' | 100 | 107.0 | 7.0 | 240.4 | 7.1 |
| DD' | 100 | | | | |
| AVERAGE | | | 8.8 | 274.1 | 8.1 |
| SD | | | 2.5 | 47.7 | 1.4 |

[1] polyethylene fiber
[2] width of all samples was 50 mm.

The following are some of the potential uses and advantages of the above described processes and products:

The above data show that the sheet materials of the present invention have excellent structural integrity in a nonwoven fabric utilizing only multicomponent absorbent particles, such as MDC and/or MBIE and a small amount of cellulosic or other comparable fibers/carrier, even with an optional small proportion of other binding material, such as bicomponent fiber. The sheet materials provide enhanced economics, feel and performance. Without the need for binder, manufacturing costs are lower as well as enhanced absorbency upon hydration by aqueous fluids in use.

A smooth feel in a very thin absorbent fabric, even with very high addition levels of the granular MDC or MBIE minimizes aesthetic issues for personal care applications. The minimum of shakeout and loss of the granular absorbent resin particles is of significant importance to manufacture, conversion, and use of the absorbent fabric.

The above data shows that the sheet materials of the present invention deliver highly localized absorption, post-hydration acquisition, or deionizing capability to personal care disposable hygienics, or to other disposable applications where such attributes were not currently available. It could be envisioned that this type fabric in a disposable hygienic application could be used singularly or in combination with traditional core materials, to boost absorbency in the critical "insult" area, or be used as a layer in the same region to aid in acquisition, absorption, and deionization of "distributed" liquid, thus leading to enhanced absorption by conventional SAP in lower or outlying regions.

What is claimed is:

1. A process for manufacturing a water-absorbent sheet material comprising a lightly cross-linked unneutralized acidic water-absorbent resin and a lightly crosslinked unneutralized basic water-absorbent resin comprising:

depositing particles of the acidic and the basic water-absorbent resins onto a support surface to form a continuous layer of water-absorbent resin particles; and compressing the layer of resin particles to form the water-absorbent sheet material in a predetermined thickness.

2. The process of claim 1 further including the step of contacting the resin particles with a bonding expedient selected from the group consisting of water, propylene glycol, glycerin, a $C_1$–$C_3$ alcohol, dimethyl formamide, dimethyl sulfoxide, heat, and a combination thereof, prior to or simultaneously with compressing the resin particles, to bond adjacent water-absorbent resin particles.

3. The process of claim 1 wherein the basic water-absorbing resin is neutralized 0% to 25% and the acidic water-absorbing resin is neutralized 0% to 25%.

4. The process of claim 3 further including depositing a second acidic water-absorbing resin neutralized 25% to 100%.

5. The process of claim 4 wherein the second acidic water-absorbing resin neutralized 25% to 100% is poly(acrylic acid).

6. The process of claim 1 wherein the basic water-absorbing resin is poly(vinylamine).

7. The process of claim 6 wherein the poly(vinylamine) is surface crosslinked with up to about 1% of a surface crosslinking agent, by weight of the poly(vinylamine).

8. The process of claim 7 wherein the surface crosslinking agent comprises ethylene glycol diglycidyl ether.

9. The process of claim 1 wherein the acidic resin is selected from the group consisting of polyacrylic acid, a hydrolyzed starch-acrylonitrile graft copolymer, a starch-acrylic acid graft copolymer, a saponified vinyl acetate-acrylic ester copolymer, a hydrolyzed acrylonitrile copolymer, a hydrolyzed acrylamide copolymer, an ethylene-maleic anhydride copolymer, an isobutylene-maleic anhydride copolymer, a poly(vinylsulfonic acid), a poly(vinylsulfuric acid), a poly(vinylphosphoric acid), a sulfonated polystyrene, a poly(vinylphosphonic acid), and mixtures thereof.

10. The process of claim 1 wherein the basic water-absorbing resin and the acidic resin are present in a weight ratio of about 5:95 to about 95:5.

11. The process of claim 1 wherein the basic water-absorbing resin and the acidic resin are present in a weight ratio of about 20:80 to about 80:20.

12. The process of claim 1 wherein the basic water-absorbing resin and the acidic resin are present in a weight ratio of about 20:80 to about 40:60.

13. The process of claim 6 wherein the poly(vinylamine) is a homopolymer.

14. The process of claim 6 wherein the poly(vinylamine) comprises vinylamine and at least one additional monoethylenically unsaturated monomer.

15. The process of claim 1 wherein the acidic water-absorbent resin and the basic water-absorbing resin are formed together into multicomponent superabsorbent particles, said particles manufactured to contain both resins.

16. The process of claim 15 further including particles of a single component water-absorbing resin selected from the group consisting of an acidic water-absorbing resin, a basic water-absorbing resin, and mixtures thereof.

17. The process of claim 15 wherein the multicomponent superabsorbent particles are present in an amount of about 10% to about 90% by weight, based on the weight of water-absorbing resins contained in the sheet material layer.

18. The process of claim 16 wherein the multicomponent superabsorbent particles are 0% to 25% neutralized, and the single component water-absorbing resin is 0% to 100% neutralized.

19. The process of claim 15 wherein each multicomponent superabsorbent particle comprises at least one microdomain of the acidic water-absorbing resin in contact with at least one microdomain of the poly(vinylamine) resin.

20. The process of claim 19 wherein the multicomponent superabsorbent particles are in the form of a bead, a granule, a flake, an interpenetrating polymer network, a fiber, an agglomerated particle, a laminate, a powder, a foam, or a sheet.

21. The process of claim 15 wherein each multicomponent superabsorbent particle comprises at least one microdomain of an acidic water-absorbing resin in close proximity to at least one microdomain of said poly(vinylamine) water-absorbing resin.

22. The process of claim 16 wherein the single component water-absorbing resin has a degree of neutralization from 0 to 70.

23. The process of claim 16 wherein the single-component water-absorbing resin comprises an acidic water-absorbing resin.

24. The process of claim 23 wherein the single component acidic water-absorbing resin is selected from the group consisting of polyacrylic acid, a hydrolyzed starch-acrylonitrile graft copolymer, a starch-acrylic acid graft copolymer, a saponified vinyl acetate-acrylic ester copolymer, a hydrolyzed acrylonitrile polymer, a hydrolyzed acrylamide copolymer, an ethylene-maleic anhydride copolymer, an isobutylene-maleic anhydride copolymer, a poly(vinylphosphonic acid), a poly(vinylsulfonic acid), a poly(vinylphosphoric acid), a poly(vinylsulfuric acid), a sulfonated polystyrene, a poly(aspartic aid), a poly(lactic acid), and mixtures thereof.

25. The process of claim 16 wherein the single-component water-absorbing resin comprises a basic water-absorbing resin.

26. The process of claim 1 wherein the basic water-absorbing resin is selected from the group consisting of a poly(vinylamine), a poly(dialkylaminoalkyl(meth)acrylamide), a polymer prepared from the ester analog of an N-(dialkylamino(meth)acrylamide), a polyethylenimine, a poly(vinylguanidine), a poly(allylguanidine), a poly(allylamine), a poly(dimethyldialkylammonium hydroxide), a guanidine-modified polystyrene, a quaternized polystyrene, a quaternized poly(meth)acrylamide or ester analog thereof, poly(vinyl-alcohol-co-vinylamine), and mixtures thereof.

27. The process of claim 25 wherein the basic water-absorbing resin is selected from the group consisting of a poly(vinylamine), a poly(dialkylaminoalkyl(meth)acrylamide), a polymer prepared from the ester analog of an N-(dialkylamino(meth)acrylamide), a polyethylenimine, a poly(vinylguanidine), a poly(allylguanidine), a poly(allylamine), a poly(dimethyldialkylammonium hydroxide), a guanidine-modified polystyrene, a quaternized polystyrene, a quaternized poly(meth)acrylamide or ester analog thereof, poly(vinyl-alcohol-co-vinylamine), and mixtures thereof.

28. The process of claim 1 wherein the sheet material has an absorption under load of 0.7 psi of at least about 20 grams of 0.9% saline per gram of particles, after one hour, and at least about 30 grams of 0.9% saline per gram of particles after three hours.

29. The process of claim 1 wherein the sheet material has a saline flow conductivity value of greater than $15 \times 10^{-7}$ cm$^3$ sec/g.

30. The process of claim 1 wherein the sheet material has an initial performance under pressure capacity rate of greater than 40 g/g/hr$^{1/2}$.

31. The process of claim 1 wherein the sheet material has a free swell rate greater than 0.30 g/g/sec.

32. The process of claim 1 wherein the resin particles are formed into a sheet material by a wet process comprising mixing the resin particles with water to form a slurry comprising said resin particles in hydrated form; depositing the slurry of hydrated resin particles onto said support surface wherein the support surface is water-pervious; removing a majority of said water by draining said water through said support surface, while retaining said hydrated resin particles on said support surface; compressing the resin particles in the form of a sheet; and drying said sheet of resin particles.

33. The process of claim 32 wherein 2% to about 50% by weight fibers, based on the total weight of the dry sheet material, are added to the slurry and mixed with the hydrated resin particles prior to depositing the slurry onto said support surface.

34. The process of claim 33 wherein the fibers comprise cellulosic fibers, present in the sheet material in an amount of 2% to about 50% by weight, based on the dry weight of the sheet material.

35. The process of claim 34 wherein the cellulosic fibers are present in the sheet material in an amount of 5% to about 20% by weight, based on the dry weight of the sheet material.

36. The process of claim 33 wherein thermoplastic fibers are added to the slurry, in an amount of about 1% to about 10% by weight, based on the total weight of the dry sheet material.

37. The process of claim 35 wherein thermoplastic fibers are added to the slurry, in an amount of about 1% to about 10% by weight, based on the total weight of the dry sheet material.

38. The process of claim 36 wherein the thermoplastic fibers are selected from the group consisting of polyethylene, polypropylene, a copolymer of ethylene and propylene, polyethylene terephthalate, and mixtures thereof.

39. The process of claim 32 wherein the hydrated resin particles are partially dried and compressed between a pair of pressure rollers, at least one of said pressure rollers being heated to a temperature of at least 40° C.

40. The process of claim 1 wherein the resin particles are deposited onto the support surface by airlaying to form a continuous resin layer.

41. The process of claim 40 wherein at least about 2% by weight water is added to the resin particles, based on the dry weight of the resin particles, to bind the particles together.

42. The process of claim 41 wherein water is added to the resin particles in an amount of about 2% by weight to about 30% by weight, based on the dry weight of the resin particles.

43. The process of claim 40 wherein the resin layer is heated to the glass transition temperature of the basic water absorbing resin particles to bind adjacent resin particles together.

44. The process of claim 43 wherein the resin layer is heated to a temperature in the range of about 55° C. to about 150° C. for a period of time sufficient to bind adjacent resin particles together.

45. The process of claim 40 further including the step of disposing a flexible support sheet over the support surface, and depositing the airlaid resin particles onto the flexible support sheet.

46. The process of claim 45 further including depositing a second flexible sheet of material on top of the continuous layer of resin particles, and thereafter heating the resin particles to adhere the top sheet of flexible material to the top surface of the layer of resin particles.

47. The process of claim 46 wherein the top sheet of flexible material is a water-impervious, continuous polymeric sheet.

48. The process of claim 47 wherein the top sheet of flexible material is coextensive with the top surface of the layer of resin particles.

49. The process of claim 1 wherein the resin particles are at least partially hydrated, with 2% to about 100% by weight water, based on the dry weight of the resin particles, prior to depositing the resin particles onto the support surface.

50. The process of claim 40, further including mixing fibers with said resin particles, in an amount of about 2% to about 50% by weight, based on the dry weight of the sheet material, and thereafter adhering the resin particles together with a bonding expedient selected from the group consisting of water, heat, and a combination of water and heat.

* * * * *